United States Patent
Hu et al.

(10) Patent No.: US 12,324,817 B2
(45) Date of Patent: *Jun. 10, 2025

(54) METHOD OF INDUCING DEDIFFERENTIATION OF SOMATIC CELLS WITH SMALL MOLECULES TO PREPARE REJUVENATED MESENCHYMAL STEM CELLS AND USES THEREOF

(71) Applicant: SHENZHEN ALPHA BIOPHARMACEUTICAL CO. LTD., Guangdong (CN)

(72) Inventors: Min Hu, Yunnan (CN); Yanjiao Li, Yunnan (CN); Junyuan Hu, Guangdong (CN)

(73) Assignee: SHENZHEN ALPHA BIOPHARMACEUTICAL CO. LTD., Shenzhen (CN)

( * ) Notice: Subject to any disclaimer, the term of this patent is extended or adjusted under 35 U.S.C. 154(b) by 741 days.

This patent is subject to a terminal disclaimer.

(21) Appl. No.: 17/086,397

(22) Filed: Oct. 31, 2020

(65) Prior Publication Data
US 2021/0213069 A1 Jul. 15, 2021

Related U.S. Application Data

(63) Continuation of application No. PCT/CN2019/085401, filed on May 1, 2019.

(30) Foreign Application Priority Data

May 1, 2018 (CN) .......................... 201810407290.X

(51) Int. Cl.
*A61K 35/33* (2015.01)
*C12N 5/077* (2010.01)

(52) U.S. Cl.
CPC ............ *A61K 35/33* (2013.01); *C12N 5/0656* (2013.01); *C12N 2501/01* (2013.01); *C12N 2501/03* (2013.01); *C12N 2501/155* (2013.01); *C12N 2501/165* (2013.01); *C12N 2501/21* (2013.01); *C12N 2501/2302* (2013.01); *C12N 2501/2306* (2013.01); *C12N 2501/24* (2013.01); *C12N 2501/25* (2013.01); *C12N 2501/999* (2013.01)

(58) Field of Classification Search
CPC ... A61K 35/33; C12N 5/0656; C12N 2501/01
See application file for complete search history.

(56) References Cited

FOREIGN PATENT DOCUMENTS

WO 2009042798 A1 4/2009
WO WO2011159726 A2 * 12/2011 ............... C12N 5/16

OTHER PUBLICATIONS

R&D Systems, Pyridone 6 catalog 6577, retrieved from internet Sep. 12, 2023. (Year: 2023).*
ThermoFisher, Cell culture media, Retrieved from internet Mar. 18, 2024. (Year: 2024).*
Lai et al., Efficient Generation of Chemically Induced Mesenchymal Stem Cells from Human Dermal Fibroblasts, Scientific Reports, 7(44534): p. 1-13. (Year: 2017).*
Heldin et all., Signaling Receptors of TGF-b Family Members, Cold Spring Harbor Laboratory Press, p. 1-33 (Year: 2016).*
Niehrs et al., The complex world of WNT receptor signaling, Molecular Cell Biology, 13: 767-779. (Year: 2012).*
Yan et al., The cyclic AMP signaling pathway: Exploring targets for successful drug discovery, Molecular Medicine Reports, 13: 3715-3723. (Year: 2016).*
Wang Yu, Zhu Zhen-Xin, Cai Qing-Ping; Senescence-associated secretory phenotype and its complex regulation networks: a review of molecular mechanisms; Apr. 20, 2018; Department of General Surgery ( II ), Changzheng Hospital, Navy Medical University (Second Military Medical University), Shanghai 200003, China.
Sona Hubackova, Zora Novakova, .ETC.;Regulation of the PML tumor suppressor in drug-induced senescence of human normal and cancer cells by JAK/STAT-mediated signaling; Aug. 1, 2010;Biology of Reproduction Department; Institute of Animal Science; Prague, Czech Republic; ‡Hospital for Special Surgery; Department of Microbiology and Immunology; Weill Medical College of Cornell University; New York, NY USA.

* cited by examiner

*Primary Examiner* — Arthur S Leonard
*Assistant Examiner* — Joseph Paul Miano

(57) ABSTRACT

A preparation method and applications of rejuvenated and regenerative fibroblasts, where the rejuvenated and regenerative fibroblasts are prepared from normal fibroblasts by inhibiting the JAK-STAT signaling pathway. The rejuvenated and regenerative fibroblasts are prepared by treating the target cells with a small molecular combination, a cytokine combination or a recombinant protein combination. This application further provides an application of the rejuvenated and regenerative fibroblasts in the reprogramming or rejuvenation of cells, tissues, organs and organisms.

12 Claims, 55 Drawing Sheets

Operation Schematic Diagram

METHOD OF INDUCING DEDIFFERENTIATION OF SOMATIC CELLS WITH SMALL MOLECULES TO PREPARE REJUVENATED MESENCHYMAL STEM CELLS AND USES THEREOF

CROSS-REFERENCE TO RELATED APPLICATIONS

This application is a continuation of International Patent Application No. PCT/CN2019/085401, filed on May 1, 2019, which claims the benefit of priority from Chinese Patent Application No. 201810407290.X with a filing date of May 1, 2018. The content of the aforementioned applications, including any intervening amendments thereto, is incorporated herein by reference in their entirety.

TECHNICAL FIELD

The present application relates to cell biology, and more particularly to a method of inducing dedifferentiation of somatic cells with small molecules to prepare rejuvenated mesenchymal stem cells and uses thereof.

BACKGROUND

Stem cells are considered as "Holy Grail" in the regenerative medicine and anti-aging fields. Generally, the aging of an organism is accompanied by the aging of stem cells, which will bring the malignant transformation or degeneration of various organs including bone, cartilage, heart, muscle, brain, skin, pancreas, liver, kidney and gastrointestinal tract. Moreover, the aging may also cause the dysfunction of immune system. In fact, the chronic inflammation is also a cause of the degeneration and aging of tissues and organs. The aged cells usually suffer DNA damage or mutations, telomere shortening, abnormal epigenetics, redox, and energy metabolism, declined proliferation capacity and increased death rate. The aged stem cells tend to lose the potential to differentiate into certain lineages while biasing towards others. For example, it is well known that the bone marrow mesenchymal stem cells from an elderly individual have decreased osteogenic or chondrogenic potential but increased adipogenic potential. Therefore, the bone marrow derived from an elderly person is often filled with fat tissues and thus called "yellow bone marrow". Similarly, the neural stem cells of the elderly will also tend to differentiate into astrocytes rather than neurons, which is believed to be related to the decline in cognitive ability of the elderly.

Stem cells, especially mesenchymal stem cells, have exhibited strong potential in the treatment or intervention of the aging process and related diseases since they are readily available, expandable and pluripotent, and can release growth factors and regulate the immune system. Currently, the mesenchymal stem cells have been widely used in the clinical treatment of various diseases, such as graft-versus-host disease (GVHD), multiple sclerosis (MS), amyotrophic lateral sclerosis (ALS), spinal cord injury (SCI), lupus erythematosus (LE), arthritis and aging. Among the mesenchymal stem cells (MSCs), umbilical cord mesenchymal stem cells are widely considered to be suitable for the allogeneic uses, but the long-term/repetitive use of "non-self" cells presents a clinical risk. By contrast, autologous stem cell transplantation is considered safer, but unfortunately, the mesenchymal stem cells also become aged as the individual ages, and the aged MSCs are greatly limited in clinical application due to the loss of many important functions. Induced pluripotent stem (iPS) cells are a class of young cells that can be obtained from the elderly, and have been deemed as a desired autologous cell source of cells for treatment. However, the preparation of iPS cells involves poor induction efficiency and the introduction of foreign genes, which is often accompanied by genetic variation, limiting the clinical promotion. In addition, genetic modification has been recently used as another tool in the cell rejuvenation, but this method still has the risk of off-target and tumorigenesis. Therefore, it is of considerable significance to targetedly develop a preparation method of self-rejuvenated, safe and regenerative cells for delaying and reversing the process of human aging and repairing the structure or function of tissues and organs.

SUMMARY

An object of this application is to provide a method of inducing dedifferentiation of somatic cells with small molecules to prepare rejuvenated mesenchymal stem cells and uses thereof, where the method involves the regulation of JAK-STAT (Janus kinase-signal transducer and activator of transcription) signaling pathway to regulate cell differentiation, dedifferentiation, transdifferentiation, rejuvenation, aging and apoptosis, reversing the aging process and prolonging the lifespan. Moreover, the cells prepared through the above method such as regenerative fibroblast (rFib) and induced rejuvenated mesenchymal stem cell (irMSC) can be employed to prevent, delay and reverse the human aging process and repair the structure or function of tissues and organs. The regenerative fibroblasts prepared herein have both the characteristics of skin fibroblasts and mesenchymal stem cells, and thus are also named induced and rejuvenated mesenchymal stem cells (irMSCs) or induced mesenchymal stem cells (iMSCs) (uniformly referring to as rFib herein).

Technical solutions of this application are described as follows.

In a first aspect, this application provides a method of preparing rejuvenated mesenchymal stem cells or regenerative fibroblasts from target cells, comprising:
  regulating an expression of a gene or protein target involved in JAK-STAT signaling pathway to activate or inhibit the JAK-STAT signaling pathway quantitatively and/or in a timing manner in the target cells to prepare the rejuvenated mesenchymal stem cells or regenerative fibroblasts;
  wherein the gene or protein target involved in the JAK-STAT signaling pathway is selected from the group consisting of: CXCL2 (Accession No: AY577905.1), SOS1 (Accession No: NM_005633.3), STAT5B (Accession No: NM_012448.3), JAK1 (Accession No: NM_001321857.1), JAK3 (Accession No: NM_000215.3), SOCS3 (Accession No: NM_003955.4), IL6ST (Accession No: NM_001243835.1), STAT1 (Accession No: NM_007315.3), STAT2 (Accession No: NM_198332.1), STAT3 (Accession No: NM_213662.1), STAT4 (Accession No: NM_001243835.1), STAT6 (Accession No: NM_001178081.1), STAT5A (Accession No: NM_001288720.1), IRF9 (Accession No: NM_006084.4), IL6 (Accession No: XM_005249745.5), IL6R (Accession No: NM_181359.2), IL2 (Accession No: NM_000586.3) (such as IL2A and IL2B), PRKCD (Accession No: NM_001354679.1), CXCL12 (Accession No:

NM_000609.6), CXCR4 (Accession No: NM_003467.2), JAK2 (Accession No: NM_004972.3), IL15RA (Accession No: NM_001351095.1), IL20RB (Accession No: XM_006713665.4), GHR (Accession No: NM_001242406.2), PRLR (Accession No: NM_001204314.2) and a combination thereof.

In an embodiment, the target cells are derived from mammals, such as humans, mice, monkeys, dogs and pigs, and are selected from the group consisting of fibroblasts, epithelial cells, adipocytes, blood cells, mesenchymal stem cells, nerve cells, muscle cells, cardiomyocytes, smooth muscle cells, vascular endothelial cells, induced pluripotent stem cells, embryonic stem cells, osteoblasts, chondrocytes and osteoclasts. The rejuvenated mesenchymal stem cells prepared herein are derived from the target cells and other cell types can also be produced in the process associated with the regulation of the JAK-STAT signaling pathway, where the process associated with the regulation of the JAK-STAT signaling pathway includes differentiation, dedifferentiation, transdifferentiation, rejuvenation, aging and apoptosis.

In an embodiment, the quantitative activation or inhibition of the JAK-STAT signaling pathway indicates that the expression of at least one of the gene or protein targets involved in the JAK-STAT signaling pathway in the rejuvenated and regenerative fibroblasts or irMSC is up-regulated or down-regulated by 1-300 times relative to the target cells.

In an embodiment, the activation or inhibition of the JAK-STAT signaling pathway in a timing manner indicates that at least one of the gene or protein targets involved in the JAK-STAT signaling pathway in the target cells is regulated to experience high expression, low expression or no expression for 24 hours-220 days, and the resulting cells can maintain the high expression, low expression or no expression of the at least one of the gene or protein targets in the long term, or recover to be the same as the target cells in the expression level.

In an embodiment, the activation or inhibition of the JAK-STAT signaling pathway is performed by regulating at least one of the following pathways or targets: NOD-like receptor signaling pathway, Focal adhesion, cell cycle, tricarboxylic acid cycle (TCA), TGF beta signaling pathway, WNT signaling pathway, Notch signaling pathway, P53 signaling pathway, insulin signaling pathway, calcium signaling pathway, Interleukin-19, Interleukin-20, Interleukin-22, Interleukin-24, IL7, histone deacetylase (HDAC), PKC signaling pathway, RAR pathway, adenylate cyclase signaling pathway, histone methyltransferase (HMT) inhibitors, DNA methyltransferase (DNMT) inhibitors and histone demethylase inhibitors.

In an embodiment, the regulation of the NOD-like receptor signaling pathway is performed by regulating an expression of a gene or protein target selected from the group consisting of NAIP, IL6, CXCL12, NOD1, TAB3, CARD6, CXCL2, CXCL1, CXCL3, CARD8, CARD9, CASP1, CASP12, CASP4, CASP5, NFKB1, TMEM173, TNF, NFKBIB, NOD2, PYDC1, PYCARD, TAB1, TAB2, TNF, TLR4, NLRP1, NLRP12, NLRP3, NLRP6, MCU, RIPK3, RHOA, TAK1, BIRC2, ATG16L1, ATG5, ATG12, TANK and a combination thereof.

In an embodiment, the regulation of the Focal adhesion pathway is performed by regulating an expression of a gene or protein target selected from the group consisting of TNXB, RAPGEF1, ITGB8, SRC, THBS1, ITGA3, VCL, CAPN2, FLT4, FLT1, ITGA3, ITGB1, ITGB3, ITGB5, ITGB6, ITGB7, ITGA1, ITGA10, ITGA11, ITGA2, ITGA2B, ITGA5, ITGA6, ITGA7, ITGA8, ITGA9, ITGAV, PDRVG, PDGFA, PDGFB, PDGFC, PDGFD, PDGFRA, PDGFRB, BIRC3, BIRC2, BCL2, DOCK1, FN1, HGF, EGF, EGFR, IGF1, IGFIR, VEGFA, VEGFB, VEGFC, CTNNB1 and a combination thereof.

In an embodiment, the regulation of the cell cycle is performed by regulating an expression of a gene or protein target selected from the group consisting of MAD2L1, BUB1, ORC1, ORC2, ORC3, ORC4, ORC5, ORC6, ATM, ATR, CCNA1, CCNA2, CCNB1, CCNB2, CCNB3, CCND1, CCND2, SMAD2, SMAD3, SMAD4, E2F2, E2F3, E2F4, E2F5, EP300, FZR1, GADD45A, GADD45B, STAG1, STAG2, CDC14A, CDC14B, CDC20, CDC25A, CDC25B, MYC, SMC3, CDC16, YWHAH, YWHAB, YWHAQ, YWHAE, YWHAG, YWHAZ and a combination thereof.

In an embodiment, the regulation of the tricarboxylic acid cycle is performed by regulating an expression of a gene or protein target selected from the group consisting of IDH3G, IDH3B, MDH2, SDHB, OGDH, MDH1, OGDHL, SUCLG1, SUCLG2, SUCLA2, SDHA, SDHB, SDHC, PDHA1, PDHB, ACLY and a combination thereof.

In an embodiment, the regulation of the TGF beta signaling pathway is performed by regulating an expression of a gene or protein target selected from the group consisting of ACVR1C, THBS1, FST, TGFB1, TGFBR1, TGFBR2, TGFBR3, BMP4, RUNX3, RUNX2, CREBBP, IFNG, HRAS, FOS, TGFB2, TGFB3, ACVRL1, FOXO3, MTOR, KRAS, CREB1, ATF1, ATF2, ATF4, AKT1, AKT2, AKT3, HNF4A, HNF4G, PIK3R3 and a combination thereof.

In an embodiment, the regulation of the WNT signaling pathway is performed by regulating an expression of a gene or protein target selected from the group consisting of PRKCA, WNT7B, PRICKLE1, LRP6, CTNNB1, FZD4, CCND2, PRICK, WNT5A, WNT1, WNT10A, WNT11, WNT9A, WNT9B, WNT3, WNT4B and a combination thereof.

In an embodiment, the regulation of the Notch signaling pathway is performed by regulating an expression of a gene or protein target selected from the group consisting of CIR1, KAT2B, MAML2, PSEN2, DVL2, RFNG, SNW1, DLL4, DTX3, DLL3, DLL1, DTX1, DTX2, CREBBP, CTBP1, CTBP2, JAG1, JAG2, NOTCH1, NOTCH2, NOTCH3, NOTCH4, PSEN1, PSEN2 and a combination thereof.

In an embodiment, the regulation of the P53 signaling pathway is performed by regulating an expression of a gene or protein target selected from the group consisting of CCNG2, SIAH1, BBC3, TP53AIP1, TP53, SETD7, ATF3, CCNA2, CDK2, CCNG1, CHEK1, PRKCD, KAT2B, PRL23, PPP2CA and a combination thereof.

In an embodiment, the regulation of the calcium signaling pathway is performed by regulating an expression of a gene or protein target selected from the group consisting of RYR1, RYR2, RYR3, ESR1, AR (androgen receptor), KDR (kinase insert domain receptor), VDR (vitamin D receptor), ITPR1, ITPR2, ITPR3, PDE1A, PDE1B, PDE1C, PRKCA, PRKCD, PRKCE, PRKCG and a combination thereof.

In an embodiment, the regulation of the insulin signaling pathway is performed by regulating an expression of a gene or protein target selected from the group consisting of RAPGEF1, PHKG1, PYGL, TRIP10, INS, INSR, IRS1, PDPK1, PIK3CA, HRAS, GRB2, PTPN1, PTPN11 and a combination thereof.

In an embodiment, the regulation of the PKC signaling pathway is performed by regulating an expression of a gene or protein target selected from the group consisting of PRKCA, PRKCB, PRKDC, PRKCZ, PRKCE, PRKCG, PRKCD, PRKCH, PRKCI, PRKCQ, PRKD1, SLC9A5, MAPK3, MAPK9, MAPK8, MAPK1 and a combination thereof.

In an embodiment, the regulation of the RAR pathway is performed by regulating an expression of a gene or protein target selected from the group consisting of RARA, RARS, RARB, RARG, RXRA, RXRG, FAM120B, NCOA1, NCOR2 and a combination thereof.

In an embodiment, the regulation of HDAC is performed by regulating an expression of a gene or protein target selected from the group consisting of HDAC1, HDAC2, HDAC3, HDAC4, HDAC5, HDAC6, HDAC7, HDAC8, HDAC9, HDAC10, HDAC11 and a combination thereof.

In an embodiment, the regulation of adenylate cyclase signaling pathway is performed by regulating an expression of a gene or protein target selected from the group consisting of PRKAR1A, ADCY10, ADCYAP1, ADCY1, ADCY2, ADCY6, ADCY3, GNAI1, GNAL, GNAT3, PRKACA, PRKAR2B, PRKACB, PRKAR1B, PRKACG, CDKN1B, PRKAR2A, NCAM1, CDKN1A (cyclin dependent kinase inhibitor 1A) and a combination thereof.

In an embodiment, the regulation of HMT is performed by regulating an expression of a gene or protein target selected from the group consisting of HNMT, DNMT1, KMT2A, EHMT2, EHMT1, KMT2A, DOT1L, EZH2, SETD7, DNMT3B, DNMT3A, SETDB1, SETD2 and a combination thereof.

In an embodiment, the regulation of DNMT is performed by regulating an expression of a gene or protein target selected from the group consisting of DNMT1, DNMT3B, DNMT3A, CDKN2A, CDKN2B, EHMT2, EHMT1, DNMT3L, CDH1, PARP1, MBD2 and a combination thereof.

In an embodiment, the regulation of histone demethylase is performed by regulating an expression of a gene or protein target selected from the group consisting of KDM1A, KDM4A, KDM5A, KDM5B, KDM2A, KDM5C, KDM4B, KDM4C, KDM5D, KDM4D, KDM1B, HIST1H3A, HIST4H4, HIST2H3C, HAT1, HIST1H4C, HIST1H4F, HIST1H4J, HIST1H2AE, HIST1H2BB, CLOCK, NOCA1 and a combination thereof.

In an embodiment, the method is performed by a small molecule compound combination, a cytokine or recombinant protein combination, gene editing, transgenic technology or a combination thereof.

In an embodiment, the small molecule compound combination is a histone deacetylase inhibitor, a TGF-β receptor inhibitor, a PKC inhibitor, a WNT/β-catenin agonist, a cAMP agonist, a RAR agonist, a ROCK inhibitor, a JNK inhibitor, a DNMT inhibitor, a HMT inhibitor, a histone demethylase inhibitor, a JAK-STAT inhibitor or a combination thereof.

In an embodiment, the histone deacetylase inhibitor is selected from the group consisting of sodium phenylbutyrate, butyrate, sodium butyrate, VPA, Scriptaid, Apicidin, LBH-589 (Panobinostat), MS-275, SAHA (Vorinostat), Trichostatin (TSA), Psammaplin A, splitomicin, SRT1720, resveratrol, Sirtinol, APHA, CI-994, Depudecin, FK-228, HC-Toxin, ITF-2357 (Givinostat), Chidamide, RGFP 966, PHOB, BG45, Nexturastat A, TMP269, CAY10603, MGCD-0103, Niltubacin, PXD-101 (Belinostat), Pyroxamide, Tubacin, EX-527, BATCP, Cambinol, MOCPAC, PTACH, MC1568, NCH51, TC-H106 and a combination thereof.

In an embodiment, the TGF-β receptor inhibitor is selected from the group consisting of LY2109761 (Galunisertib), Pirfenidone, Repsox (E-616452), SB431542, A77-01, A8301, GW788388, ITD-1, SD208, SB525334, LY364947, ASP3029, D4476, SB505124 and a combination thereof.

In an embodiment, the PKC inhibitor is selected from the group consisting of Go6983, Go6976, Bisindolylmaleimide I (GF109203X) and a combination thereof.

In an embodiment, the WNT/β-catenin agonist is selected from the group consisting of MAY-262611, CHIR98014, CHIR99021, LiCl, Li$_2$CO$_3$, TD114-2, AZD2858, AZD1080, BIO, Kenpaullone, TWS119, LY2090314, CBM1078, SB216763, AR-A014418 and a combination thereof.

In an embodiment, the CAMP agonist is selected from the group consisting of Forskolin, IBMX, Prostaglandin E2 (PGE2), NKH477, 8-pCPT-2'-O-Me-CAMP, GSK256066, Apremilast (CC-10004), Roflumilast, Cilomilast, Rolipram, Milrinone, 8-Bromo-cAMP, Dibutyryl-Camp, Sp-8-Br-cAMPs and a combination thereof.

In an embodiment, the RAR agonist is selected from the group consisting of TTNPB, Bexarotene, Ch55, Tamibarotene, Retinol, AM580, ATRA, Vitamin A and its derivatives, 13-cis retinoic acid (RA) and a combination thereof.

In an embodiment, the ROCK inhibitor is selected from the group consisting of Y-27632, Y-27632 2HCl, Thiazovivin, Ripasudil (K-115), Fasudil, GSK429286A, RKI-1447, PKI-1313 and a combination thereof.

In an embodiment, the JNK inhibitor is selected from the group consisting of SP600125, JNK Inhibitor IX, AS601245, AS602801, JNK-IN-8 and a combination thereof.

In an embodiment, the DNMT inhibitor is selected from the group consisting of RG108, Thioguanine, 5-Aza-2'-deoxycytidine (Decitabine), SGI-1027, Zebularine, 5-Azacytidine (AZA) and a combination thereof.

In an embodiment, the HMT inhibitor is selected from the group consisting of EPZ004777, EPZ5676, GSK503, BIX 01294, SGC 0946 and a combination thereof.

In an embodiment, the histone demethylase inhibitor is selected from the group consisting of parnate(tranylcypromine), Tranylcypromine (2-PCPA)HCl, SP2509, 4SC-202, ORY-1001 (RG-6016), GSKJ1, GSK-LSD1 and a combination thereof.

In an embodiment, the JAK-STAT inhibitor is selected from the group consisting of STAT5-IN-1, JAK3-IN-1, JAK3-IN-7, WP1066, Homoharringtonine, Pyridone 6, Artesunate, SH-4-54, Baricitinib, Ruxolitinib phosphate, AG-490, Baricitinib phosphate, SAR-20347, CYT387 Mesylate, AS1517499, Peficitinib, Ruxolitinib sulfate, NSC 74859, Stattic, Tofacitinib citrate, Pimozide, Oclacitinib maleate, Ruxolitinib, S-enantiomer, SB1317, Niclosamide, Scutellarin, Solcitinib, Mogrol, Nifuroxazide, TG101348 (SAR302503), AG-1478 (Tyrphostin AG-1478) (EGFR inhibitor), KX2-391 (Src inhibitor), PKI-402 (PI3Kα/β/γ/δ and mTOR inhibitor), NSC 74859 (S3I-201) (STAT3inhibitor), Fludarabine (Fludara) (STAT-1 inhibitor), U0126-EtOH (UO126 EtOH) (MEK1 and MEK2 inhibitor), SGI-1776 free base (Pim1,Pim2 and Pim3 inhibitor), Sorafenib (Nexavar) (VEGFR, PDGFR, c-Raf and B-Raf inhibitor), PLX-4720 (B-RafV600E and c-Raf-1Y340D/Y341D inhibitor) and a combination thereof.

In an embodiment, the cytokine or recombinant protein combination is selected from the group consisting of PDGF, PDGFAA, PDGFAB, BMP4, IGF1, bFGF, EGF, VEGF, insulin, Activin A, TGF-beta1, Noggin, BMP-2, Shh, IL-6, CXCL10, CXCL12, CXCL2, HGF, IFN gamma, IL-2, IL-6R alpha, IL-2R alpha, TNF-alpha, TNF-beta, TPO, IGF2, IGFBP5, IGFBP6, IGFBP4, IGFBP7, IGFBP9, PDGF-BB, MMP3, GDF11, TIMP2 and a combination thereof.

In an embodiment, the gene editing involves the use of crispr/cas9 and TALEN gene editing to upregulate or knock out a gene or protein target involved in the JAK-STAT signaling pathway, such as STAT5A.

In an embodiment, the transgenic technique involves the use of lentivirus or retrovirus to overexpress or inhibit a gene or protein target in the JAK-STAT signaling pathway, such as STAT5A.

In an embodiment, in the rejuvenated and regenerative fibroblasts prepared by the above method, the JAK-STAT signaling pathway is inhibited, where the gene or protein target involved therein that experiences low expression or inhibited expression is SOS1, STAT5B, JAK1, JAK3, SOCS3, IL6ST, STAT1, STAT2, STAT3, STAT4, STAT6, STAT5A, IRF9, IL6, IL6R, IL2, IL2A, IL2B, PRKCD, CXCL12, CXCR4, JAK2, IL15RA, IL20RB, GHR, CXCL2, PRLR or a combination thereof.

In an embodiment, the rejuvenated and regenerative fibroblasts prepared by the above method suffer inhibition of the NOD-like receptor, and/or inhibition of the TGF-β receptor signaling pathway, and/or down-regulation of the insulin signaling pathway, and/or up-regulation of the WNT signaling pathway, and/or down-regulation of the notch signaling pathway and/or down-regulation of the p53 signaling pathway.

In an embodiment, the rejuvenated and regenerative fibroblasts are derived from normal fibroblasts, where the normal fibroblasts are derived from connective tissues (such as blood, skin, bone marrow, heart, blood vessel, muscle, urine, liver, kidney, digestive tract, lung, bone, cartilage, adipose, placenta and umbilical cord) of mammals (such as human, monkey, mouse, pig, rat, dog, cattle, sheep, goat, chicken, horse, tree shrew and rabbit).

In an embodiment, the rejuvenated and regenerative fibroblasts are prepared by treating normal fibroblasts with a combination of small molecule compounds, where the combination of small molecule compounds comprises at least one of a Jak-Stat inhibitor, a WNT/β-catenin agonist, a histone deacetylase inhibitor and a cAMP agonist.

In an embodiment, the rejuvenated and regenerative fibroblasts are prepared in the presence of at least one of a RAR agonist, a DNMT inhibitor, a HMT inhibitor, a histone demethylase inhibitor, ascorbate, a JNK inhibitor, a PKC inhibitor, a ROCK inhibitor and a TGF-β inhibitor.

In an embodiment, the rejuvenated and regenerative fibroblasts are prepared in a stagewise manner respectively using a first composition and a second composition, where the first composition consists of a WNT/β-catenin agonist, a histone deacetylase inhibitor and a CAMP agonist, or consists of a histone deacetylase inhibitor, an inhibitor of TGF-β receptor, a WNT/β-catenin agonist and a cAMP agonist; the second composition comprises a histone deacetylase inhibitor, a TGF-β inhibitor, a WNT/β-catenin agonist, a cAMP agonist, a RAR agonist, a HMT inhibitor, ascorbate, a PKC inhibitor and a ROCK inhibitor.

In an embodiment, the preparation method involves the use of at least one of 0.05-10 mM VPA, 1-15 μM CHIR99021, 0.5-10 μM Repsox, 3-50 μM Forskolin, 1-20 μM Go 6983, 1-25 μM Y-27632, 0.02-1 μM AM580, 0.5-15 μM EPZ004777, 0.2 mM Vc, 0.2-20 μM TTNPB, 1-15 μM 5-Azacytidine and 1-50 μM SP600125. In an embodiment, the normal fibroblasts are first treated with the first composition for 2-10 days, where the first composition consists of 0.05-10 mM of VPA, 1-15 UM of CHIR99021, 0.5-10 μM of Repsox and 3-50 μM of Forskolin, and then the fibroblasts are with the second composition for 4-20 days, where the second composition consists of 0.05-10 mM of VPA, 1-15 μM of CHIR99021, 0.5-10 μM of Repsox, 3-50 μM of Forskolin, 1-20 μM of Go 6983, 1-25 μM of Y-27632, 0.02-1 μM of AM580, 0.5-15 μM of EPZ004777, 0.2 mM of Vc and 0.2-20 μM of TTNPB.

In an embodiment, compared to the normal fibroblasts, the telomere of the rejuvenated and regenerative fibroblasts is extended by 1.5 to 12 times, and is close to the cells of the same type in minor individuals in length. Other cells (such as osteoblasts and chondrocytes) derived from the rejuvenated and regenerative fibroblasts have longer telomeres and stronger functional activity than similar cells from the same individual.

In an embodiment, products (such as secretion and lysate) derived from the rejuvenated and regenerative fibroblasts are applied to the construction of tissue engineering materials and the delaying or reversing of the aging of cells, tissues, organs and the body.

In a second aspect, this application provides an application of the rejuvenated and regenerative fibroblasts in the construction of tissue engineering materials and the delaying or reversing of the aging of cells, tissues, organs and the body.

In an embodiment, the rejuvenated and regenerative fibroblasts are prepared by knocking out STAT5 gene from normal fibroblasts.

In an embodiment, the rejuvenated and regenerative fibroblasts with extended telomere are obtained 3-100 days after the STAT5 gene is knocked out from normal fibroblasts.

In an embodiment, rejuvenated mesenchymal stem cells are prepared by treating mesenchymal stem cells with a combination of small molecule compounds or by gene editing, where the combination of small molecule compounds comprises at least one of a Jak-Stat inhibitor, a WNT/β-catenin agonist, a DNMT inhibitor, a TGF-β inhibitor and a cAMP agonist, and the gene editing is performed by knocking out a gene or protein target in the Jak-Stat signaling pathway (such as STAT5A).

In an embodiment, the mesenchymal stem cells are treated with a combination of 1-15 μM of CHIR99021 and 1-15 μM of 5-Azacytidine (AZA), a combination of 1-15 μM of AZA and 3-50 μM of Forskolin or a combination of 1-15 μM of AZA, 3-50 μM of Forskolin and 1-15 μM of CHIR99021 for 1-28 days for rejuvenation.

In a third aspect, this application provides an application of the rejuvenated and regenerative fibroblasts or a culture or lysate thereof in the manufacture of a kit, a drug, a healthcare product, food, cosmetics or a medical device.

In a fourth aspect, this application provides use of the rejuvenated and regenerative fibroblasts as seed cells or scaffold sources in the preparation of tissue engineering materials, the repairing of damages of mammalian tissues and organs and the repairing of aged and degenerated tissues and organs.

In a fifth aspect, this application provides an application of the rejuvenated and regenerative fibroblasts in the medical research or in the preparation of an immunomodulator.

In a sixth aspect, this application provides an application of the rejuvenated and regenerative fibroblasts in the in vitrolin vivo prevention, delaying and reversing of the aging process of mammalian tissues, organs and bodies.

In a seventh aspect, this application provides an application of the rejuvenated and regenerative fibroblasts in the reprogramming or rejuvenation of cells, tissues, organs and organisms.

In an eighth aspect, this application further provides a method of treating a bone and joint related disease, acute inflammation, degenerative changes of digestive tracts, aging syndrome or skin defect in a patient in need thereof, comprising:

administering the rejuvenated and regenerative fibroblasts prepared by the above method to the patient.

In an embodiment, the bone and joint related disease is bone defect, cartilage defect or osteoporosis; and the administration of the rejuvenated and regenerative fibroblasts is performed by local transplantation or intravenous injection.

The features of this application are specifically described as follows. By means of regulating the gene or protein targets in the Jak-Stat signaling pathway quantitatively and/or in a timing manner, the cell differentiation, dedifferentiation, transdifferentiation, rejuvenation, aging and apoptosis can be regulated and the aging process can be reversed to extend the lifespan of the body, where the regulation of the gene or protein targets in the Jak-Stat signaling pathway is performed using a combination of small molecule compounds, a cytokine combination, a recombinant protein combination, gene editing or transgenic technique. The gene or protein targets are selected from the group consisting of CXCL2, SOS1, STAT5B, JAK1, JAK3, SOCS3, IL6ST, STAT1, STAT2, STAT3, STAT4, STAT6, STAT5A, IRF9, IL6, IL6R, IL2 (e.g., IL2A and/or IL2B), PRKCD, CXCL12, CXCR4, JAK2, IL15RA, IL20RB, GHR, PRLR and a combination thereof. The combination of small molecule compounds includes at least one of a Jak-Stat inhibitor, a WNT/β-catenin agonist, a histone deacetylase inhibitor, a cAMP agonist, a RAR agonist, a DNMT inhibitor, an HMT inhibitor, a histone demethylase inhibitor, ascorbate, a JNK inhibitor, a PKC inhibitor, a ROCK inhibitor and a TGF-β inhibitor. The cytokine combination or the recombinant protein combination is selected from the group consisting of PDGF, PDGFAA, PDGFAB, BMP4, IGF1, bFGF, EGF, VEGF, insulin, Activin A, TGF-beta1, Noggin, BMP-2, Shh (Sonic Hedgehog), IL-6, CXCL10, CXCL12, CXCL2, HGF, IFN gamma, IL-2, IL-6R alpha, IL-2R alpha, TNF-alpha, TNF-beta, TPO, IGF2, IGFBP5, IGFBP6, IGFBP4, IGFBP7, IGFBP9, PDGF-BB, MMP3, GDF11 and TIMP2. The gene editing involves the use of crispr/cas9 gene editing to up-regulate or knock out gene or protein targets in the JAK-STAT signaling pathway, such as STAT5A. The transgenic technique involves the use of lentivirus or retrovirus to overexpress or inhibit gene or protein targets in the JAK-STAT signaling pathway, such as STAT5A.

This application employs a combination of small molecule compounds to inhibit the gene or protein targets in the JAK-STAT signaling pathway (such as STAT5A and JAK1) in fibroblasts to prepare the rejuvenated and regenerative fibroblasts, in which the JAK-STAT signaling pathway is inhibited. Moreover, the rejuvenated and regenerative fibroblasts also experience inhibition of NOD-like receptor signaling pathway, inhibition of TGF beta receptor signaling pathway, down-regulation of the insulin signaling pathway, up-regulation of the WNT signaling pathway, down-regulation of the notch signaling pathway, down-regulation of the p53 signaling pathway or a combination thereof. Compared to the normal fibroblasts, the telomere of the rejuvenated and regenerative fibroblasts is extended by 1.5 to 12 times, and is close to the cells of the same type in minor individuals in length. Other cells (such as osteoblasts and chondrocytes) derived from the rejuvenated and regenerative fibroblasts have longer telomeres and stronger functional activity than similar cells from the same individual. The rejuvenated and regenerative fibroblasts and the secretion and lysate derived therefrom can be applied to the construction of tissue engineering materials and the delaying or reversing of the aging of cells, tissues, organs and bodies.

This application employs the quantitative and/or timing regulation of gene or protein targets in the Jak-Stat signaling pathway to regulate cell differentiation, dedifferentiation, transdifferentiation, rejuvenation, aging and apoptosis, and reverse the aging process to prolong the lifespan, which can promote the transdifferentiation among different types of cells, facilitate the preparation of different types of rejuvenated cells (such as rejuvenated mesenchymal stem cells and super fibroblasts) and promote cell senescence and apoptosis. The rejuvenated and regenerative fibroblasts prepared by the method of the invention and the secretion and lysate thereof can be applied in the in vitrolin vivo prevention, delaying and reversing of the aging of mammalian tissues, organs and bodies, the reprogramming of the cells, tissues, organs and bodies and the repairing of the injured, aged and degenerated mammalian tissues and organs, and can also be used as seed cells and scaffold sources for the tissue engineering materials.

The mechanism of the invention is described as follows. The expression of gene or protein targets in the Jak-Stat signaling pathway in cells is regulated quantitatively and/or in a timing manner to differently regulate the metabolic pathways, changing the cell state of the target cell to allow it to transform into other cells or to possess different cell characteristics.

Compared to the prior art, this application has the following beneficial effects.

Compared to the fibroblasts derived from the same donor or the fibroblasts derived from a different donor at the same age, the rejuvenated and regenerative fibroblasts are free of tumorigenicity. The rejuvenation of the rejuvenated and regenerative fibroblasts is characterized by the changes in epigenetics, and/or changes in the expression of senescence-related genes, and/or the extension of cell telomeres, and/or the acceleration of cell proliferation, and/or the ability to perform long-term stable passage. In addition, the rejuvenated and regenerative fibroblasts and products thereof can reverse the aging of the mammalian organisms and prolong the lifespan. The quantitative and/or timing regulation of gene or protein targets in the Jak-Stat signaling pathway provided herein can systematically regulate the cell differentiation, dedifferentiation, transdifferentiation, rejuvenation, aging and apoptosis, and the resulting rejuvenated and regenerative fibroblasts and products therefrom can be used in the vitro/in vivo prevention, delaying and reversing of the aging of mammalian tissues, organs and bodies, the reprogramming of the cells, tissues, organs and bodies and the repairing of the injured, aged and degenerated mammalian tissues and organs, and can also be used as seed cells and scaffold sources for the tissue engineering materials.

BRIEF DESCRIPTION OF THE DRAWINGS

FIG. 5A: fold change of mRNA of JAK1 and STAT5; FIG. 5B: gene expression of TERT; FIG. 5C: relative telomere length.

FIG. 7A: staining H3K9me3 and H4K20me3 with DAPI; FIG. 7B: staining γH2AX with DAPI; and FIG. 7C: number of γH2AX foci per cell.

DETAILED DESCRIPTION OF EMBODIMENTS

Example 1 Preparation and Characterization of Rejuvenated and Regenerative Fibroblasts 1. Human skin fibroblasts were seeded onto a 6-well plate and cultured in a Fib culture medium for 24 hours.

2. The cell culture medium was replaced with an induction culture medium containing a cocktail (Mix V) of small molecules, and then the medium was replaced every 2 days.

3. After cultured in the induction culture medium containing Mix V for 5 days, the skin fibroblasts were transferred to an induction culture medium containing Mix P, and the medium was replaced every 2 days.

4. After cultured in the induction culture medium containing Mix P for 7 days, the skin fibroblasts were transferred to a HG (high glucose)-DMEM containing 10% FBS, 10 ng/ml of bFGF, 100 ng/ml of PDGF-AB and 10 ng/ml of BMP4 or merely containing 10% FBS, or to a rFib medium for culture. After cultured for another 3 days, the cells were subjected to long-term passage and characterization.

5. During the long-term passage, the rFibs were cultured in a MSC basal medium and subcultured when the confluency reached 90%.

The Fib culture medium was a HG-DMEM containing 10% FBS or a commercially-available FibStar medium (cat. no. FMS0030, rFib).

The Mix V was a HG-DMEM supplemented with 10% FBS, or a commercially-available FibGro medium (cat. no. FGS0040, rFib) containing 0.5 mM of VPA, 3 µM of CHIR99021, 1 µM of Repsox and 10 UM of Forskolin.

The Mix P was a HG-DMEM supplemented with 10% FBS or a commercially-available FibGro medium (cat. no. FGS0040, rFib), containing 0.5 mM of VPA, 3 µM of CHIR99021, 1 µM of Repsox, 10 µM of Forskolin, 10 µM of SP600125, 5 µM of Go 6983, 5 µM of Y-27632, 0.05 µM of AM580, 5 µM of EPZ004777, 0.2 mM of Vc and 5 µM of TTNPB.

The MSC basal medium was LG-DMEM supplemented with 10% FBS, or a commercially-available complete medium for bone marrow mesenchymal stem cells (cat. no. HUXMA-90011, Cyagen) or a commercially-available rFib medium (cat. no. CRM0016-01, rFib).

It should be noted that unless otherwise specified, the cells used in the examples are derived from human.

Figure 1:
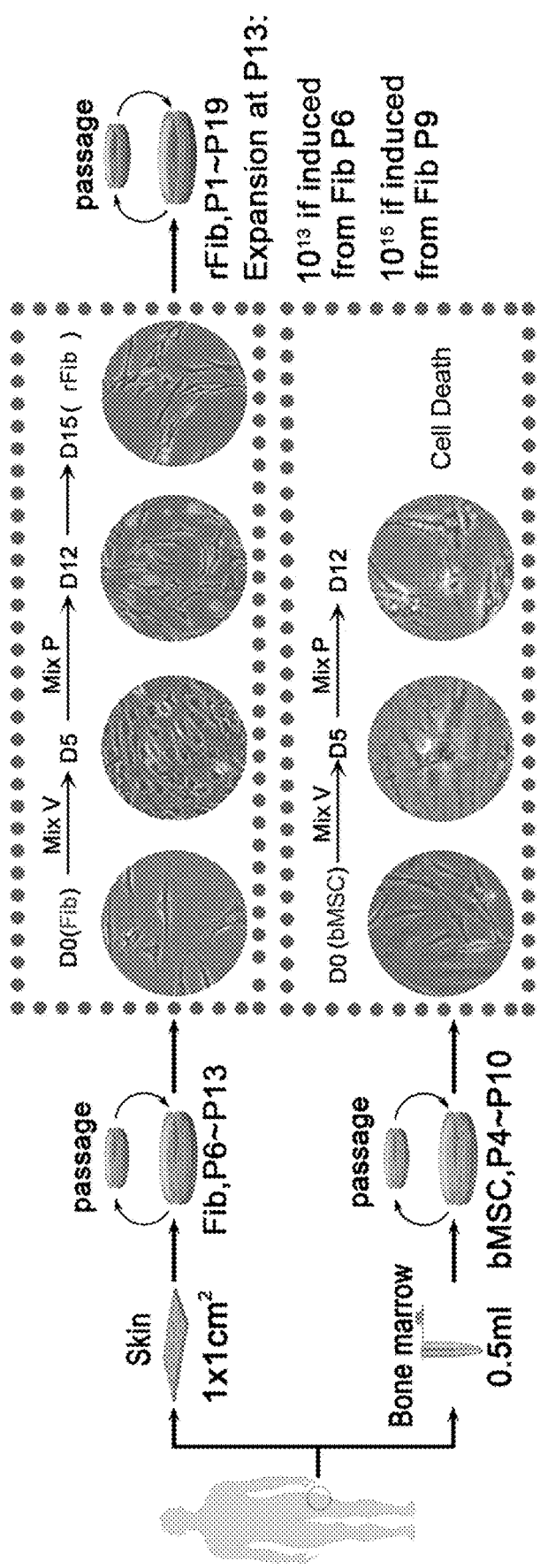
FIG. 1 schematically shows the preparation of regenerative fibroblasts (rFib) from fibroblasts (Fib).

FIG. 1 schematically showed the preparation of rFib from Fib, from which it can be seen that the Fib close to senescence (P13) gain tremendous growth potential (can experience another at least 19 passages) after conversion, while the same treatment process induced the death of bone marrow mesenchymal stem cells.

Figure 2:
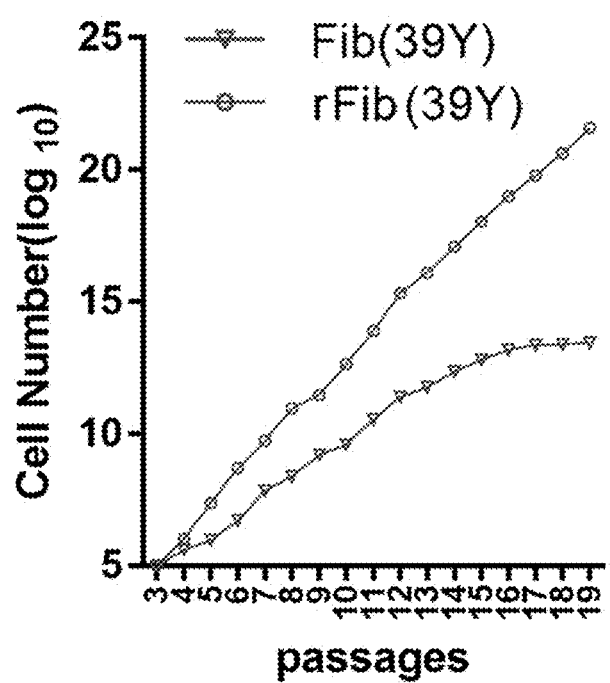
FIG. 2 illustrates growth curves of rFib and its parental Fib during the long-term expansion.

FIG. 2 illustrated growth curves of rFib and its parent Fib during the long-term expansion, in which rFib presented a better growth rate than the parent Fib.

Figure 3:
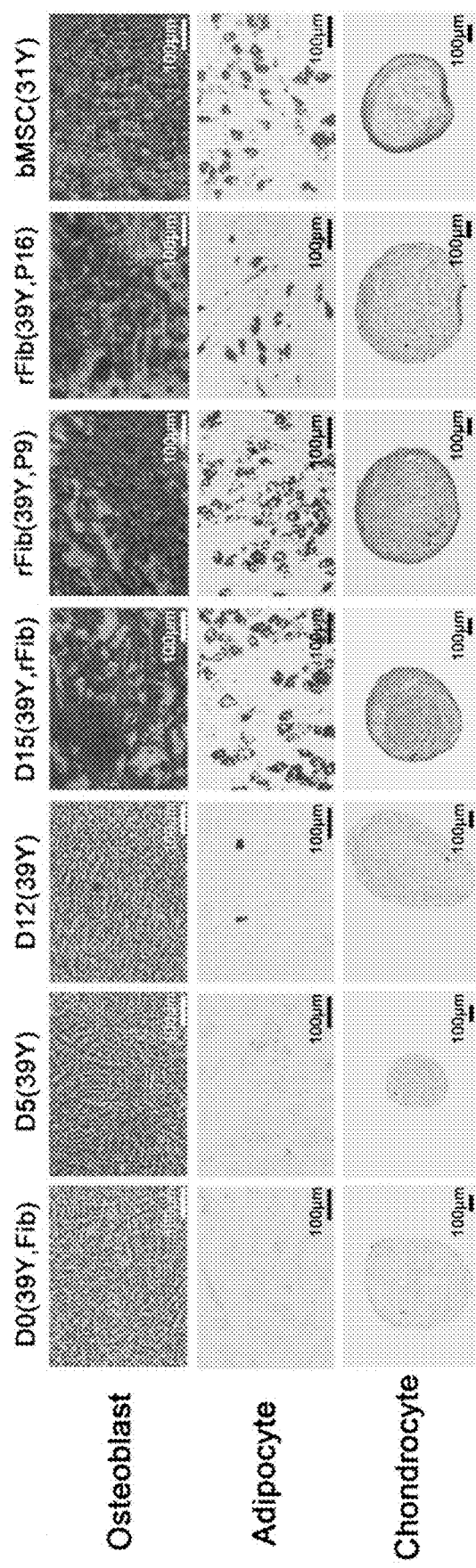
FIG. 3 illustrates histochemical assay results of differentiation potentials of Fib and rFib.

FIG. 3 showed histochemical analysis of osteogenesis, chondrogenesis and adipogenesis differentiation before and after conversion (parental Fib were at P8 from a 39-year-old donor). Samples at D0 (Fib, before treatment), D5, D12, D15 (rFibs), and after serial passaging were examined. After 21 days of the induction, the differentiated osteoblasts, adipocytes and chondrocytes were identified by staining respectively with alizarin red, oil red and alician blue. Moreover, the staining results also demonstrated that after passaged several times (9 and 16), the rFib still maintained desirable differentiation potentials.

Figure 4:
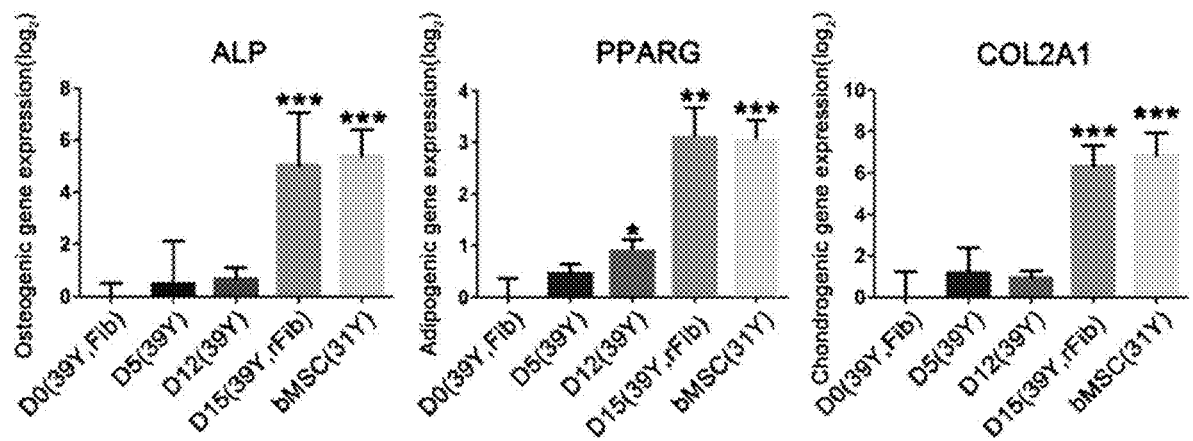
FIG. 4 shows the expression levels of osteogenic gene ALP, adipogenic gene PPARG and chondrogenic gene COL2A1 in Fib and rFib.

FIG. 4 showed the expression levels of ALP (14 days after induced osteogenic differentiation), COL2A1 (14 days after induced chondrogenic differentiation) and PPARG (21 days after induced adipogenic differentiation) were analyzed by q-RT-PCR, and the results revealed that similar to young bMSCs, the rFibs can also highly express genes related to trilineage differentiation (*$p<0.05$, $p<0.01$, *$p<0.001$, $n>3$, the significance analysis was performed by comparison with D0(Fib)).

Figure 5A:
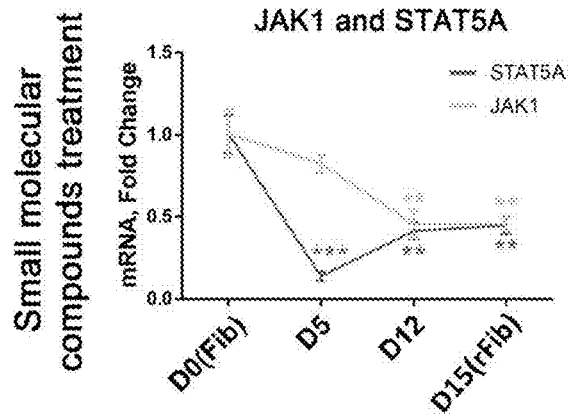
FIGS. 5A-5C show changes of expression levels of JAK1, STAT5 and telomerase reverse transcriptase (TERT) and change of telomere length over time after fibroblasts are treated with small molecular compounds, where
Figure 5B:
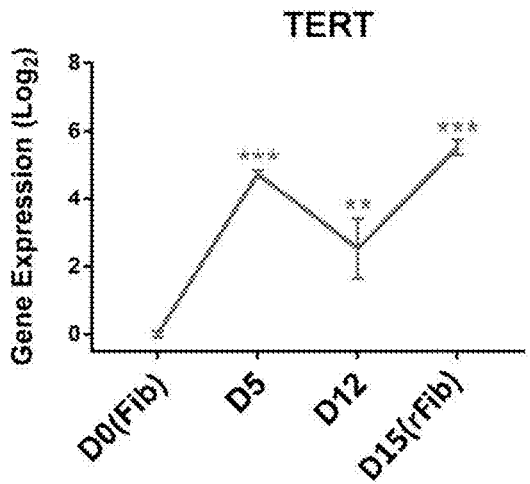
Figure 5C:
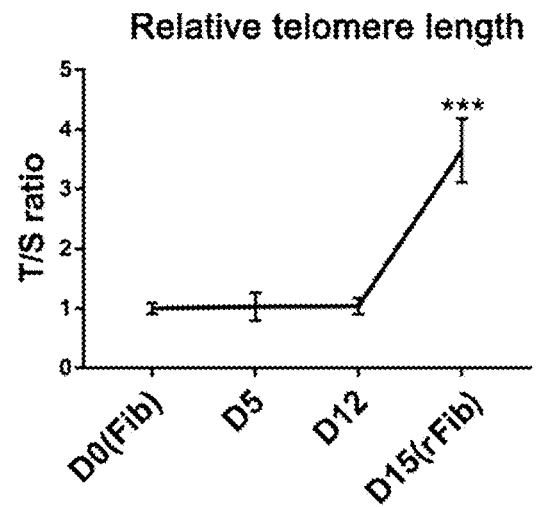

FIGS. 5A-C showed changes of expression levels of JAK1, STAT5 and telomerase reverse transcriptase (TERT) and change of telomere length over time after fibroblasts were treated with small molecular compounds, from which it can be observed that the treatment brought a decrease in the expression levels of JAK1 and STAT5; the TERT experienced high expression on the 5$^{th}$ day of the treatment; and the telomere was significantly extended on the 15$^{th}$ day of the treatment.

Figure 6:
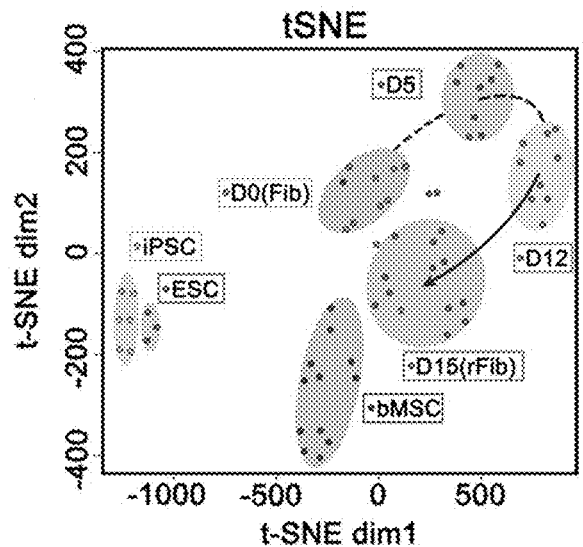
FIG. 6 shows cluster analysis results of transcriptome data of Fib, rFib, iPSC, ESC and bMSC.

FIG. 6 showed tSNE analysis of global gene expression in parental Fib, D5 & D12 cells, D15 rFibs, and bMSCs, as well as hESCs and iPSCs. The results demonstrated that the rFib was more similar to Fib and bMSC relative to iPSC and ESC, which indicated that the rFib possessed the characteristics of mesenchymal stem cells. Moreover, unlike hESCs and iPSCs, the rFibs were safe and had no tumorigenicity.

As shown in FIGS. 7A-C, 8, 9A-C and 10, the rFib possessed rejuvenation-related characteristics compared to Fib and bMSC.

Figure 7A:
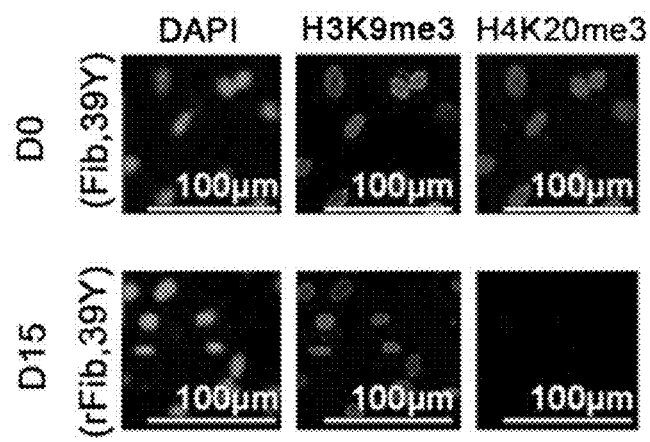
FIGS. 7A-7C show the immunofluorescence staining results of Fib and rFib, where

FIG. 7A displayed immunofluorescence staining results of senescence markers H3K9me3 and H4K20me3 in Fib (DO, passage 11 parental Fib) and rFib (D15), from which it can be concluded that the rFib had significantly reduced H4K20me3 compared with the parent Fib.

Figure 7B:
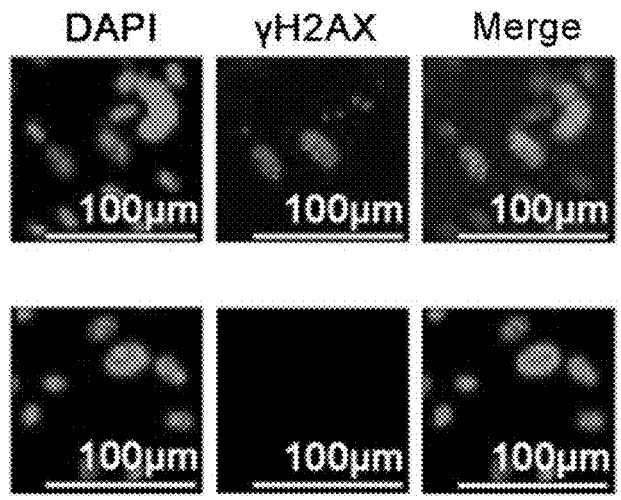
Figure 7C:
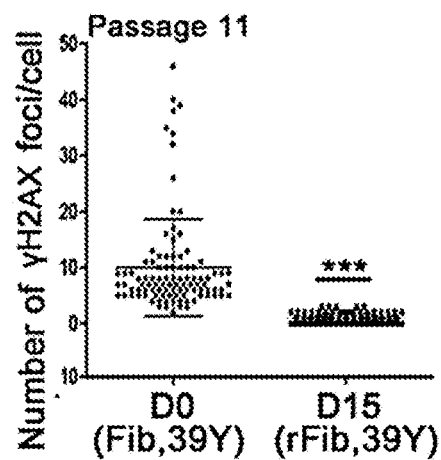

FIGS. 7B-C respectively displayed immunofluorescence staining result and quantification of senescence marker γH2AX in Fib (DO, passage 11 parental Fib) and rFib (D15), from which it can be concluded that the rFib had significantly reduced γH2AX compared with the parent Fib.

Figure 8:
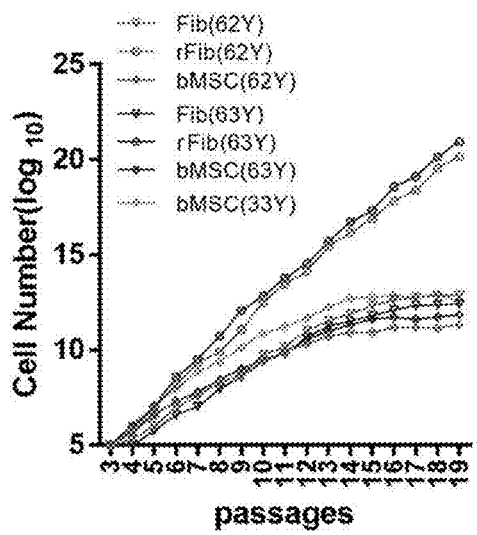
FIG. 8 shows growth curves of Fib, rFib and bMSC respectively derived from two old individuals during the long-term expansion.

FIG. 8 showed growth curves of Fib, rFib and bMSC respectively derived from two old volunteers during the long-term expansion, where the cells from the same donor were indicated by the same color. As illustrated in this figure, the rFib grew significantly faster than bMSC and Fib from the same donor, and the growth rate of the rFib from the elderly donor was even higher than that of the bMSC from the young donor (33 years old).

Figure 9A:
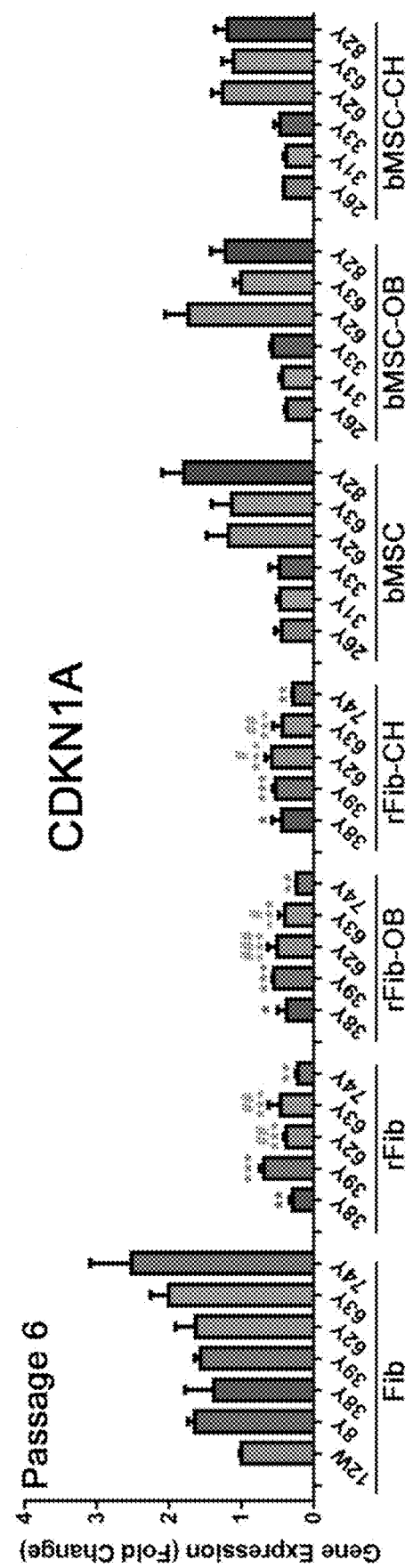
FIGS. 9A-9C show expression levels of several senescence markers respectively in Fib, rFib, rFib-OB, rFib-CH, bMSC, bMSC-OB and bMSC-CH, where 9A: CDKN1A; 9B: ATF3; and 9C: IL6.
Figure 9B:
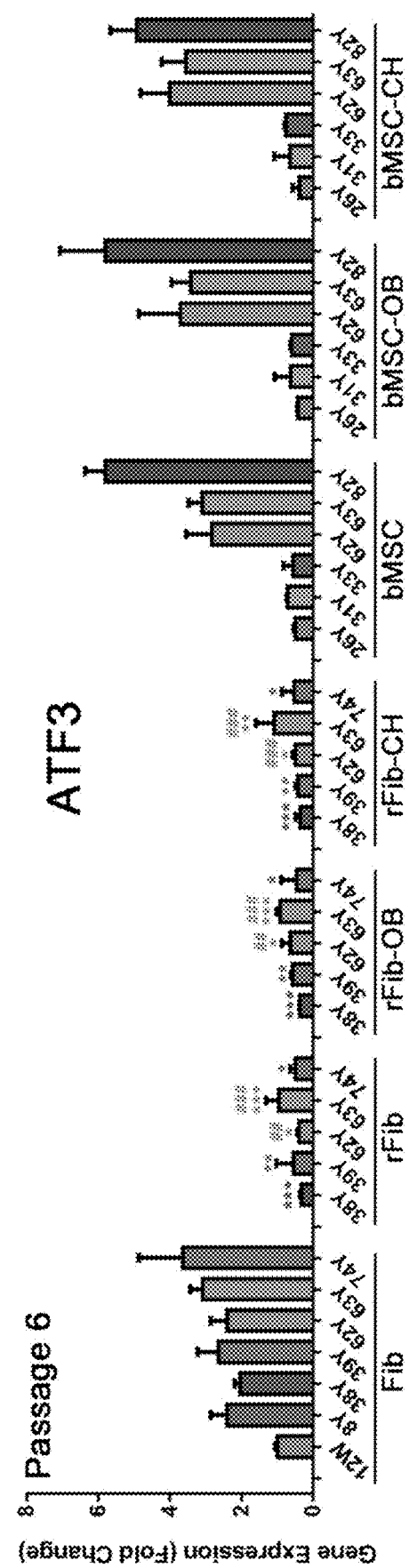
Figure 9C:
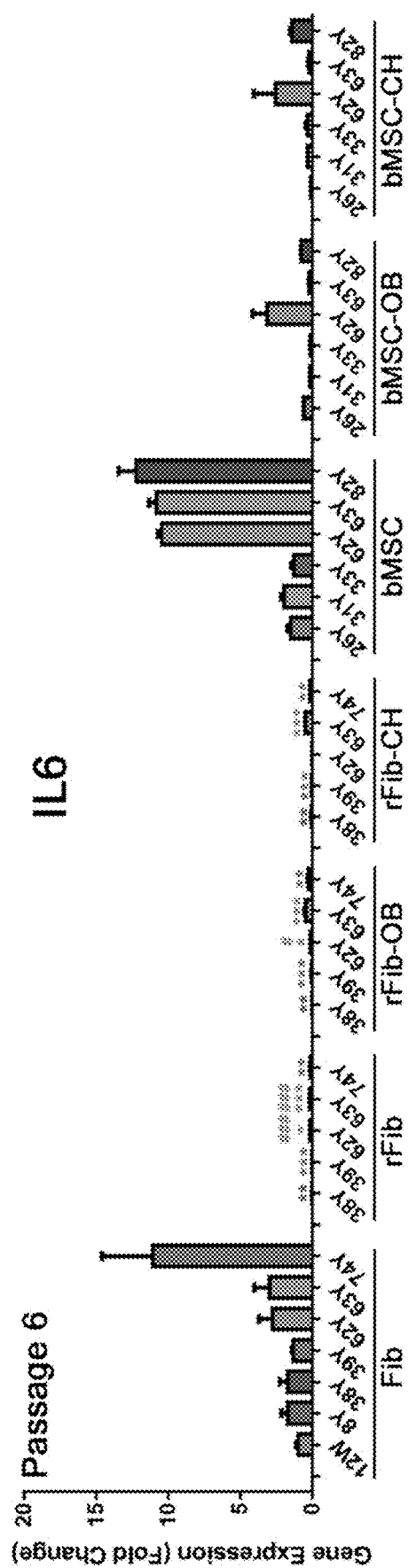

Expression levels of several senescence markers (CDKN1A, ATF3 and IL6) in Fib, rFib, rFib-OB, rFib-CH, bMSC, bMSC-OB and bMSC-CH were detected by q-RT-PCR (FIGS. 9A-C, where 12W indicated the skin fibroblast cells of the aborted embryo at 12$^{th}$ week of pregnancy). It was apparent that the rFibs and the osteoblasts and chondrocytes derived therefrom all experienced significantly reduced expression of such senescence markers.

Figure 10:
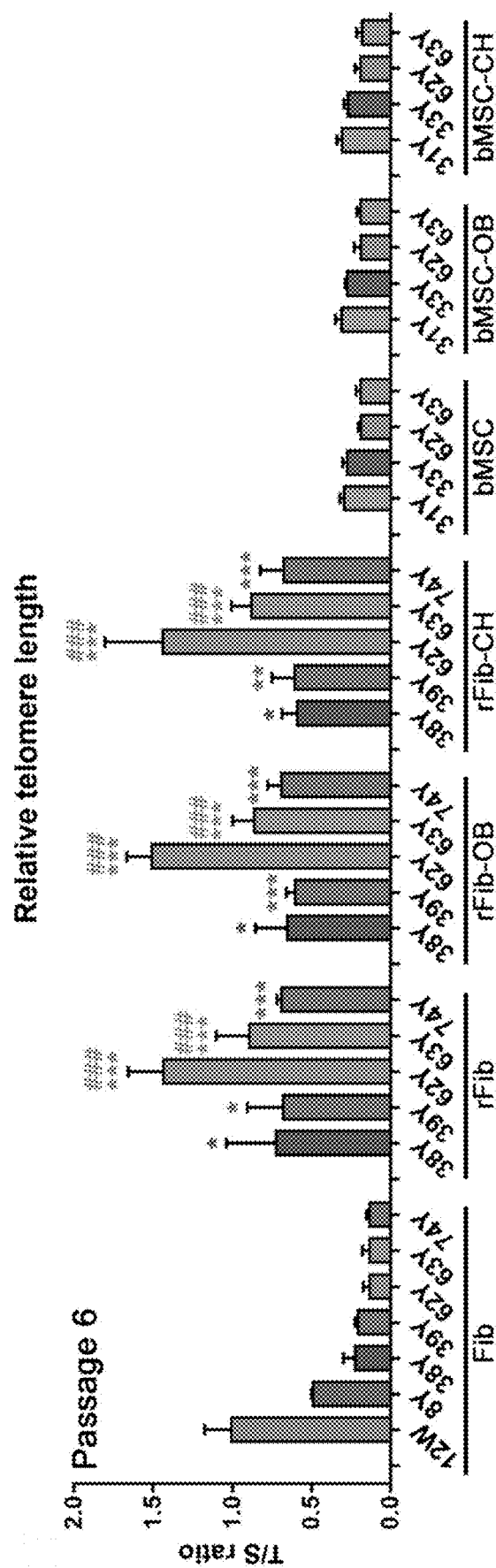
FIG. 10 illustrates the relative telomere length (expressed by T/S ratio) in Fib, rFib, rFib-OB, rFib-CH, bMSC, bMSC-OB and bMSC-CH.

The relative telomere length of Fib, rFib, rFib-OB, rFib-CH, bMSC, bMSC-OB and bMSC-CH was detected by q-RT-PCR and expressed by T/S ratio (FIG. 10).

In FIGS. 9A-C and 10, the cells from the same donor were indicated by the same color; * indicated significant difference when compared to homologous Fib; #indicated significant difference when compared to corresponding bMSC, bMSC-OB (osteoblasts derived from bMSC) and bMSC-CH (chondrocytes derived from bMSC); *p<0.05, p<0.01, *p<0.001, #p<0.05, ##p<0.01, ###p<0.001, n=3.

FIGS. 11-17 revealed that the osteogenic and chondrogenic differentiation abilities of aged bMSC were inferior to the rFib, and the rFib was free of tumorigenicity.

Figure 11:
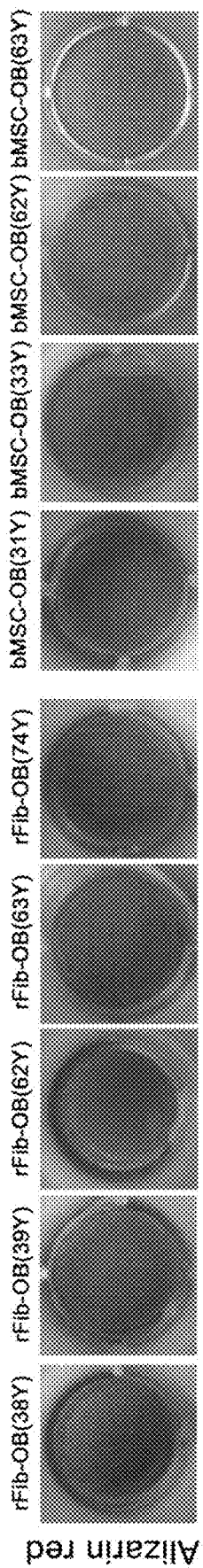
FIG. 11 depicts differentiated osteoblasts respectively derived from rFib and bMSC from individuals of different ages after stained with alizarin red.

After experiencing the osteogenic differentiation, the bMSC and rFib from donors of different ages were subjected to alizarin red staining, and the results were shown in FIG. 11. It can be found that the osteogenic differentiation potential of the bMSC from an elderly donor was greatly declined, while the rFib of the same elderly donor still maintained a desirable osteogenic differentiation ability.

Figure 12A:
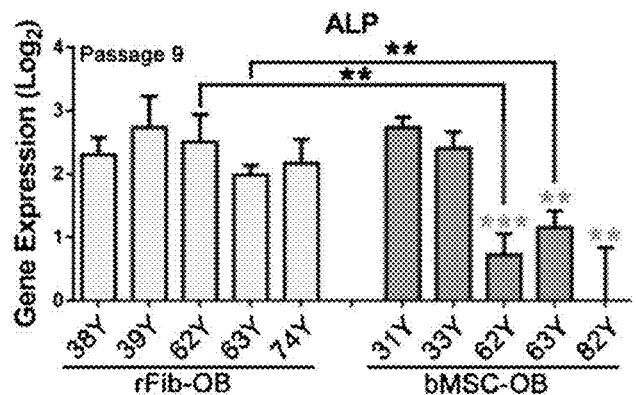
FIGS. 12A-C show expression levels of marker genes in osteoblasts respectively derived from rFib and bMSC from individuals of different ages, where 12A: ALP; 12B: OSX; and 12C: OPG.
Figure 12B:
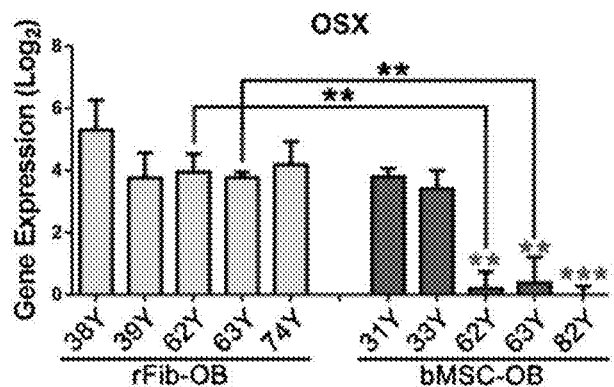
Figure 12C:
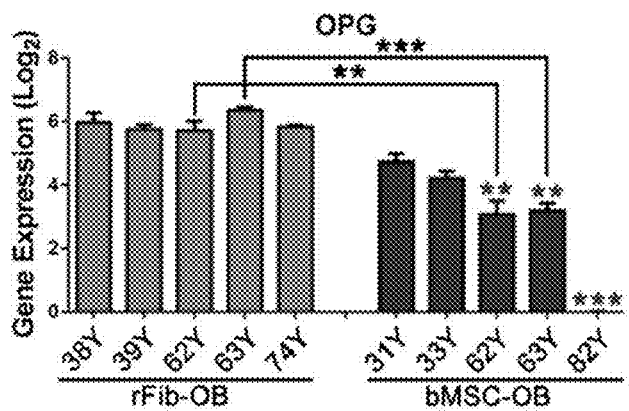

FIGS. 12A-C showed expression levels of marker genes in osteoblasts respectively derived from rFib and bMSC from volunteers of different ages, where the expression levels of ALP, OSX and OPG were all significantly higher in the rFib, while declined in bMSCs from elder individuals.

Figure 13:
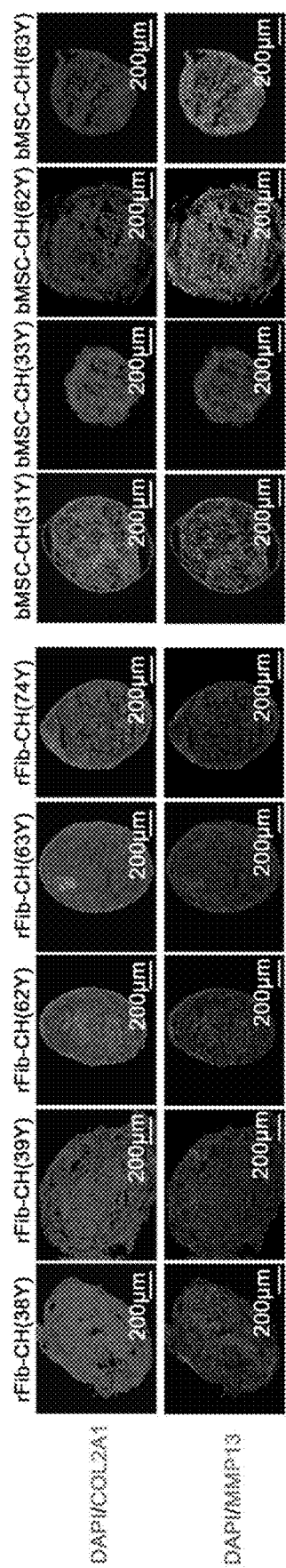
FIG. 13 shows COL2A1 and MMP13 in chondrocytes respectively derived from rFib and bMSC from individuals of different ages after immunofluorescence analysis.
Figure 14A:
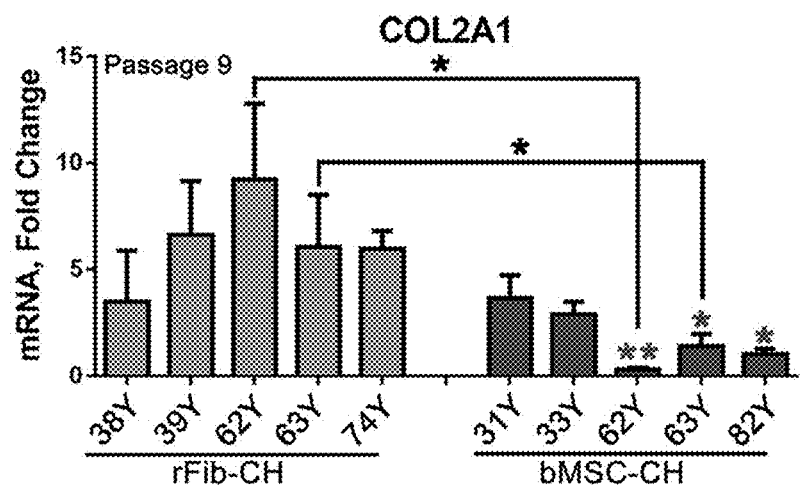
FIGS. 14A-B illustrate the expression of COL2A1 and MMP13 in chondrocytes respectively derived from rFib and bMSC from individuals of different ages, where 14A: COL2A1; and 14B: MMP13.
Figure 14B:
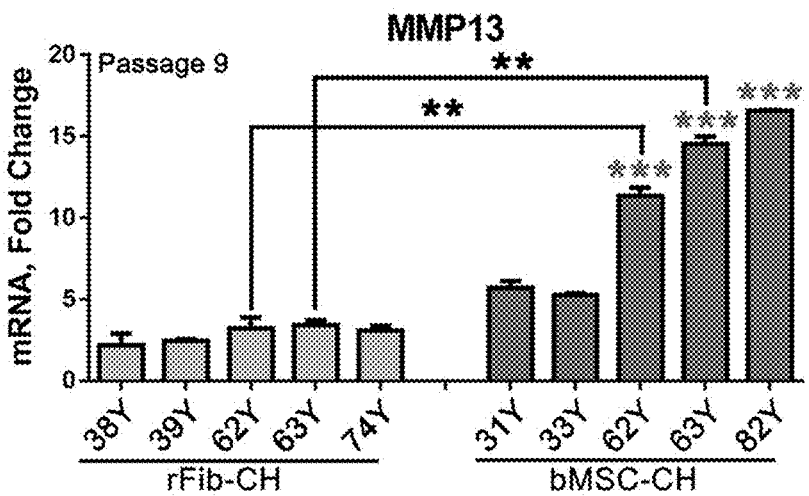

COL2A1 and MMP13 in chondrocytes respectively derived from rFib and bMSC from volunteers of different ages were subjected to immunohistochemical staining, and the results were exhibited in FIG. 13. The chondrocytes derived from bMSC from an elderly donor involved low expression of COL2A1 and high expression of MMP13, while chondrocytes derived from rFib from an elderly donor were similar to those derived from young rFib or bMSC in the expression of COL2A1 and MMP13.

Further, the expression levels of COL2A1 and MMP13 in chondrocytes respectively derived from rFib and bMSC from volunteers of different ages were analyzed by q-RT-PCR (FIGS. 14A-B), and the results were consistent with the staining results presented in FIG. 13.

Figure 15:
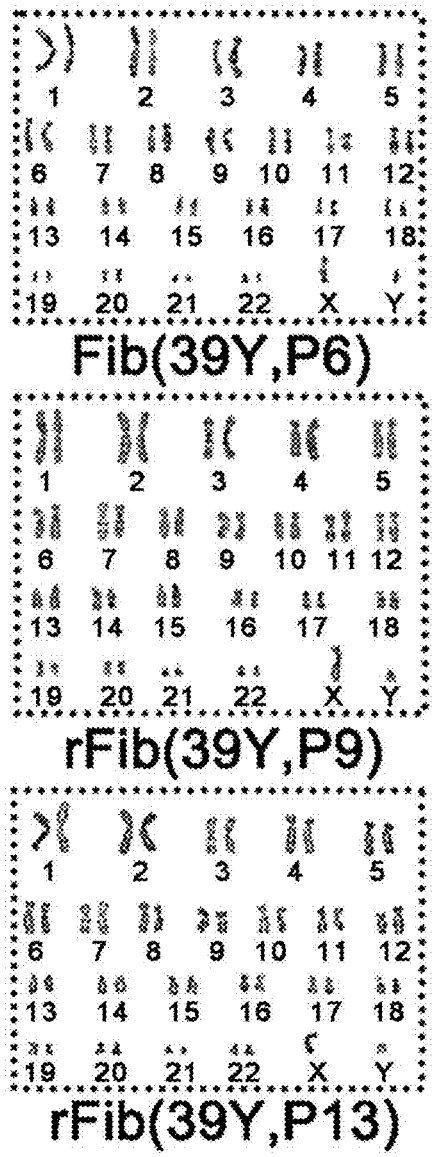
FIG. 15 shows karyotype analysis results of passage 9 rFib, passage 13 rFib and their parent passage 6 Fib.

FIG. 15 depicted the karyotype analysis results of passage 9 rFib, passage 13 rFib and their homologous passage 6 Fib, from which it can be observed that the karyotype of rFib remained consistent with its parental Fib even after long-term passage.

Figure 16:
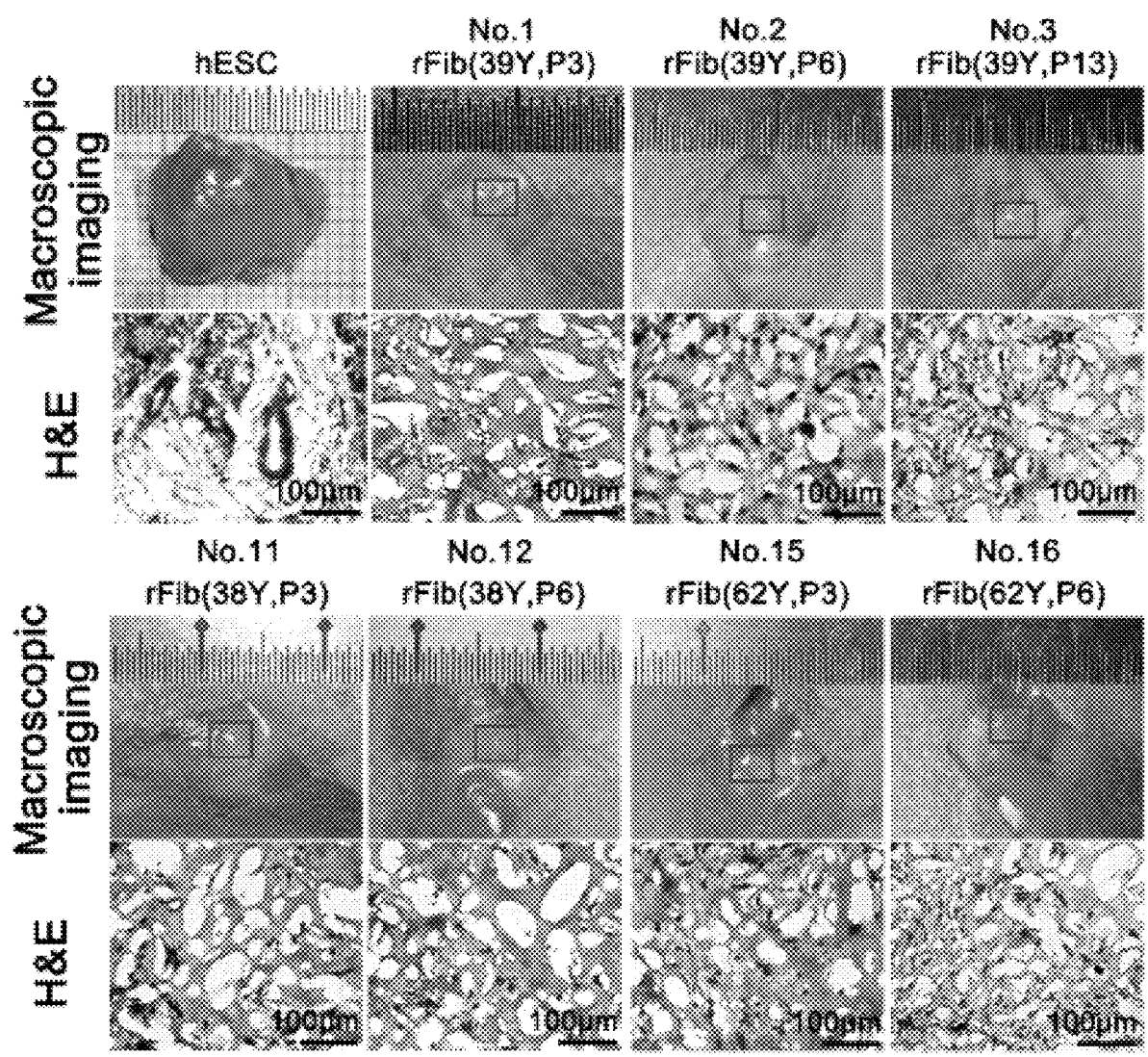
FIG. 16 shows teratoma formation assay of rFibs and hESC in NOD/SCID mice.

The tumorigenicity of rFib was tested by teratoma formation assay, and the results were shown in FIG. 16, where human embryonic stem cells (hESC) were used as positive control. As illustrated in FIG. 16, the subcutaneous transplantation of hESC resulted in the occurrence of teratomas (with obvious three-germ structure) in the NOD/SCID mice, while no tumors were found in mice transplanted with rFib.

Figure 17:
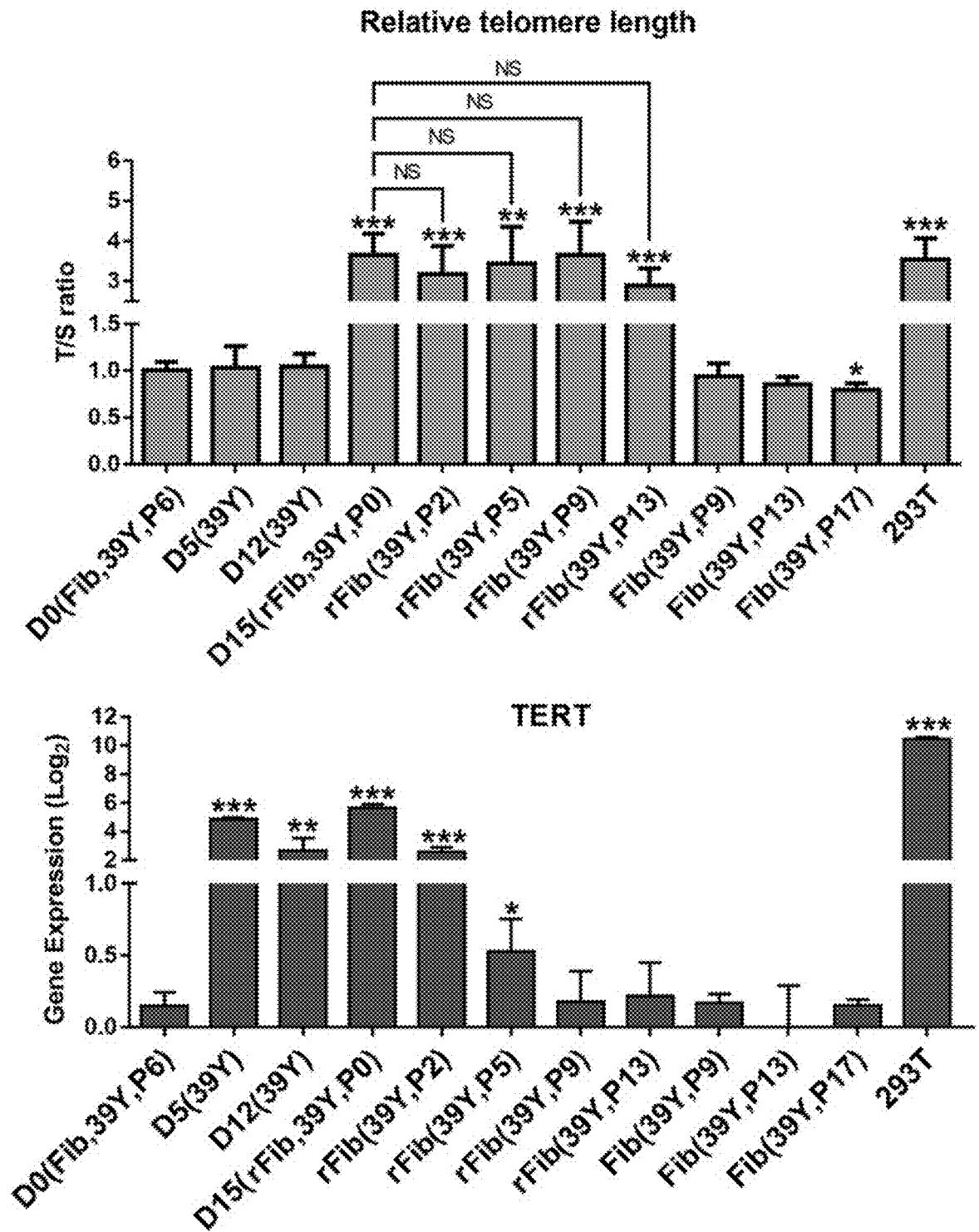
FIG. 17 illustrates the relative telomere length and expression level of TERT respectively in Fib and rFib.

FIG. 17 illustrated the relative telomere length and expression level of TERT in Fib and rFib, where compared with its homologous Fib, the rFib had significantly longer telomere length. However, in the rFib, the TERT only temporarily exhibited expression during the induction and then returned to a low expression level or no expression, which was different from tumor cells (the TERT experienced persistent high expression), indicating that the rejuvenation process will not bring tumorigenicity in the rFib.

6.1 In Vitro Immunomodulation Test

The Fib, rFib and bMSC were treated with mitomycin C for 2.5 hours, digested and counted, and then respectively seeded onto a 24-well plate at 1×10$^5$ cells/well. T lymphocytes were stained with carboxyfluorescein succinimidyl ester (CFDA-SE) at 37° C. for 30 min and then seeded onto the 24-well plate at 2×10$^5$ cells/well. PHA (Lectin from *Phaseolus vulgaris*) was added at a final concentration of 2 μg/mL to stimulate the proliferation of lymphocytes. Three experimental groups (bMSC+T+PHA group, rFib+T+PHA group and Fib+T+PHA group), a positive control group (T+PHA) and a negative control group (T alone) were set, and after co-cultured for 5 days, the T cells in each well were collected and washed with PBS three times. The proliferation of T lymphocytes was examined using anti-CD3, CD4 and CD8 antibodies (BD biosciences) by flow cytometry.

FIGS. 18, 19A-B and 20A-B showed that the rFib had in vitro immunomodulatory activity.

Figure 18:
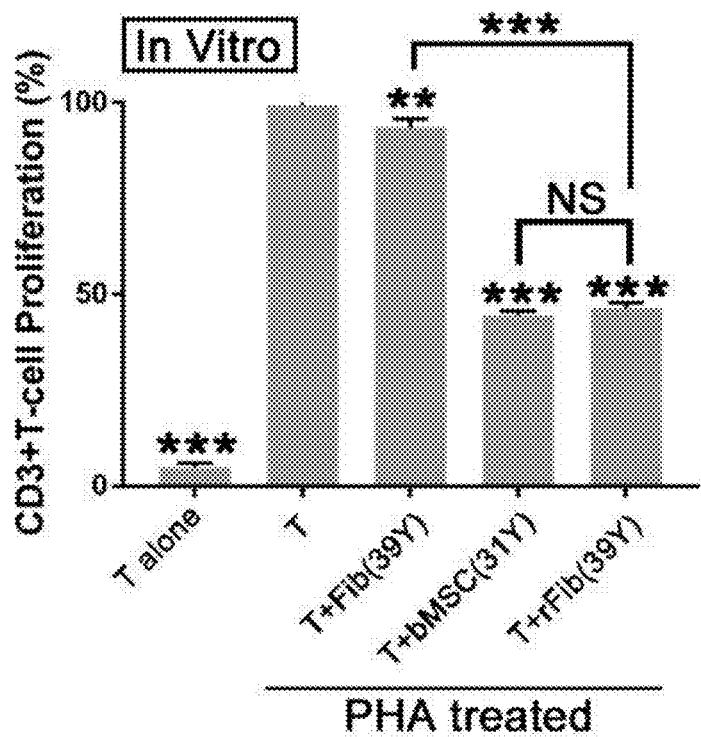
FIG. 18 shows a proliferation rate of CD3+ T cells when cultured alone or in combination respectively with Fib, bMSC and rFib.

Parental Fib, rFib and bMSC were respectively co-cultured with T cells according to the mixed lymphocyte reaction method, and the proliferation rate of T cells in each group was detected and the results were shown in FIG. 18 (p<0.01; *p<0.001; n=3; the significance analysis was performed by comparison with the "T+PHA" group). Peripheral blood mononuclear cells (PBMC) from a healthy volunteer were labeled with CFSE. The results demonstrated that the rFib was able to inhibit the proliferation of T cells, while its homologous Fib cannot inhibit the proliferation of T cells, indicating that the rFib had immunomodulatory function.

Figure 19A:
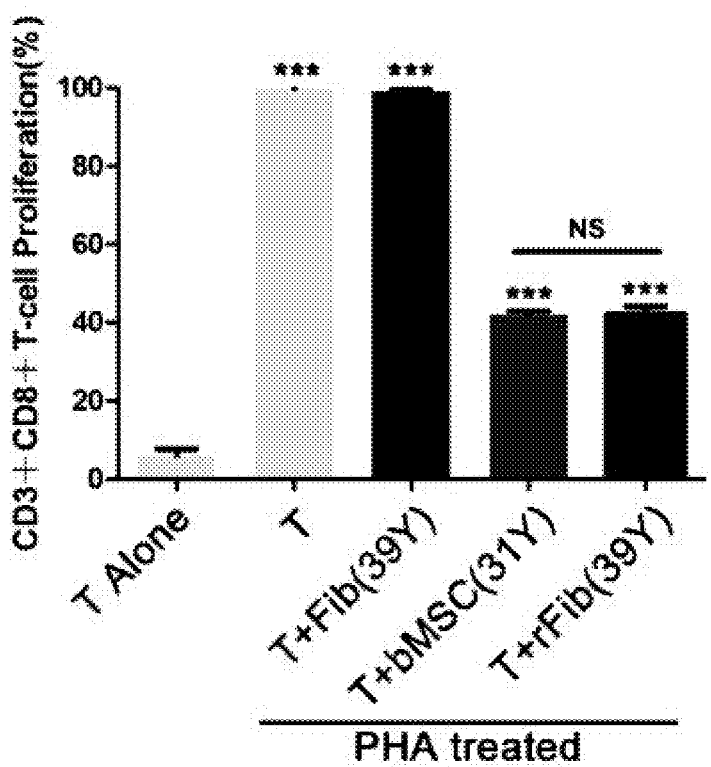
FIGS. 19A-B immune suppression of CD3+ CD8+ T cells by rFibs in mixed lymphocyte reaction assay, where 19A: a proliferation rate of CD3+ CD8+ T cells; and 19B: CD8+ T cells proliferation analysis for CFSE staining by flow cytometry gated on CD8+ T cells.
Figure 19B:
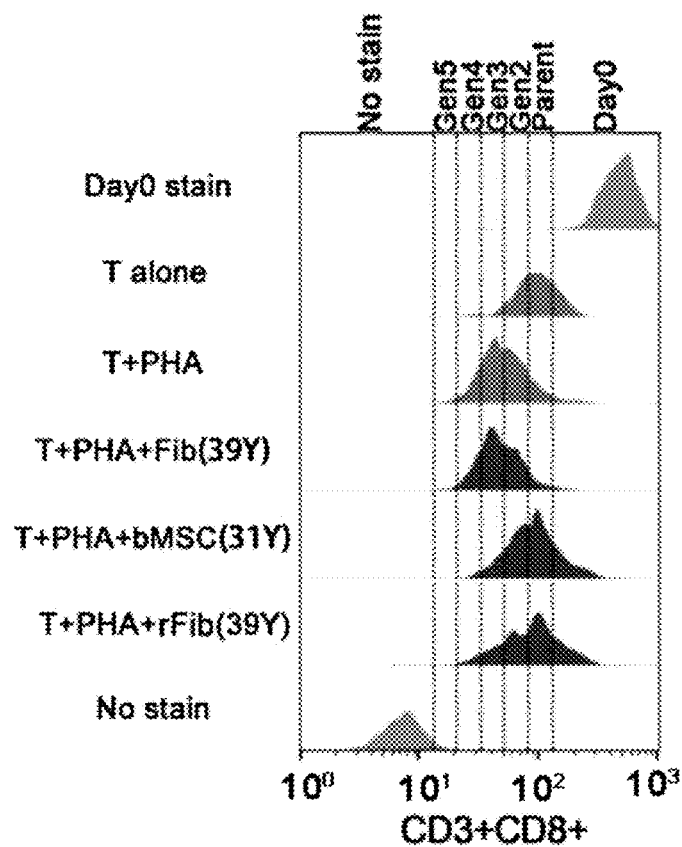
Figure 20A:
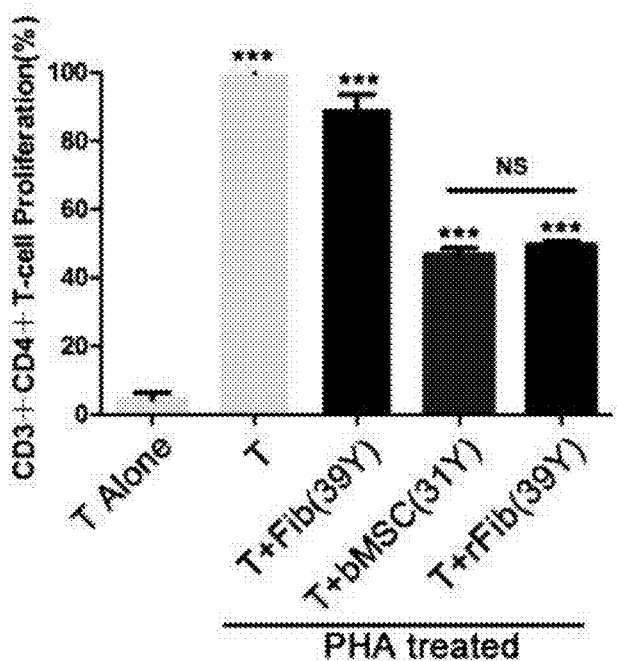
FIGS. 20A-B show immune suppression of CD3+ CD4+ T cells by rFibs in mixed lymphocyte reaction assay, where 19A: a proliferation rate of CD3+ CD4+ T cells; and 19B: CD4+ T cells proliferation analysis for CFSE staining by flow cytometry gated on CD4+ T cells.
Figure 20B:
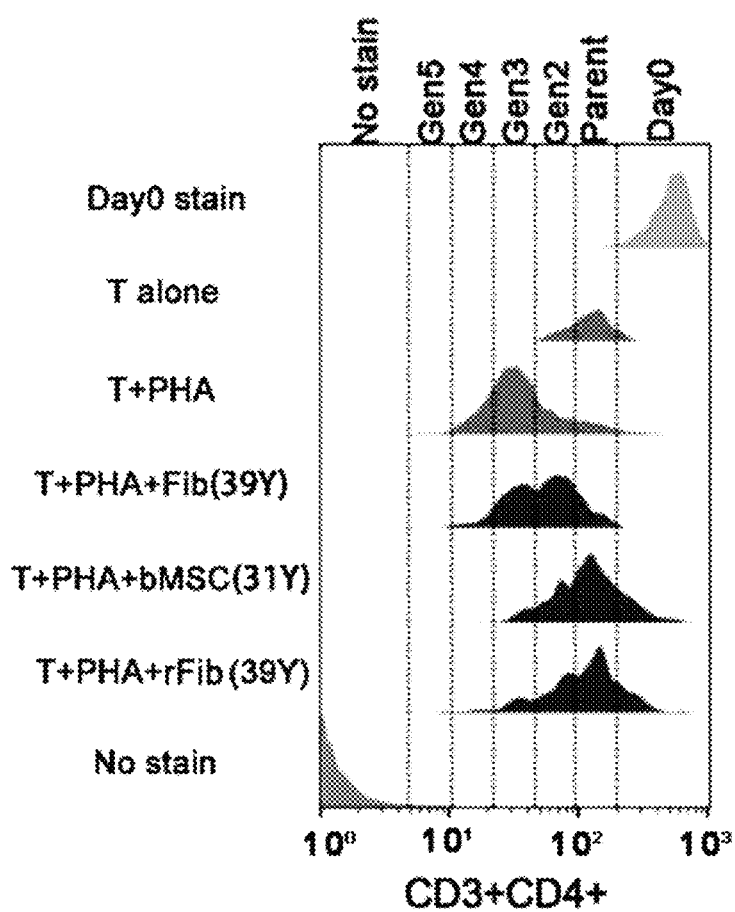

As shown in FIGS. 19A-B, the rFib exhibited the ability to regulate CD3+ CD8+ T cells proliferation; and as shown in FIGS. 20A-B, the rFib can also regulate the proliferation of CD3+ CD4+ T cells.

6.2 In Vivo Immunomodulation Test

The bMSC, rFib and Fib were respectively cultured in a 10 cm petri dish at a density of $1\times10^6$ for 48 hours, and then the culture medium was collected and filtered with a 0.22 μm filter membrane (Millipore) to remove the cells and cell debris. The resulting filtrate was concentrated by 100 times using an ultrafiltration centrifuge tube.

C57BL/6 mice, aged 8-12 weeks, were injected with concanavalin (diluted in PBS) via tail vein at 25 mg/kg (body weight) to induce acute liver injury, and some C57BL/6 mice were only injected with PBS as control (Han et al., 2014). Each group included 6 mice. 30 min later, the groups were respectively injected with the concentrated mediums or PBS, and the mice were sacrificed 8.5 hours after the injection of concentrated medium. The blood and liver were collected, where the liver was stained with H&E and detected for the content of CD3+ T cells by flow cytometry, and the blood was analyzed for the AST and ALT levels.

The quantification of serum ALT/AST was performed according to the instructions of an ELISA kit (Shanghai Meilian). Three independent replicate samples in each group were tested, and the results were expressed as mean±SD.

Figure 21:
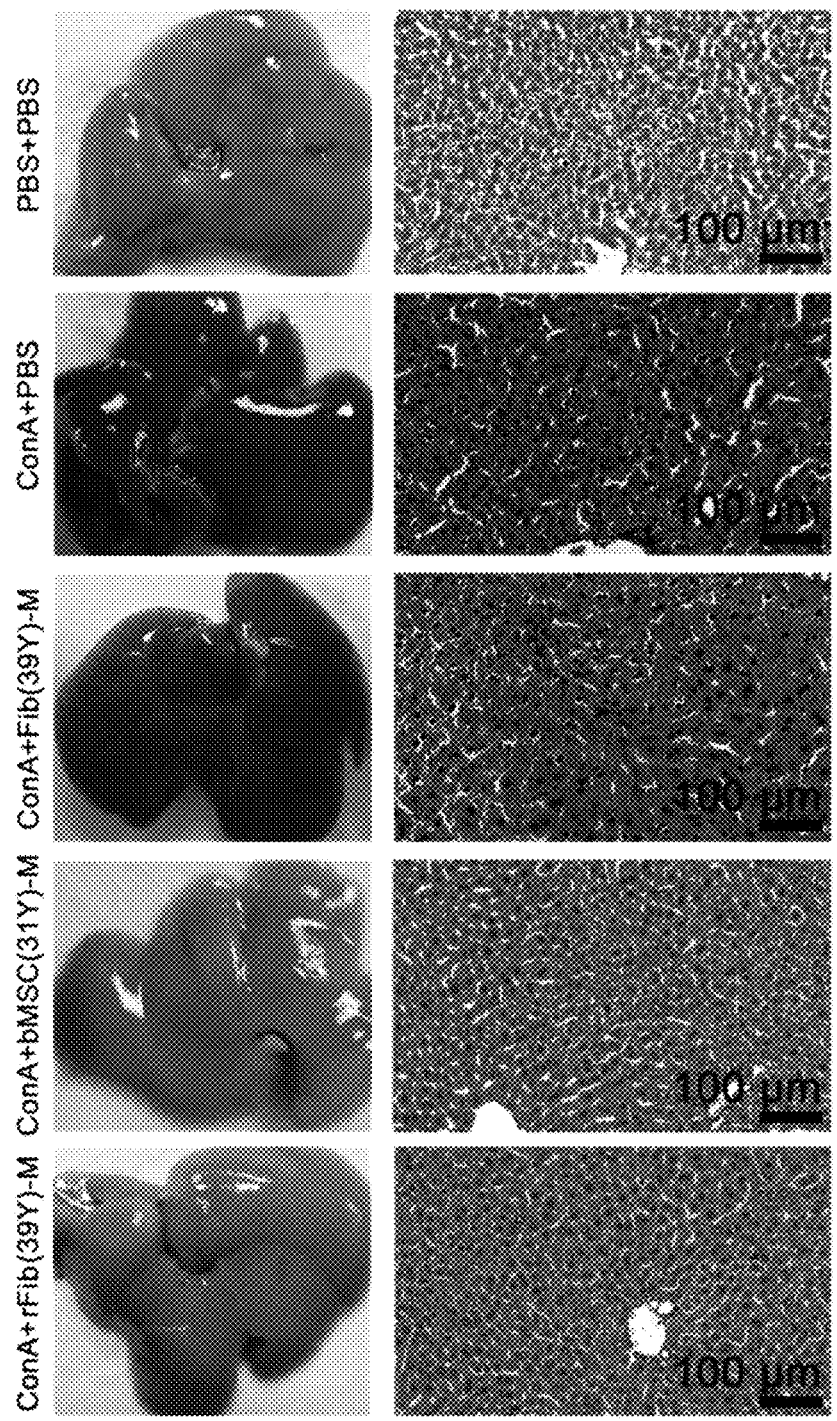
FIG. 21 shows liver morphology and H&E staining in the mice suffering concanavalin-induced acute liver injury after respectively treated with Fib, rFib and bMSC concentrated conditioned medium.

As shown in FIG. 21, it can be seen that after treated with the concentrated conditioned medium of rFib, the C57BL/6 mice suffering concanavalin-induced acute liver injury showed no obvious abnormal symptoms in the liver (such as bleeding and necrosis).

Figure 22:
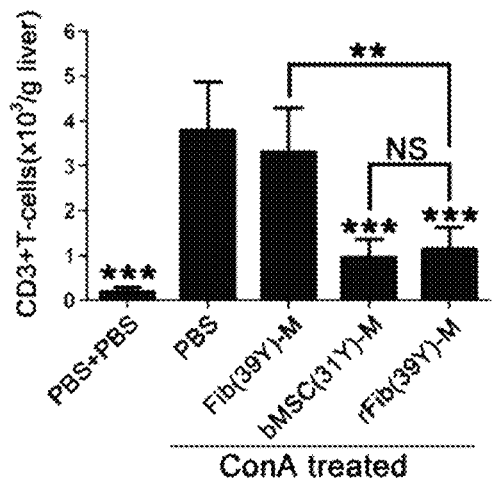
FIG. 22 shows content of CD3+ T cells in the liver of mice after respectively injected with Fib, rFib and bMSC concentrated conditioned medium.

FIG. 22 showed the numbers of T lymphocytes in liver which was determined 8.5 hours after the tail vein injection of the concentrated medium, where the rFib medium exhibited significant immune regulation ability, similar to the bMSC medium.

Figure 23A:
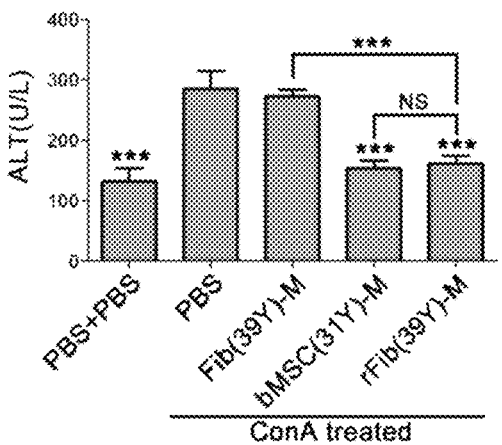
FIGS. 23A-B respectively show content of ALT and AST in blood of mice after respectively injected with Fib, rFib and bMSC.
Figure 23B:
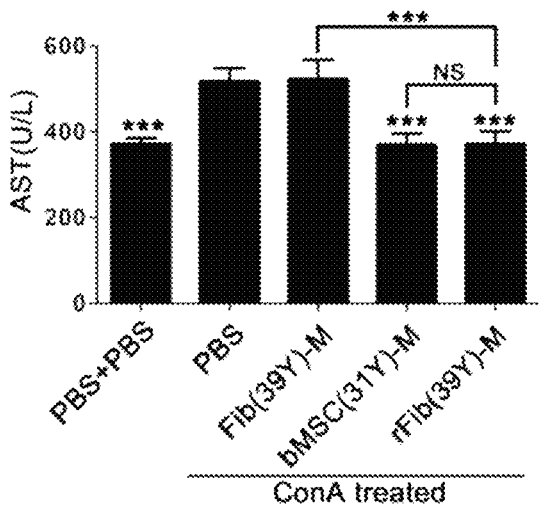

As shown in FIGS. 23A-B, the serum levels of ALT and AST of the mice treated with the rFib culture medium were close to normal levels, and there were no obvious liver injury symptoms.

6.3 PCR of Ordinary Genes

The extraction of total RNA was performed as instructed by TRIzol kit (Takara Bio). The reverse transcription of RNA (1.0 μg) into cDNA was performed using Primescript RT kit (Takara Bio). The q-RT-PCR system contained the cDNA as template, a pair of specific primers and SYBR Green, and employed SYBR Premix EX TaqTM II (Takara Bio). Parameters of cycles were set as recommended by the manufacturer (Takara). The relative expression level was normalized using an internal reference (ACTIN). In genomic PCR, the genomic DNA was used as a template for human-specific primer ACTIN, and Premix Taq (Takara Bio) was adopted.

Example 2 Repair Capability of rFib for Bone Defects

Under the approval of the ethics committee, NOD/SCID mice, aged 8-10 weeks and weighing 20-24 g were used to create femoral defect models and 5 mice in each group. The model was established as follows. Under the anesthesia of sodium pentobarbital, the skin and subcutaneous tissues of the mice were incised, and blunt separation was performed between the rectus femoris and semitendons to expose enough mid-femur. The operation is performed at the center of the right femur to construct continuous bone defect of 4 mm×1 mm. The Fib, bMSC and rFib were stained with Hoechst 33342 (Thermo, NucBlue live cell), respectively mixed with Matrigel and transplanted into the defect site at $5\times10^5$ cells/mouse.

28 days after transplantation, the mice were sacrificed by injection of a lethal dose of sodium pentobarbital. The thigh of each mouse was bluntly dissected, fixed with 4% PFA and imaged by μCT (SkyScan 1272, Bruker microCT), and the collected data was analyzed.

FIGS. 24-28 showed that the rFibs promote bone repair in vivo and was not limited by age.

Figure 24:
FIG. 24 shows the establishment of a femoral defect mouse model.

FIG. 24 schematically showed the establishment of the femoral defect mouse model.

Figure 25:
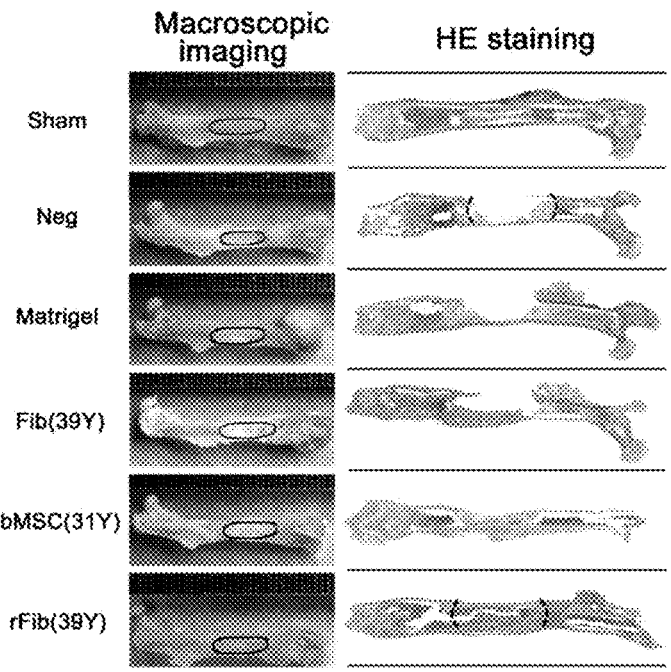
FIG. 25 shows macroscopic imaging and H&E staining results of femurs bone injury and repair from different groups of mice.

FIG. 25 illustrated femur samples of mice in different groups and H&E staining results thereof, where the bMSC from a 31-year-old volunteer and the rFib from a 39-year-old volunteer both exhibited good repair capability for bone defects.

Figure 26:
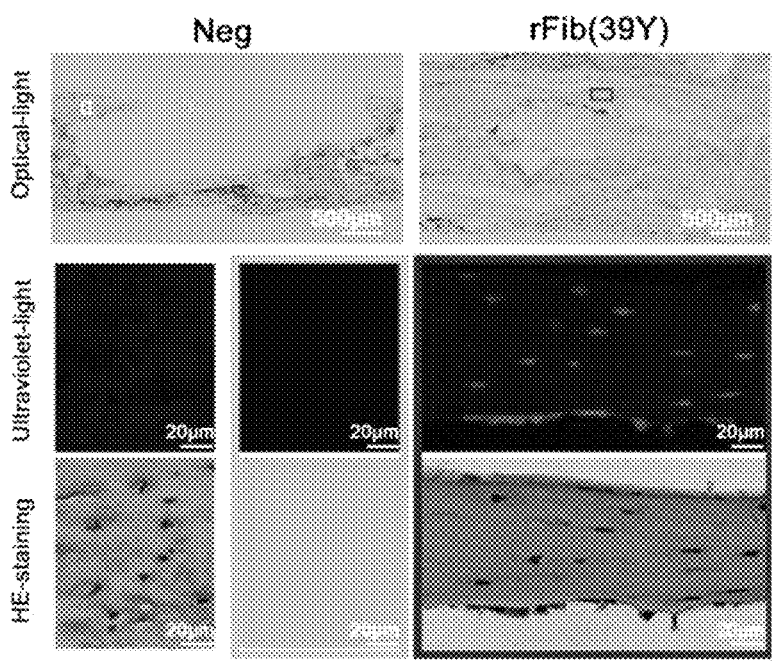
FIG. 26 shows Hoechst 33342-stained nuclei imaging and H&E staining results of sections of the repair site in the mice treated with rFib.

FIG. 26 illustrated sections of the repair site, in which the rFib was labeled with Hoechst 33342 and can emit blue fluorescence under ultraviolet light. It was clear that the rFib can form new bone at the defect site, and the number and location of Hoechst-positive human cells corresponded to newly formed bone cells highlighted by H&E staining, indicating that transplantation of h-rFibs induced bone healing by a cell-replacement strategy.

Figure 27:
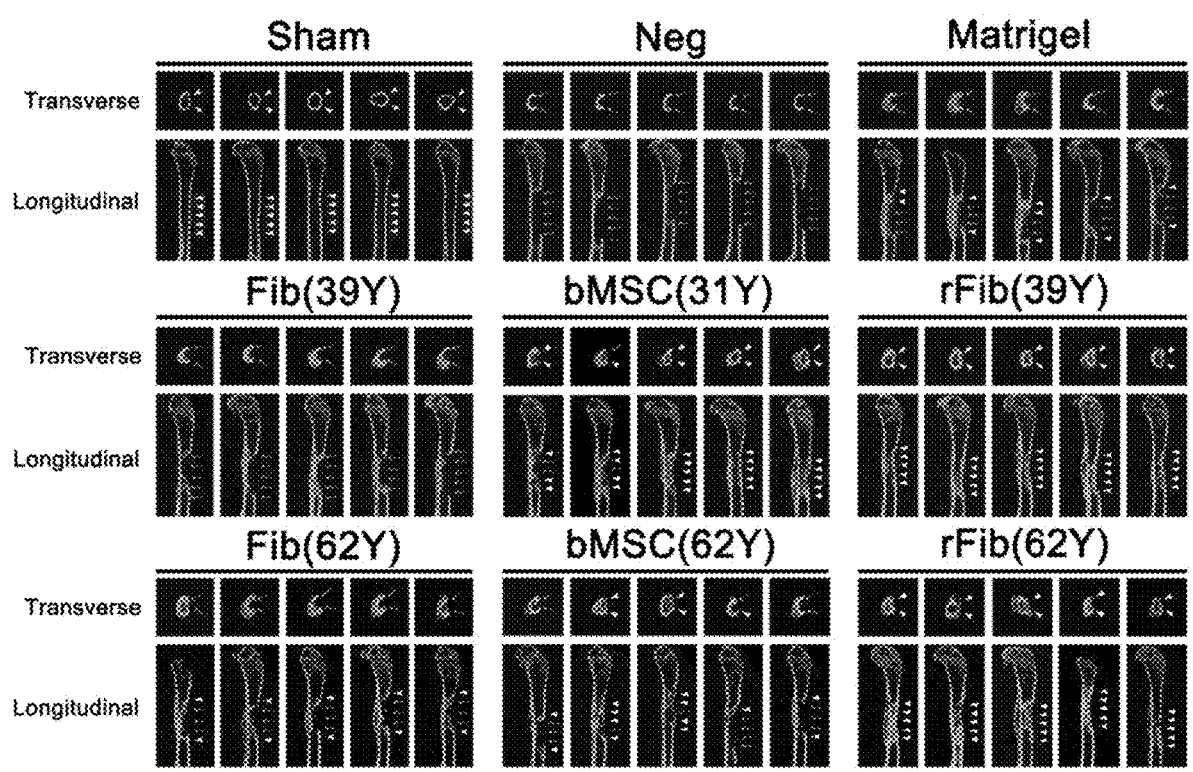
FIG. 27 shows micro-CT analysis results of the femoral defect mouse model after respectively treated with rFib and bMSC.

FIG. 27 showed micro-CT results of different experimental groups, from which it can be obtained that even the rFib from an elderly donor (62 years old) possessed obvious repair capability for bone defects, and by contrast, the bone repair capability of the bMSC from an elderly donor (62 years old) was extremely weak. Moreover, the rFib from a young donor (39 years old) and the rFib from an elderly donor (62 years old) had similar bone repair capabilities, which indicated that the repair capability of rFib for bone defects was not limited by the age of donor.

Figure 28:
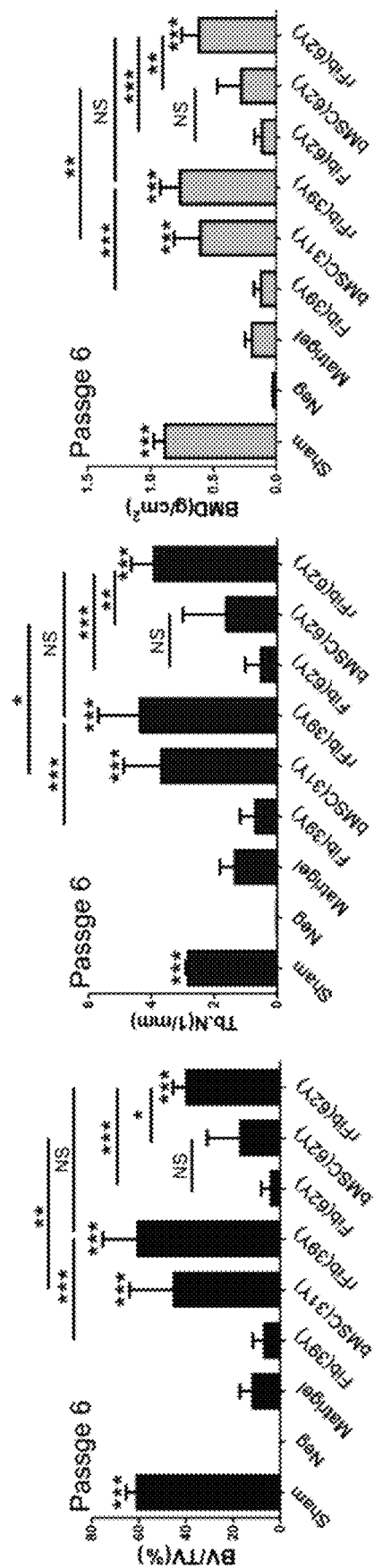
FIG. 28 shows BV/TV ratio, Tb.N and BMD in different groups of mice.

As shown in FIG. 28, the mice transplanted with the rFib (39 years old or 62 years old) were similar to the mice transplanted with bMSC (31 years old) in BV/TV ratio, Tb. N and BMD. Moreover, rFibs derived from donors of all ages were rather effective for bone repair.

Example 3 Repair Capability of rFib for Cartilage Defect

Establishment of articular cartilage defect model and cell transplantation

NOD/SCID mice, weighing 20-24 g and aged 8-10 weeks, were selected to establish a modified articular cartilage model to evaluate the efficacy of rFib (Cheng et al., 2014). The articular cartilage defect (1.5 mm×1 mm) was made in the trochlear groove of the distal femur with a biopsy punch. Cells ($2.5\times10^5$ in 35 μL of Matrigel) were labeled with Hoechst 33342 and implanted into the defect site, and the mice implanted with matrigel free of cells were used as control.

FIGS. 29A-B, 30 and 31 showed an in vivo cartilage repair experiment.

Figure 29A:
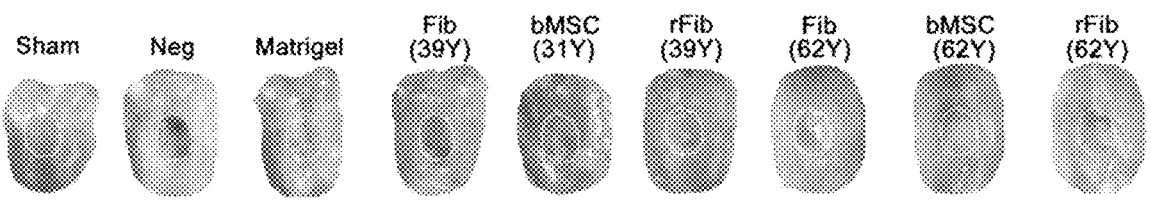
FIGS. 29A-B respectively show gross patellar groove and histological analysis of sections through knee cartilage by safranin O-fast green staining results thereof.
Figure 29B:

FIGS. 29A-B respectively showed macroscopic images of gross patellar groove and safranin-fast green staining results of a 10 μm section of knee cartilage, where alizarin red staining shows hyaline cartilage and safranin-fast green shows fibrocartilage or bone. It can be seen from these figures that both young rFib (39 years old) and bMSC (31 years old) can repair cartilage defects; the old bMSC (62 years old) failed to form new cartilage; and the rFib from an elderly donor (62 years old) can still form cartilage tissues.

Figure 30:
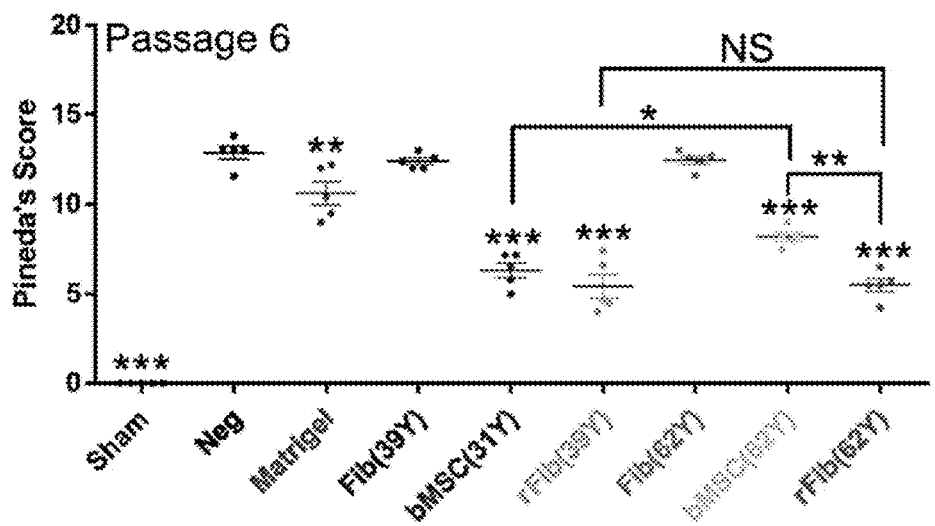
FIG. 30 shows Pineda's score for the cartilage repair in all experimental groups.

FIG. 30 showed Pineda's score for the cartilage repair in all experimental groups, and the results revealed that the rFib from an elderly donor (62 years old) and the rFib from a young donor (39 years old) had similar cartilage repair capabilities to the bMSC from 31 years old individual.

Figure 31:
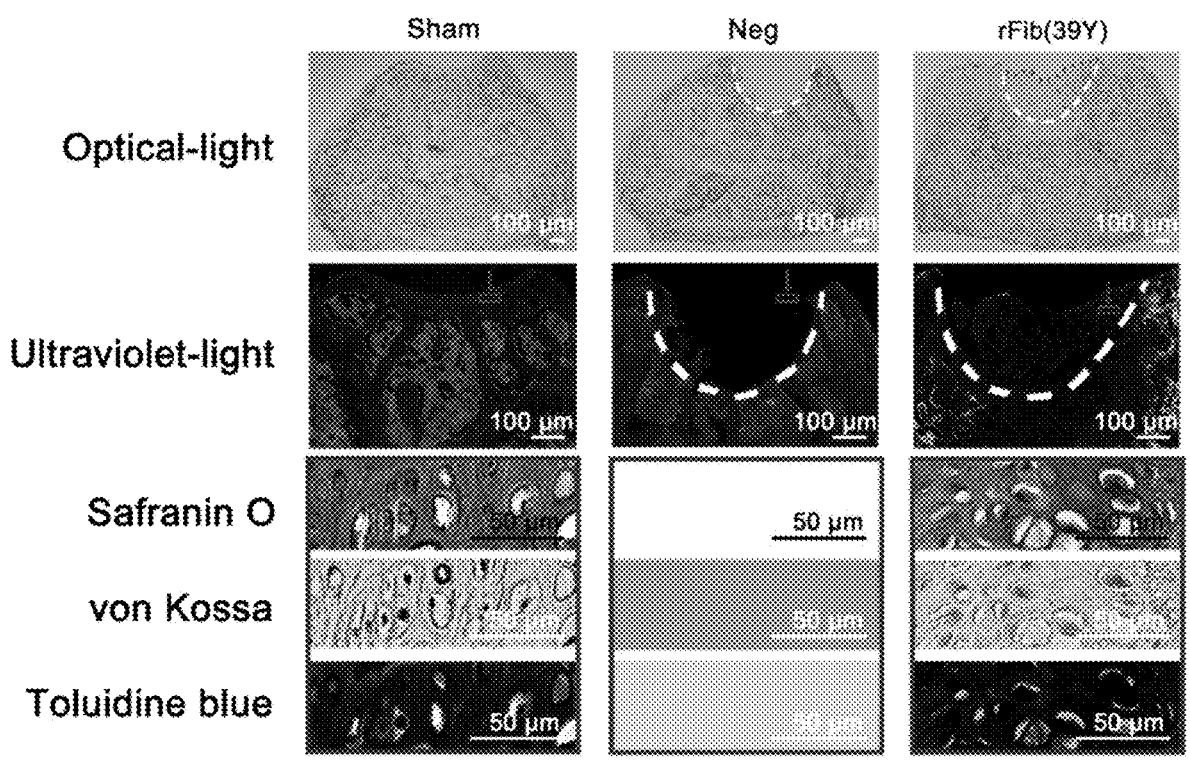
FIG. 31 shows hoechst 33342-stained nuclei imaging and Saf-O, von Kossa and Toluidine Blue staining results of a cartilage section after implanted with rFib.

The cartilage section demonstrated that the rFib labeled with Hoechst 33342 formed new cartilage tissues, and the newly formed cartilage tissues were similar to normal cartilages (FIG. 31). Moreover, no abnormal tissues were observed after the implantation of rFib.

Examples 4-12 Preparation of rFib Using a Small Molecular Combination

Examples 4-12 all provided preparation of rFib, but they varied in the used small molecular combination and the treatment time. The obtained rFib was characterized in the way mentioned in Example 1, and the small molecular combinations were listed in Table 1.

TABLE 1

Information about the preparation of rFib in Examples 4-12

| Example | Compound | Concentration | Treatment time (day) | Cell source |
|---|---|---|---|---|
| 4 | VPA | 0.05 mM | 9 | Human, monkey, mouse |
|  | CHIR99021 | 1 µM |  |  |
|  | Repsox | 0.5 µM |  |  |
|  | Forskolin | 3 µM |  |  |
| 5 | VPA | 10 mM | 9 | Human, monkey, mouse, pig |
|  | CHIR99021 | 3 µM |  |  |
|  | Repsox | 10 µM |  |  |
|  | Forskolin | 10 µM |  |  |
|  | SP600125 | 1 µM |  |  |
|  | Go 6983 | 5 µM |  |  |
|  | Y-27632 | 5 µM |  |  |
|  | AM580 | 0.05 µM |  |  |
|  | EPZ004777 | 5 µM |  |  |
|  | Vc | 0.2 mM |  |  |
|  | TTNPB | 5 µM |  |  |
| 6 | VPA | 0.5 mM | 12 | Human, monkey |
|  | CHIR99021 | 15 µM |  |  |
|  | Repsox | 1 µM |  |  |
|  | Forskolin | 50 µM |  |  |
|  | SP600125 | 10 µM |  |  |
|  | Go 6983 | 20 µM |  |  |
|  | Y-27632 | 25 µM |  |  |
|  | AM580 | 0.02 µM |  |  |
|  | EPZ004777 | 5 µM |  |  |
|  | Vc | 0.2 mM |  |  |
|  | TTNPB | 0.2 µM |  |  |
| 7 | VPA | 0.5 mM | 12 | Human, monkey |
|  | CHIR99021 | 3 µM |  |  |
|  | Repsox | 1 µM |  |  |
|  | Forskolin | 10 µM |  |  |
|  | SP600125 | 50 µM |  |  |
|  | Go 6983 | 1 µM |  |  |
|  | Y-27632 | 1 µM |  |  |
|  | AM580 | 1 µM |  |  |
|  | EPZ004777 | 0.5 µM |  |  |
|  | Vc | 0.2 mM |  |  |
|  | TTNPB | 5 µM |  |  |
| 8 | VPA | 0.5 mM | 9 | Human, monkey, mouse, pig |
|  | CHIR99021 | 3 µM |  |  |
|  | Repsox | 1 µM |  |  |
|  | Forskolin | 10 µM |  |  |
|  | Go 6983 | 5 µM |  |  |
|  | Y-27632 | 5 µM |  |  |
|  | AM580 | 0.05 µM |  |  |
|  | EPZ004777 | 15 µM |  |  |
|  | Vc | 0.2 mM |  |  |
|  | TTNPB | 5 µM |  |  |
| 9 | CHIR99021 | 2 µM | 15 | Human, monkey, mouse, pig |
|  | Repsox | 2 µM |  |  |
|  | Forskolin | 4 µM |  |  |
| 10 | Ruxolitinib | 0.006 µM | 12 | Human |
| 11 | VPA | 0.5 mM | 10 | Human, monkey, mouse |
|  | CHIR98014 | 3 µM |  |  |
|  | Repsox | 1 µM |  |  |
|  | Forskolin | 10 µM |  |  |
|  | SP600125 | 10 µM |  |  |
|  | Go 6983 | 5 µM |  |  |
|  | Y-27632 | 5 µM |  |  |
|  | AM580 | 0.05 µM |  |  |
|  | EPZ004777 | 5 µM |  |  |
|  | Vc | 0.2 mM |  |  |
|  | TTNPB | 20 µM |  |  |
| 12 | Ruxolitinib | 0.006 µM | 10 | Human, monkey, mouse |
|  | S31-201 | 10 µM |  |  |

Example 13 Preparation of Super Fibroblasts

1. A CRISPR/Cas9 STAT5a-knockout plasmid was constructed, in which the following plasmids were used (purchased from Cyagen Co., Ltd):

pLV [2gRNA]-EGFP:T2A: Puro-U6>hSTAT5A [gRNA #4]-U6>hSTAT5A [gRNA #10]; and pLV [Exp]-CBh>hCas9:T2A:Hygro.

2. Cells were transfected with viruses as recommended by the manufacturer. On the first day after transfection, the virus-containing medium was replaced with a fresh complete medium, and the incubation was performed at 37° C. and 5% $CO_2$.

3. From the second day after the transfection, the genes carried by the lentivirus began to express and the cells can be continuously cultured to further accumulate the expression products or change the cell phenotype.

4. After expansion, the virus-transfected cells were purified with antibiotics and continuously cultured with HG-DMEM containing 10% FBS for 150 days.

FIGS. 32-35, 36A-C and 37 demonstrated that the inhibition of STAT5 gene can promote the rejuvenation of fibroblasts and allow the fibroblasts to acquire multiple differentiation abilities.

Figure 32:
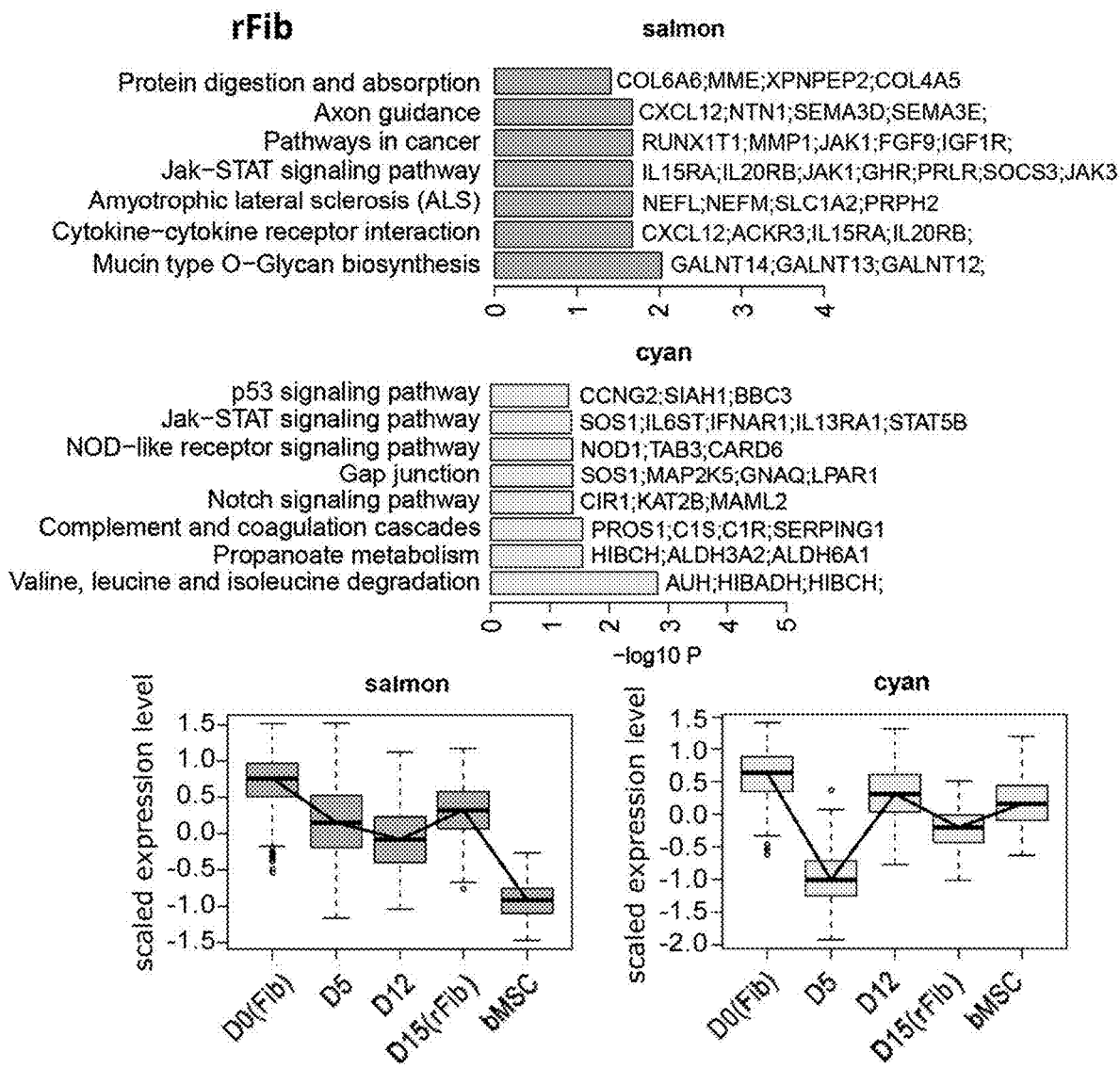
FIG. 32 shows two representative modules of KEGG pathways enrichment were determined by WGCNA of 12,036 genes and Box plots of changes in expression of 2 gene modules across each sample types.

FIG. 32 showed two representative modules of KEGG pathways enrichment were determined by WGCNA of 12,036 genes and Box plots of changes in expression of 2 gene modules across each sample types.

Figure 33:
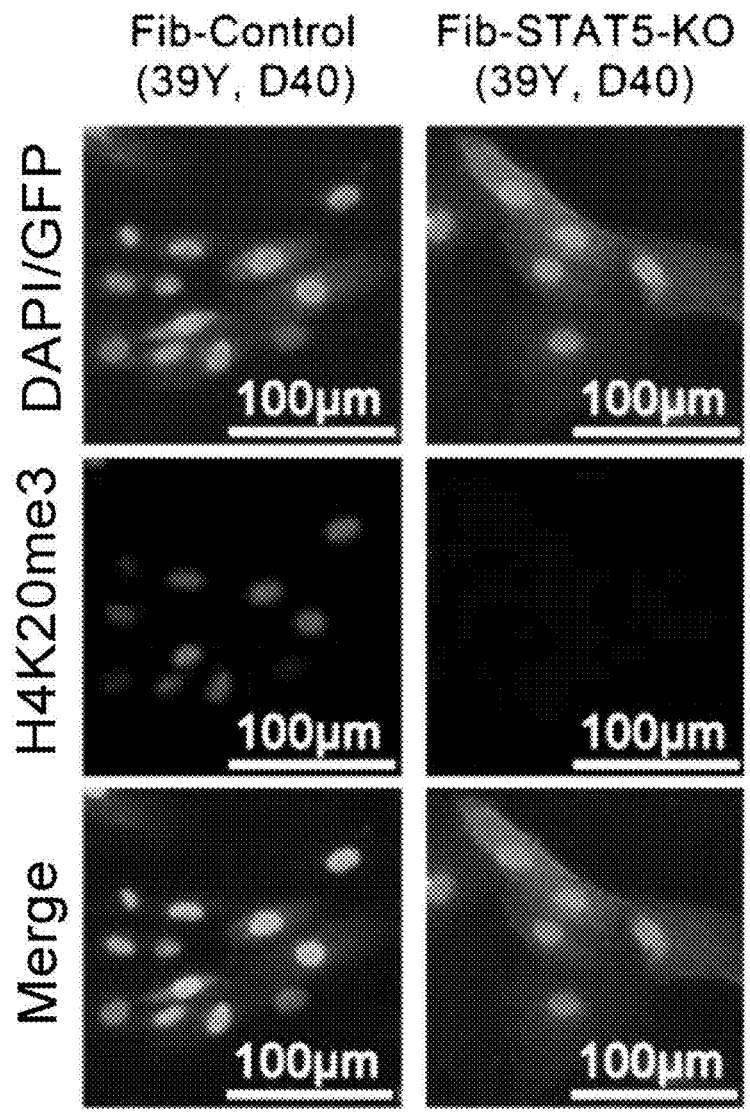
FIG. 33 shows immunofluorescence detection of H4K20me3 after STAT5A knockout in fibroblasts.
Figure 34A:
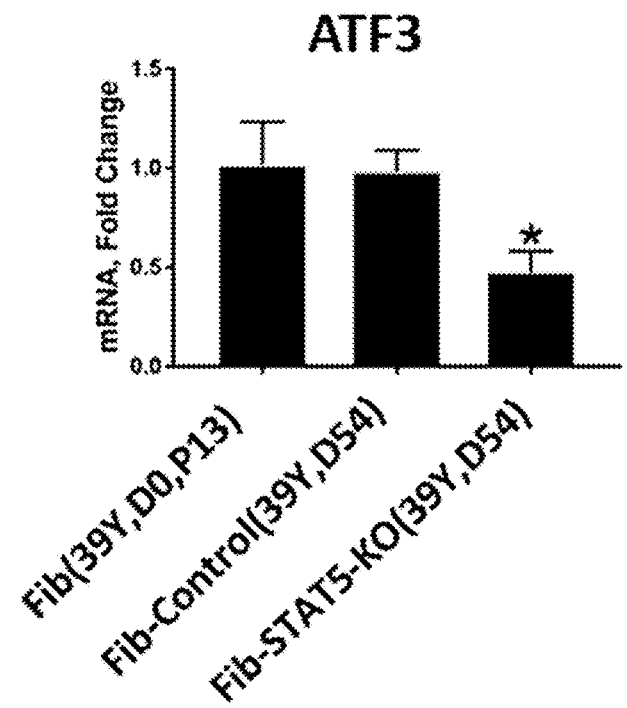
FIGS. 34A-D depict expression levels of ATF3, CDKN1A, GADD45B and IL-6 in control Fib and STAT5-knockout Fib, where 34A: ATF3; 34B: CDKN1A; 34C: GADD45B; and 34D: IL-6.
Figure 34B:
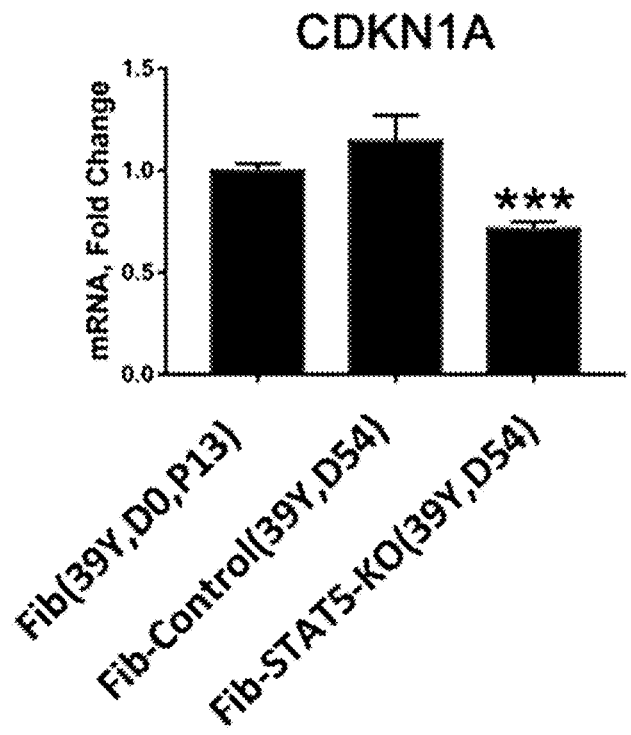
Figure 34C:
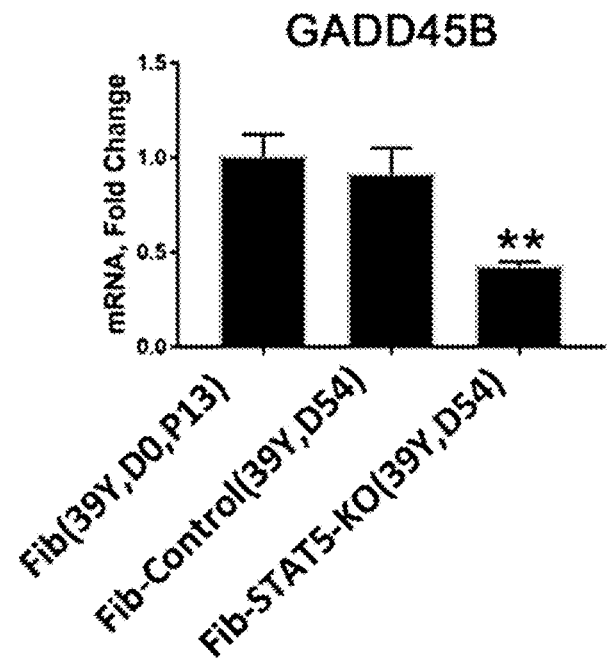
Figure 34D:
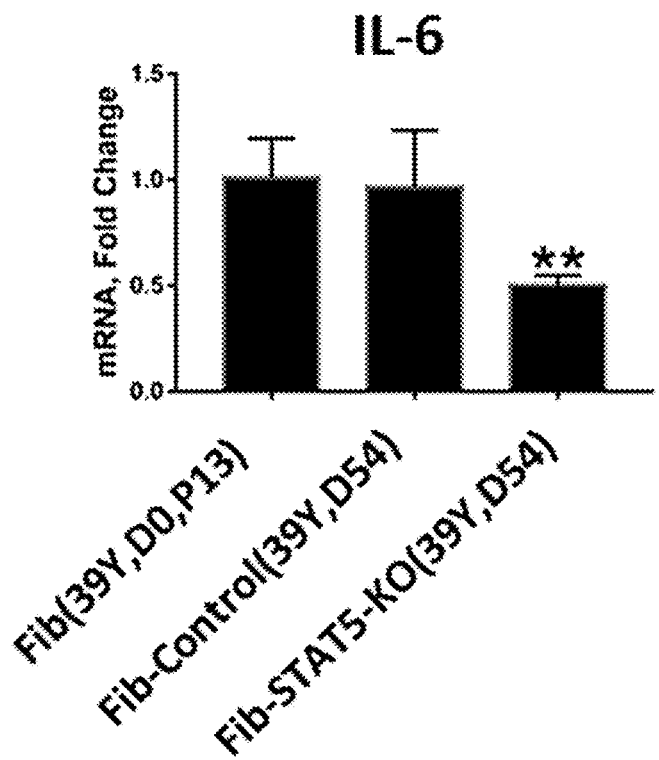

After continuously cultured for 40 days after the knockout of STAT5 gene, the Fib was subjected to immunohistochemical staining, and the results were shown in FIG. 33. This figure illustrated that compared to the control Fib, the STAT5-KO Fib (Fib with STAT5 gene knocked out) had significantly reduced senescence marker H4K20me3 (the content was positively correlated with the aging degree).

FIGS. 34A-D showed expression levels of four senescence marker genes ATF3, GADD45B, IL6 and CDKN1A (high expression level in aged cells), from which it can be concluded that the STAT5-KO Fib experienced significant reduction in the expression levels of senescence marker genes.

Figure 35:
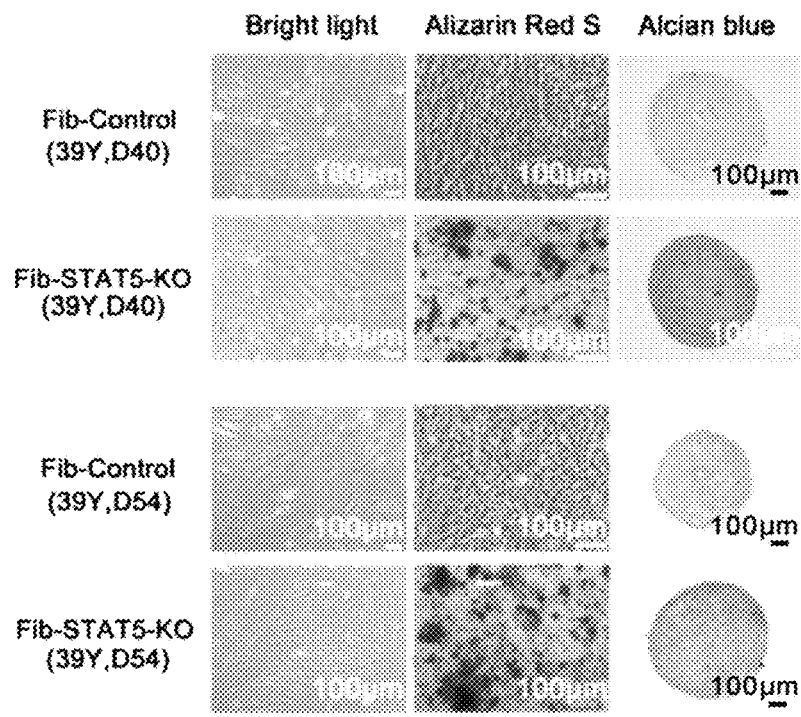
FIG. 35 illustrates the control Fib and the STAT5-knockout Fib stained with alizarin red S and alcian blue after osteogenic and chondrogenic differentiation respectively.

The STAT5-KO Fib exhibited osteogenic (Alizarin Red S staining) and chondrogenic (Alcian Blue staining) capabilities (FIG. 35).

Figure 36A:
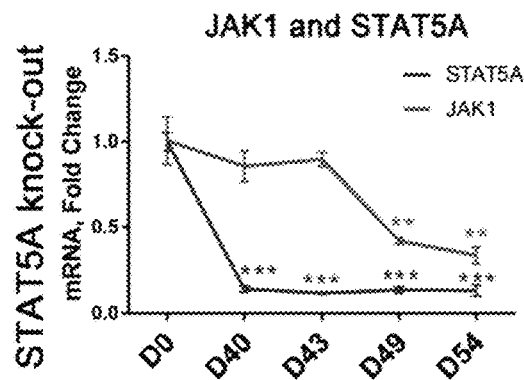
FIGS. 36A-C show changes in expression of JAK1, STAT5 and TERT and changes in the relative telomere length after STAT5 is knocked out, where 36A: expression of JAK1 and STAT5; 36B: expression of TERT; and 36C: relative telomere length.
Figure 36B:
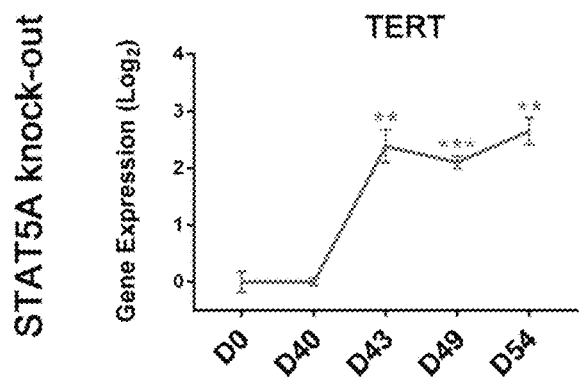
Figure 36C:
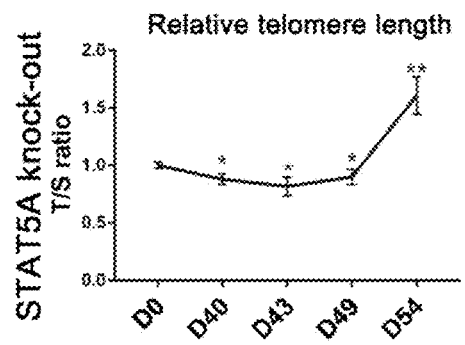

FIGS. 36A-C depicted changes in expression of JAK1, STAT5 and TERT and changes in the relative telomere length after the STAT5 gene was knocked out, where the JAK1 and STAT5 showed declined expression; the TERT was highly expressed 43 days after the knockout of STAT5 gene; and the telomere length was significantly increased 54 days after the knockout of STAT5 gene.

Figure 37:
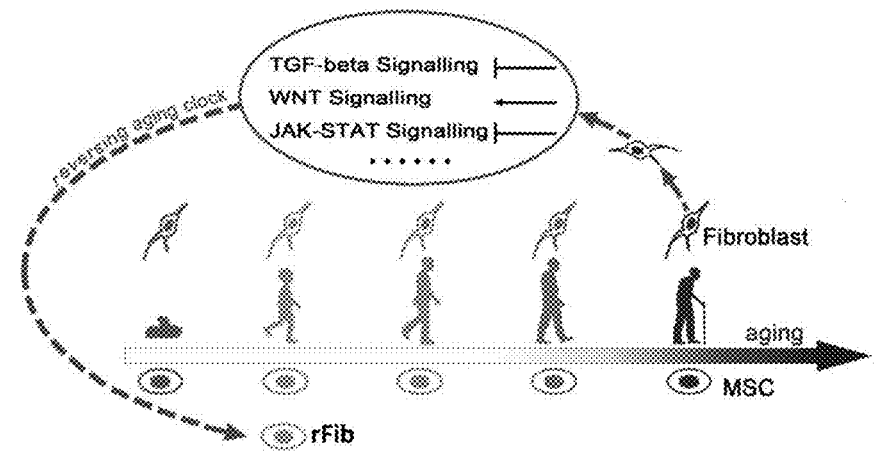
FIG. 37 schematically shows the preparation of rFib from Fib by regulating the Jak-Stat signaling pathway and the function of rFibs.

FIG. 37 schematically shows the preparation of rFib from Fib by regulating the Jak-Stat signaling pathway and the function of rFibs.

Figure 38A:
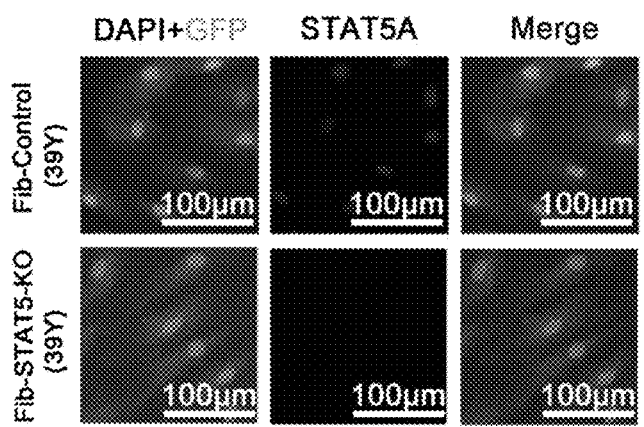
FIGS. 38A-B show influence of STAT5 knockout on expressions of STAT5A and H3K9me, where 38A: STAT5A; and 38B: H3K9me.
Figure 38B:
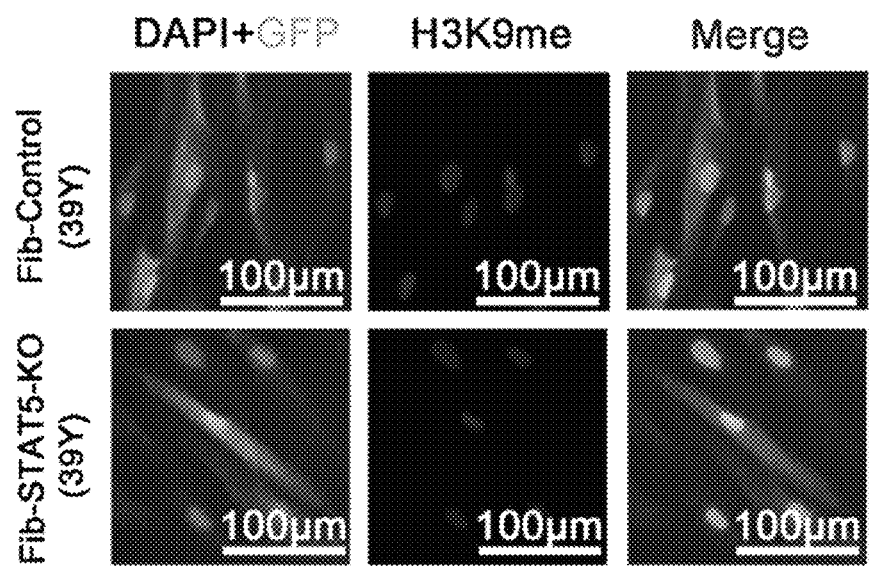

FIGS. 38A-B showed influence of STAT5 knockout on STAT5 and H3K9me. Specifically, the STAT5 was no longer expressed after the STAT5 was knocked out (FIG. 38A); and the knockout of STAT5 showed no significant influence on H3K9me (FIG. 38B).

FIGS. 39-43 reflected the detection results of senescence-related indexes and differentiation potentials of another STAT5-KO Fib (derived from a 62-year-old donor).

Figure 39:
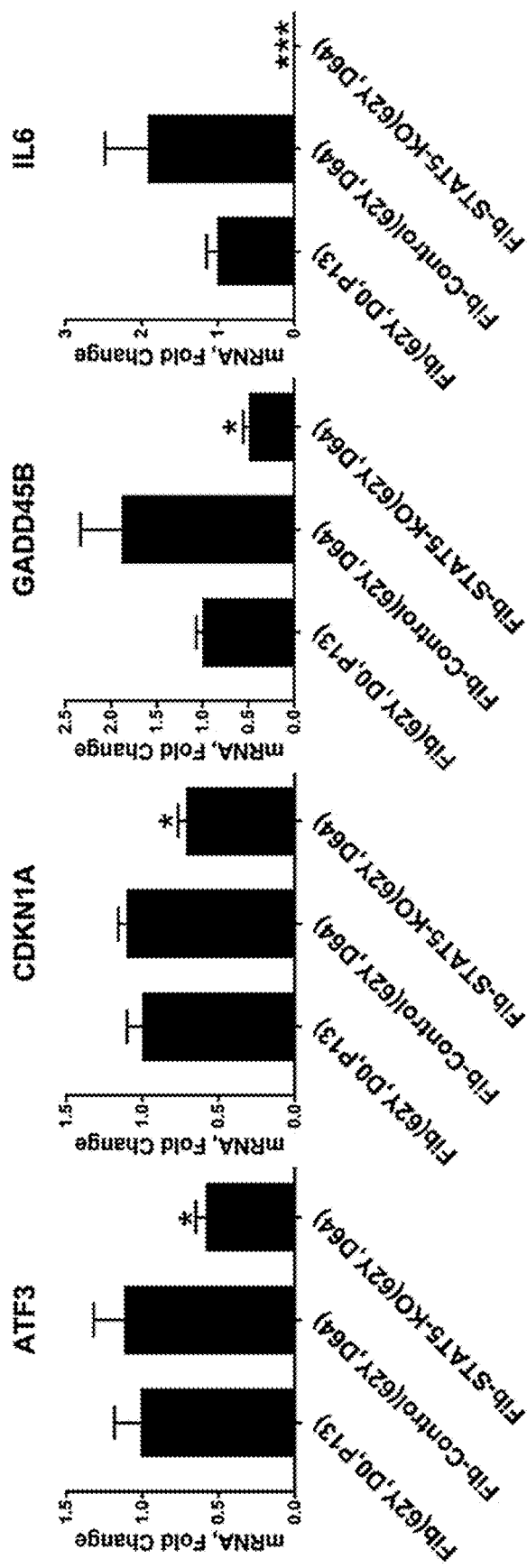
FIG. 39 shows expression levels of senescence-associated genes in control Fib (from a 62-year-old person) and STAT5-knockout Fib.
Figure 40:
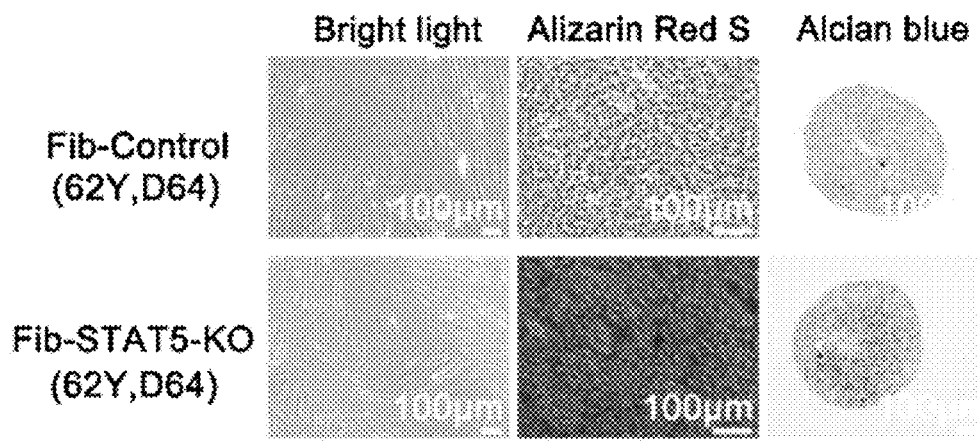
FIG. 40 illustrates the control Fib and the STAT5-knockout Fib after stained with alizarin red S and alcian blue after osteogenic and chondrogenic differentiation respectively.
Figure 41A:
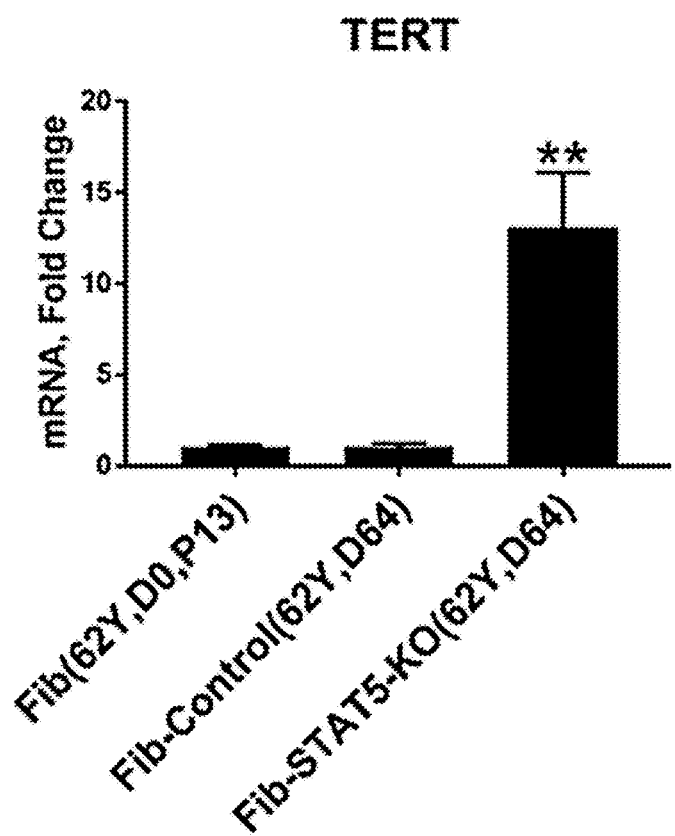
FIGS. 41A-B respectively depict expression of TERT and relative telomere length of the control Fib and the STAT5-knockout Fib.
Figure 41B:
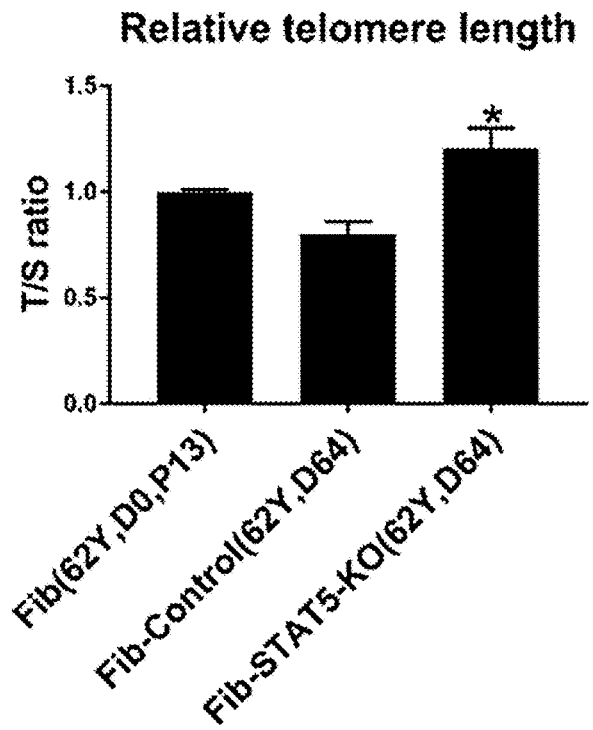
Figure 42:
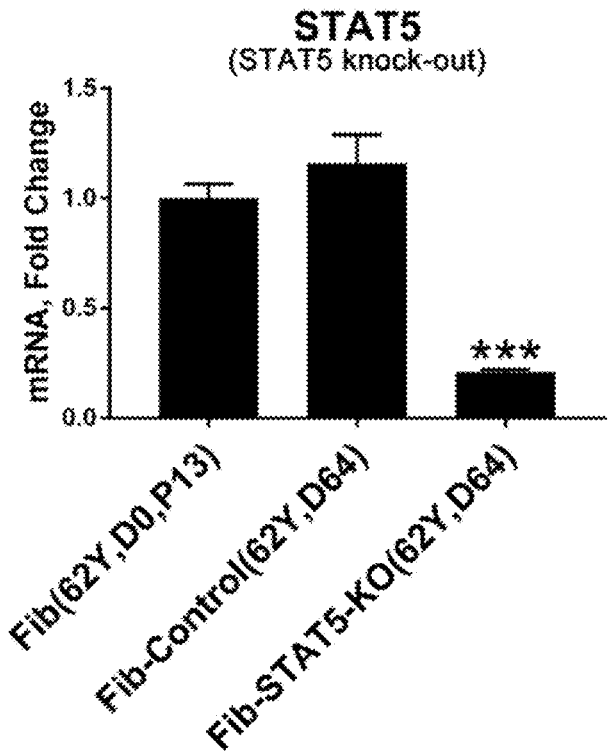
FIG. 42 shows expression level of STAT5 in the parent Fib, control Fib and the STAT5-knockout Fib.
Figure 43:
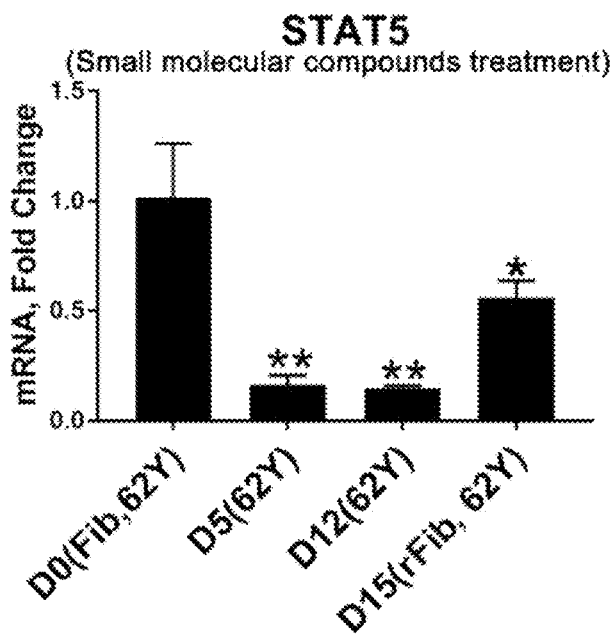
FIG. 43 shows the influence of small molecular compounds on the expression of STAT5.

Specifically, the expression levels of senescence-related genes were shown in FIG. 39; the measurement results of osteogenic and chondrogenic differentiation potentials were presented in FIG. 40; the expression level of TERT and the relative telomere length were shown in FIGS. 41A-B; the expression level of STAT5 was shown in FIG. 42; and the expression level of STAT5 in the same cell line treated with Mix V+Mix P system was shown in FIG. 43.

Example 14 Rejuvenation of MSCs

1. Bone marrow mesenchymal stem cells (bMSCs) from different donors were respectively cultured in a LG (low glucose)-DMEM containing 10% FBS.

2. After treated with different compound combinations for 3 days, the cells were continuously cultured in the LG-DMEM containing 10% FBS for 3 days and then stained with β-galactosidase.

TABLE 2

Compound combinations and treatment time

| Combination | Compound | Concentration | Treatment time (day) |
|---|---|---|---|
| 2M | CHIR99021 | 3 μM | 3 |
|  | AZA | 1 μM |  |
| 2K | CHIR99021 | 3 μM | 3 |
|  | AZA | 5 μM |  |
| 4K | CHIR99021 | 1 μM | 3 |
|  | AZA | 2 μM |  |
|  | Forskolin | 10 μM |  |

Figure 44:
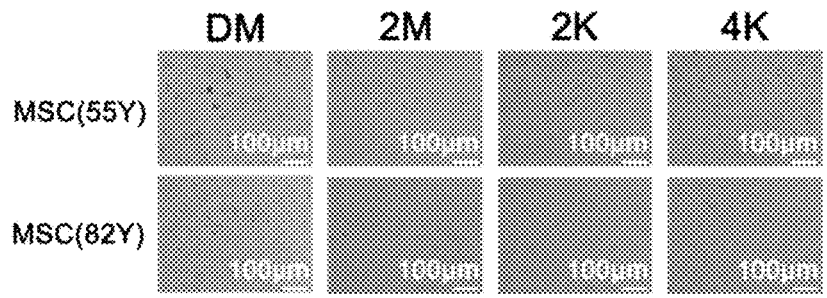
FIG. 44 shows β-galactosidase staining results of MSCs respectively treated different compound combinations, where the MSCs are derived from donors of different ages.

The β-galactosidase staining results of MSCs from donors of different ages were shown in FIG. 44.

Example 15 Extension of Lifespan of Aged Mice Through Intravenous Injection of rFib Passage 9 Fib and passage 13 rFib from a 39-year-old donor and passage 8 rFib from a 62-year-old donor were labeled with Hoechst 33342 and suspended with 200 μL of DMEM, respectively. The cells were injected into naturally aged NOD/SCID mice (aged 43 weeks (approximately corresponding to 86 years of humans), average life span: 36-38 weeks) through tail vein at $10^6$/mouse. The mice in the vehicle group were only injected with 200 μL of DMEM. Tissues and organs were collected for detection after the mice died naturally.

FIGS. 45-58 demonstrated that the rFib can effectively prolong the life span of NOD/SCID mice and improve the bone density.

Figure 45:
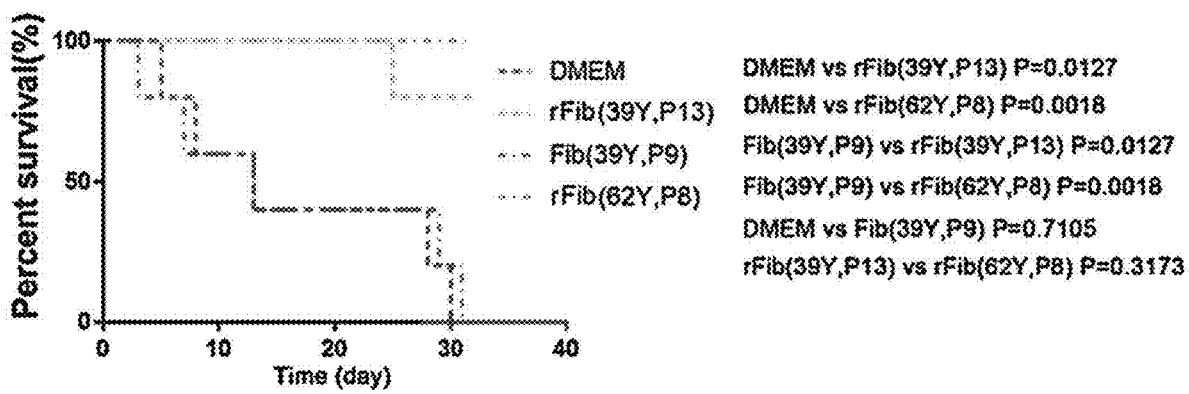
FIG. 45 shows the effect of rFib on the survival rate of aged mice.

Specifically, FIG. 45 showed survival curves of the aged mice, where the mice injected with rFib (whether derived from a young donor (39 years old) or an elderly donor (62 years old)) had extended life span. By contrast, the young Fib had no effect on extending lifespan, and the survival curve of the mice injected with the young Fib was similar to that of the mice in the vehicle group.

Figure 46:
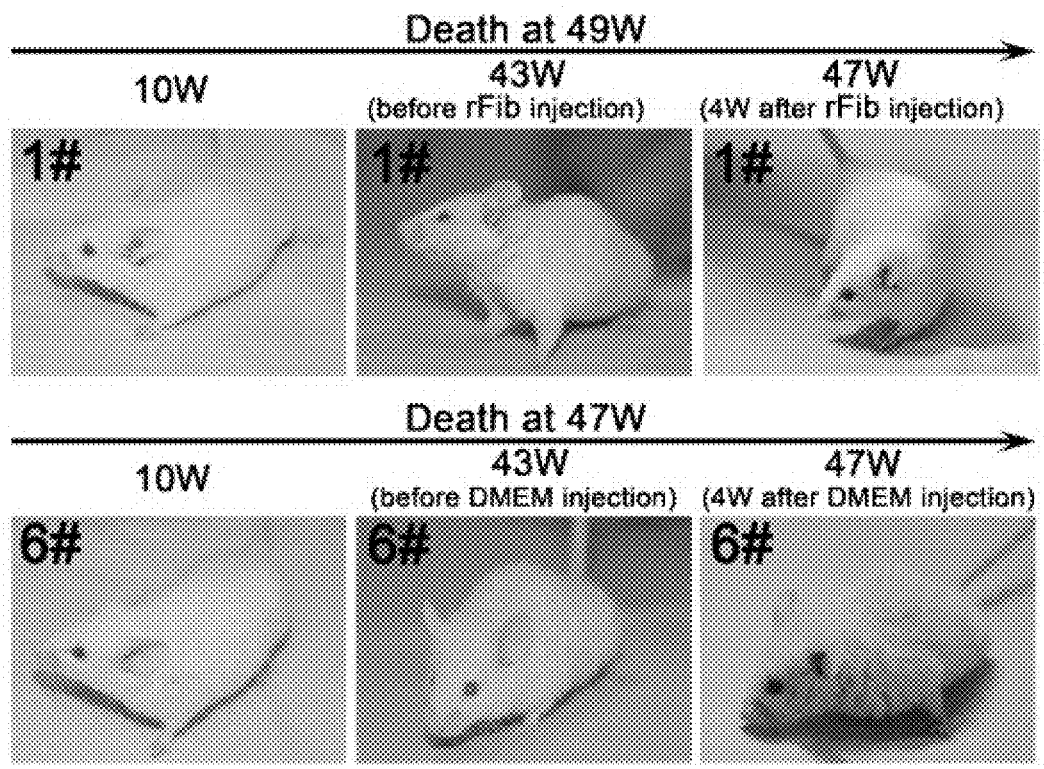
FIG. 46 shows the effect of rFib on the representative images of aged mice.

Representative images of aged mice treated with DMEM, rFib were shown in FIG. 46, where these animals showed great improvement in their appearance based on their fur coats and reduced spine curvature as compared to DMEM medium (vehicle)-treated animals. After four weeks of injection of rFib, the mice's conditions were significantly improved, while by contrast, the mice injected with DMEM became more senile after 4 weeks.

Figure 47:
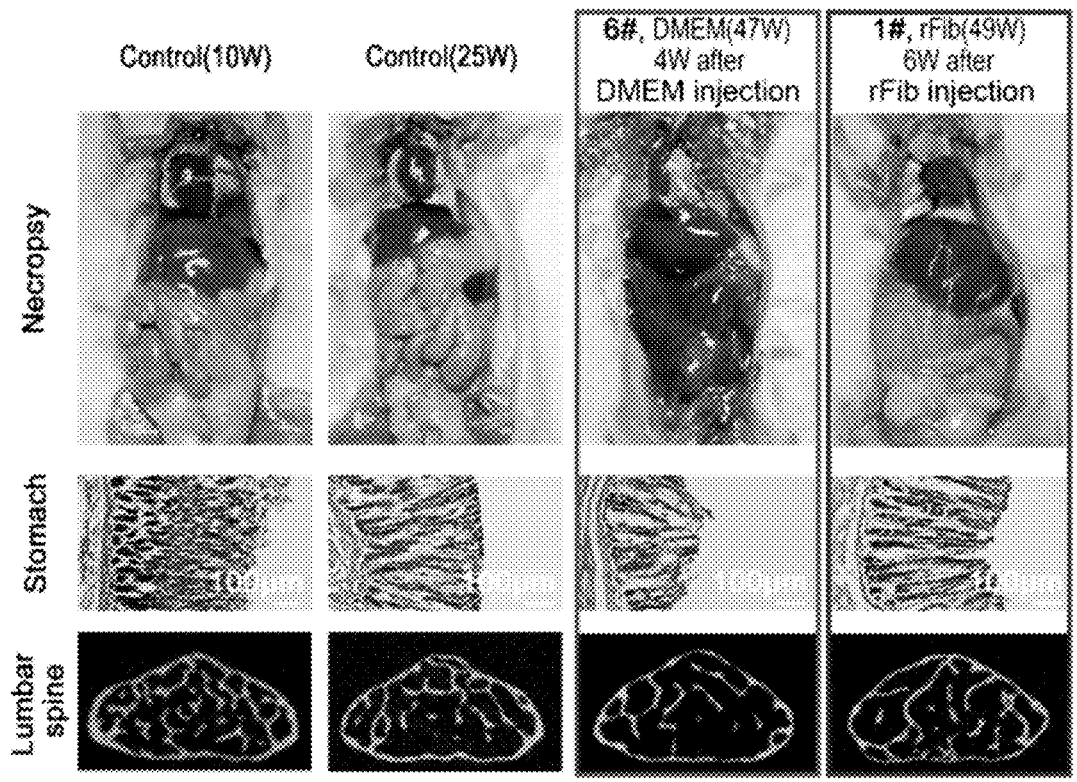
FIG. 47 shows the morphology of tissues and organs of four mice respectively aged 10 weeks, 25 weeks, 47 weeks (injected with DMEM at the 43rd week, died at the 47th week) and 49 weeks (injected with rFib at the 43rd week, died at the 49th week).

FIG. 47 presented necropsy, H&E staining image of stomach tissues sections and micro-CT image of bone microarchitecture in the lumbar spine of four mice aged 10 weeks, 25 weeks, 47 weeks (injected with DMEM at the $43^{rd}$ week and died at the $47^{th}$ week) and 49 weeks (injected with rFib at the $43^{rd}$ week and died at the $49^{th}$ week). It can be observed from these figures that the appearance of the digestive systems of the mice injected with rFib was similar to that of young mice (aged 25 weeks); stomach tissues in rFib-treated animals had more regular gastric mucosa and age-related loss of parietal cells were recovered by rFib transfusions; significant improvement in bone architecture after rFib intravenous injection similar to those of the 25-week-old mice.

By contrast, the digestive systems appeared discolored and malfunctioning, and the skeleton displayed clear signs of osteoporosis in lumbar spine trabecular cone microarchitecture in the aged mice injected with DMEM.

Figure 48:
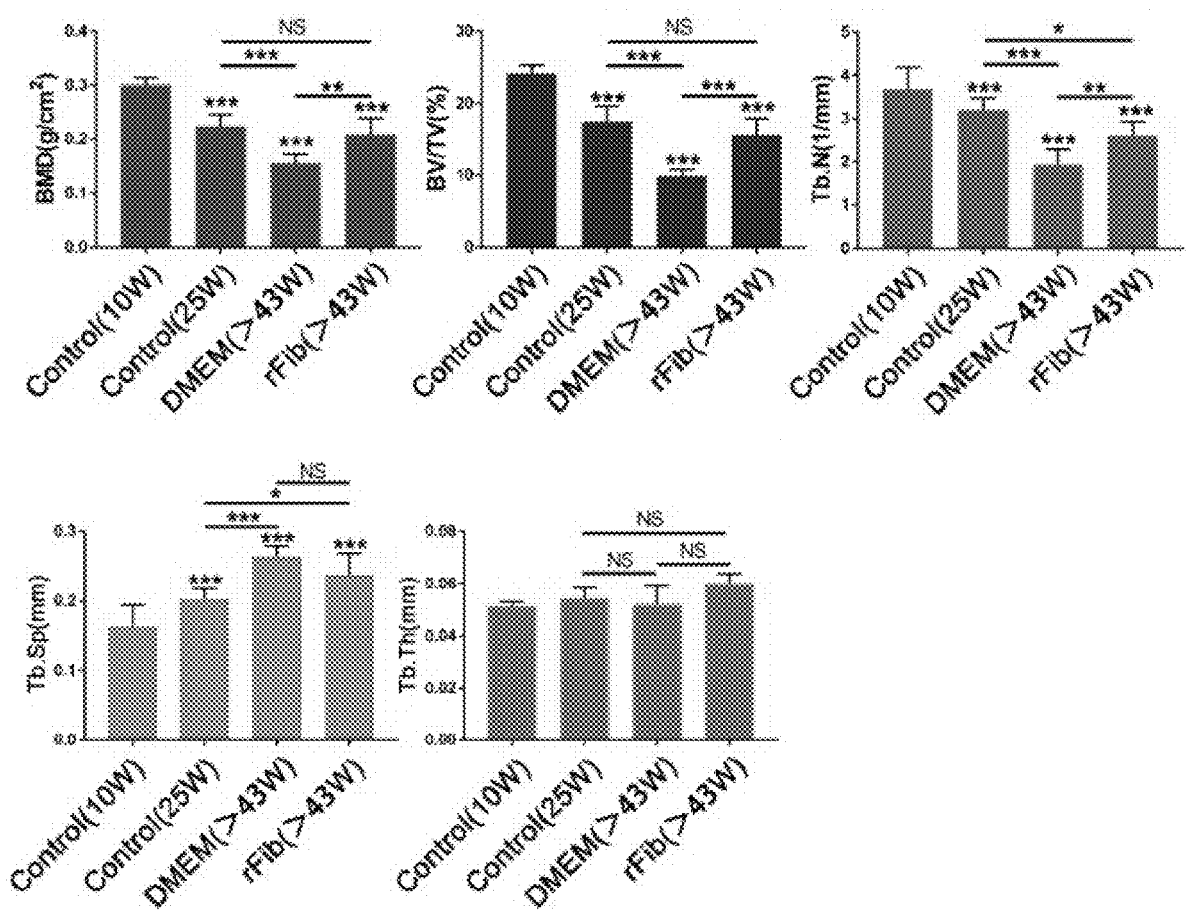
FIG. 48 shows the effect of rFib on BMD, BV/TV ratio, Tb. N, Tb. Sp and Tb. Th of aged mice.

The analysis results of the obtained micro-CT data were shown in FIG. 48, from which it can be seen that the aged mice injected with rFib were similar to the 25-week-old mice in bone mineral density (BMD) and relative bone volume (BV/TV), and had improved trabecular number (Tb. N) and trabecular separation/spacing (Tb. Sp) (5 mice in each group, *p<0.05, p<0.01, *p<0.001, n=5).

Figure 49:
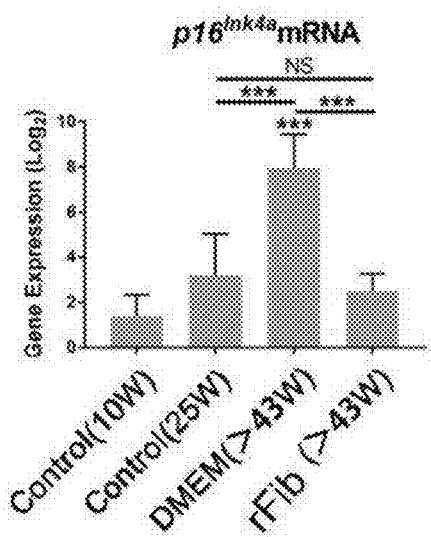
FIG. 49 shows the effect of rFib on the expression level of p16$^{Ink4a}$ in aged mice.

The expression levels of $p16^{Ink4a}$ in different groups of mice were presented in FIG. 49, where there was no significant difference between the aged mice injected with rFib and the 25-week-old and 10-week-old mice, while the expression level of $p16^{Ink4}$ in the aged mice injected with DMEM was increased significantly.

Figure 50:
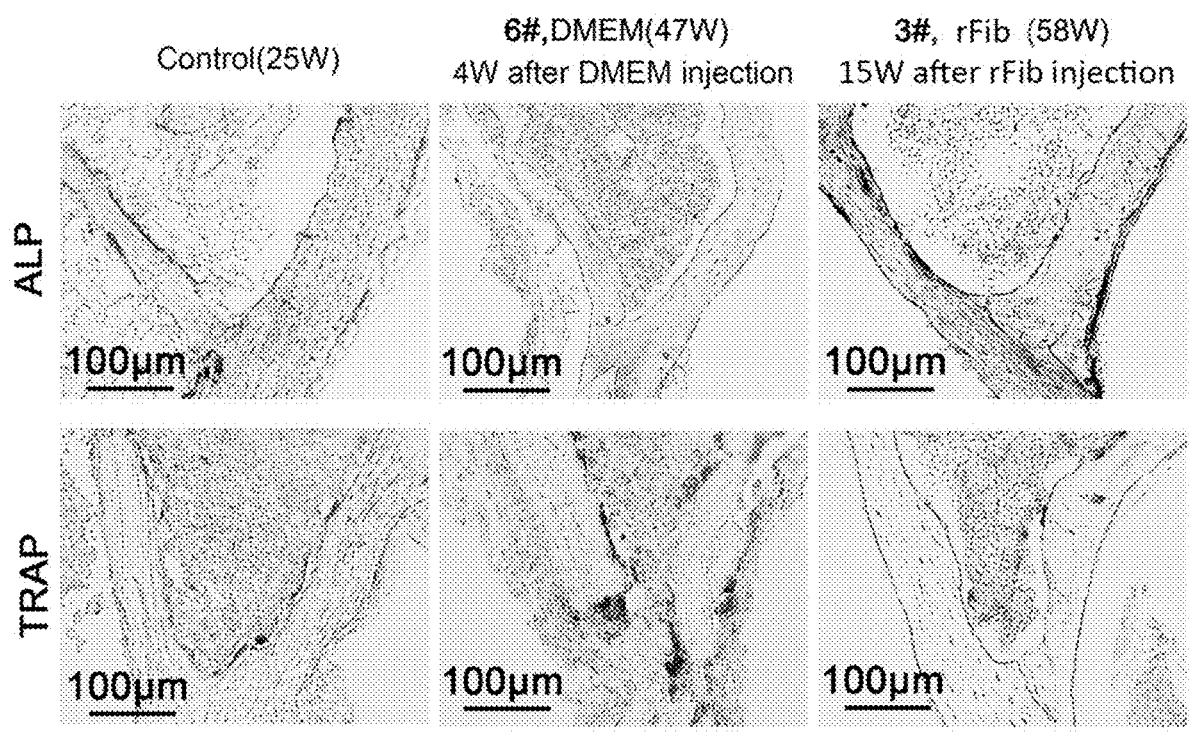
FIG. 50 shows the stained osteoblasts (ALP) and osteoclasts (TRAP) in lumbar spine of aged mice treated by rFib and DMEM.

FIG. 50 illustrated the staining results of osteoblasts (ALP) and osteoclasts (TRAP), where compared to the aged mice injected with DMEM, both bone formation and bone resorption activities of the aged mice injected with rFib were restored to levels of younger mice.

Figure 51A:
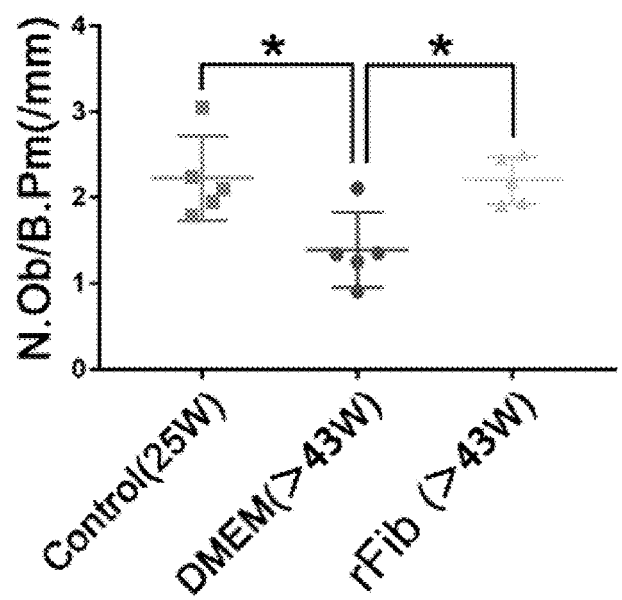
FIGS. 51A-B show the quantification of osteoblasts and osteoclasts in different groups of mice.
Figure 51B:
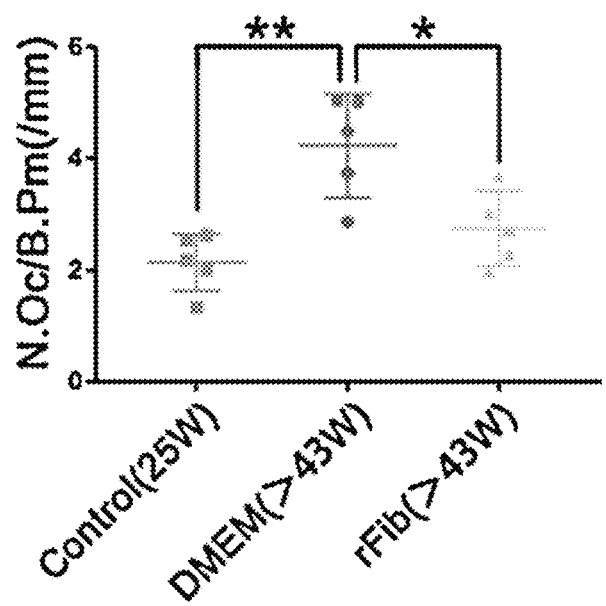

The quantification results of osteoblasts and osteoclasts were respectively shown in FIGS. 51A-B, where the aged mice injected with rFib had similar number of osteoblasts and osteoclasts to the 25-week-old mice.

Figure 52:
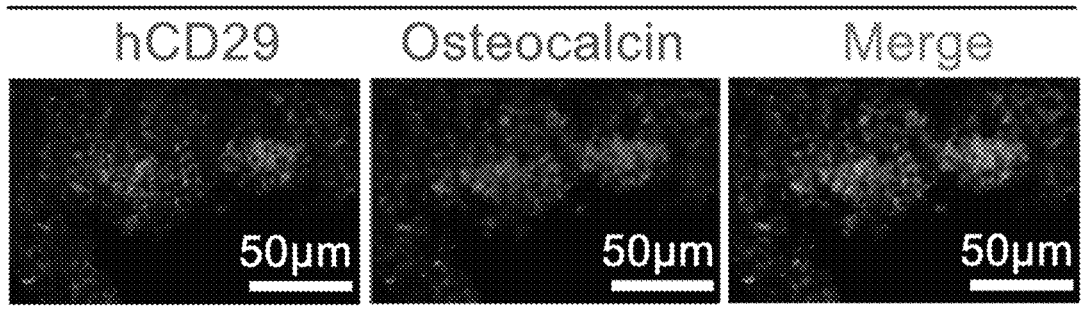
FIG. 52 shows immunohistochemical staining results of lumbar spine in mice injected with rFib using antibodies against human-specific CD29 and osteocalcin.

The lumbar spine of the mice injected with rFib was subjected to immuno histochemical staining, and the results were shown in FIG. 52. It can be clearly seen that the bones of the mice injected with rFib were positive for human antibodies (hCD29), and the osteogenic marker Osteocalcin was expressed, indicating that the rFib differentiated into osteoblasts in NOD/SCID mice.

Figure 53A:
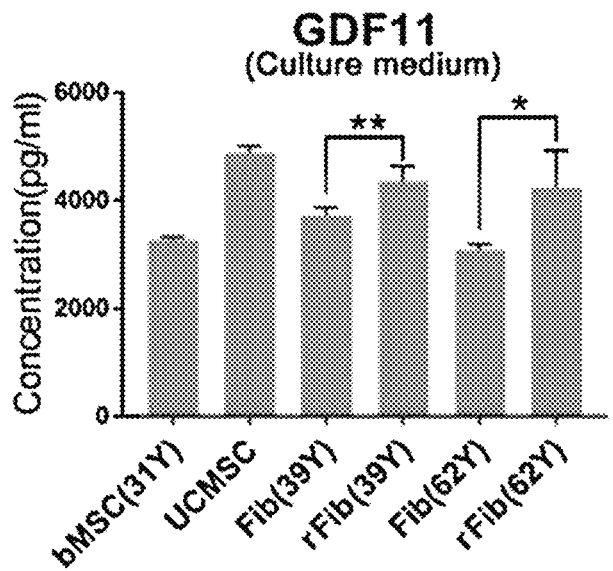
FIGS. 53A-B respectively illustrate concentrations of GDF11 and PDGFA in culture mediums of bMSC, Fib and rFib.
Figure 53B:
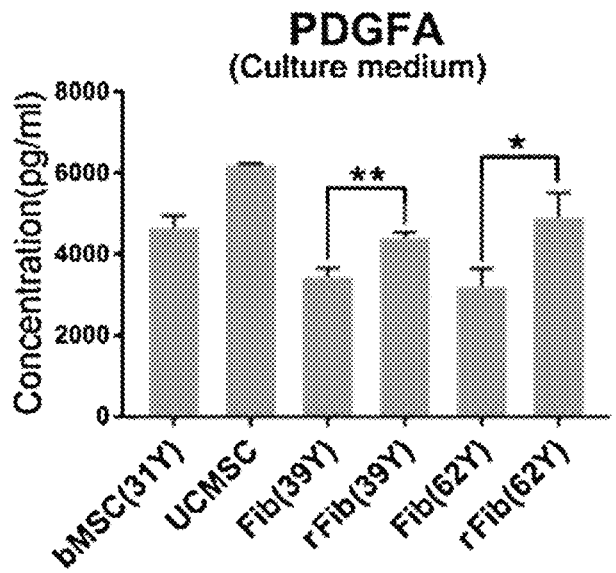
Figure 54:
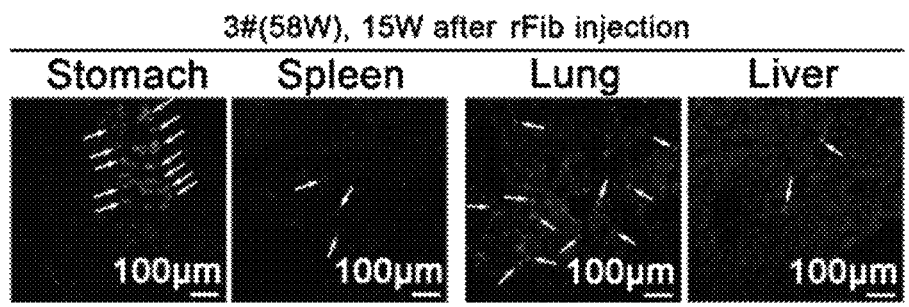
FIG. 54 shows fluorescence detection results of rFib in stomach, spleen, lung and liver of mice injected with rFib.
Figure 55:
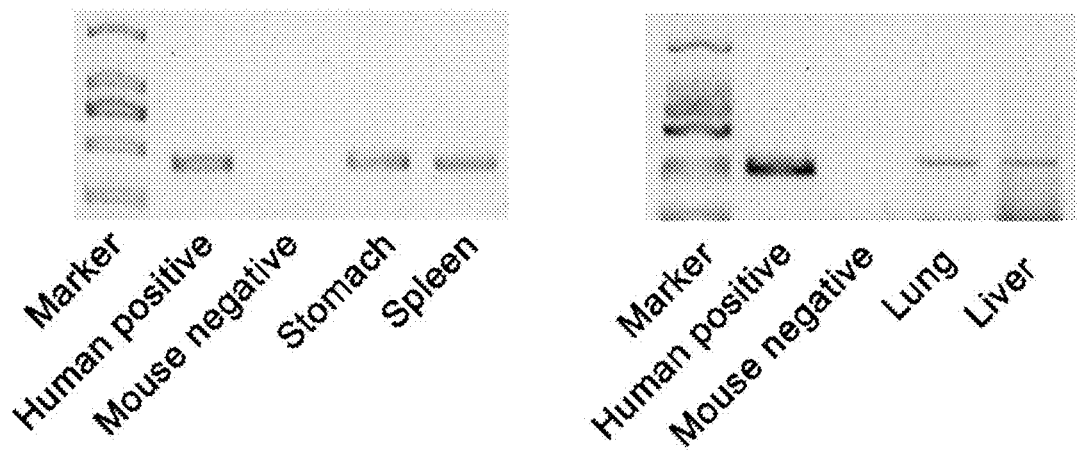
FIG. 55 shows PCR of genomic DNAs of rFib in different organs of mice injected with rFib, using a human-specific actin sequence.
Figure 56:
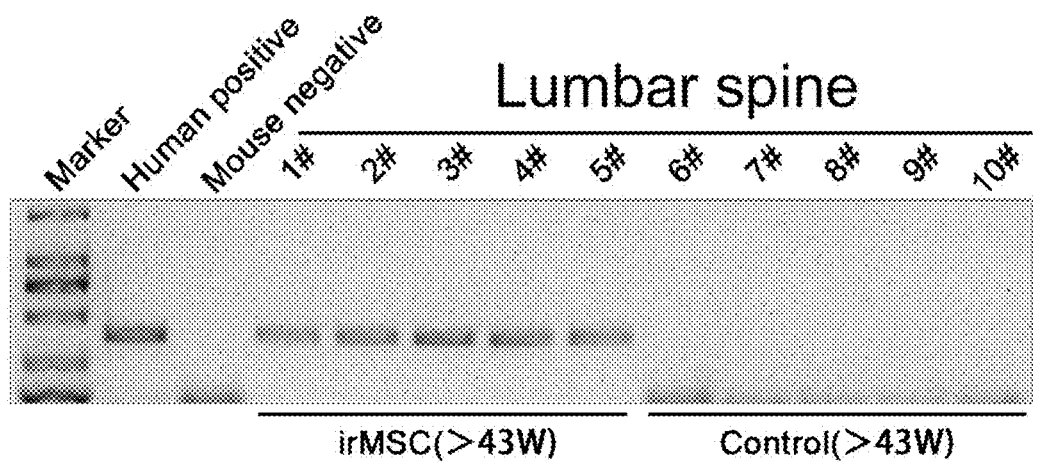
FIG. 56 shows PCR of genomic DNAs of rFib in lumbar spine of mice injected with rFib.

Contents of GDF11 (an anti-aging protein) and PDGFA (platelet derived growth factor submit A, promoting the osteogenesis) in the culture medium of rFib were determined and the results were illustrated in FIGS. 53A-B, respectively. Specifically, the amount of GDF11 and PDGFA secreted from rFib was significantly higher than that secreted from its homologous Fib, which indicated that the anti-aging and bone density-enhancing functions of rFib may be related to paracrine effects.

FIGS. 54-58 demonstrated that the rFibs were distributed in multiple organs of mice.

The distribution of rFib in tissues and organs of mice was detected respectively by fluorescence assay (FIG. 54) and PCR (FIG. 55), and the results demonstrated that the rFib was present in the stomach, spleen, lung and liver.

The presence of rFib in lumbar spine was demonstrated by PCR (FIG. 56), where 1 #-5 #: mice injected with rFib; 6 #-10 #: mice injected with DMEM.

Figure 57:
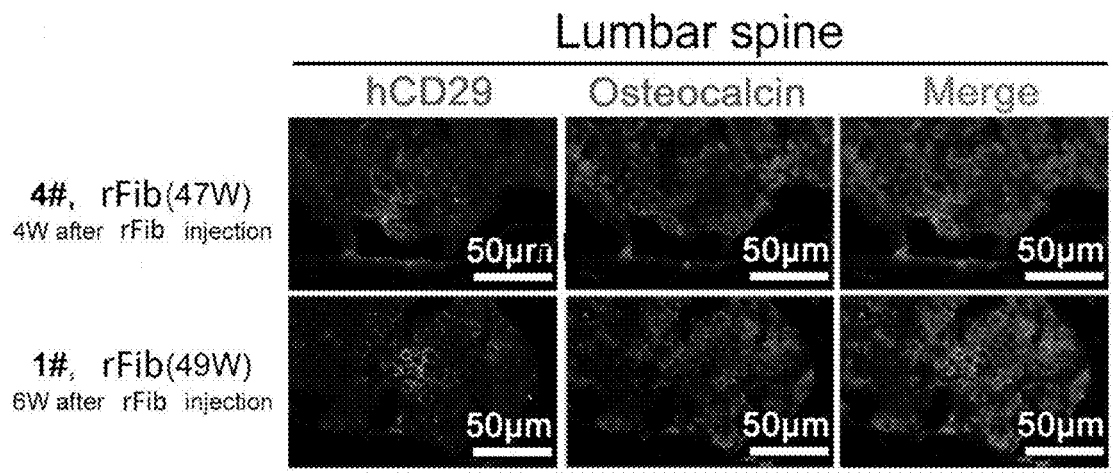
FIG. 57 shows immunohistochemical staining results of lumbar spine in mice injected with rFib, using antibodies against human-specific CD29 and osteocalcin.
Figure 58:
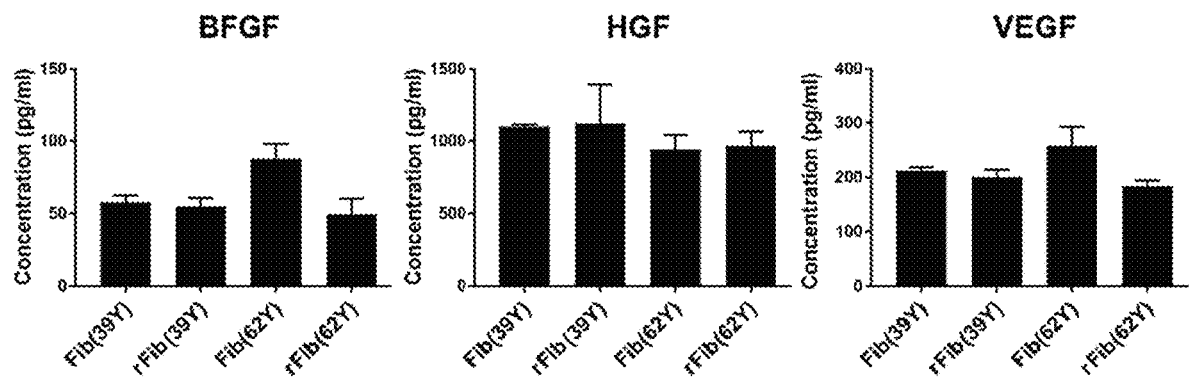
FIG. 58 shows concentrations of BFGF, HGF and VEGF secreted from rFib.

The lumbar spine of the mice injected with rFib was subjected to immunohistochemical staining, and the results were shown in FIG. 57. It can be clearly seen that the bones of the mice injected with rFib were positive for human antibodies (hCD29), and the osteogenic marker Osteocalcin was expressed, indicating that the rFib differentiated into osteoblasts in NOD/SCID mice.

Several other protein factors (BFGF, HGF, VEGF) of rFib were determined (FIG. 58), and the results demonstrated that the rFib was similar to the Fib with respect to the concentration of such substances, which indicated that these paracrine substances were not very associated with the anti-aging mechanism of rFib.

Figure 59:
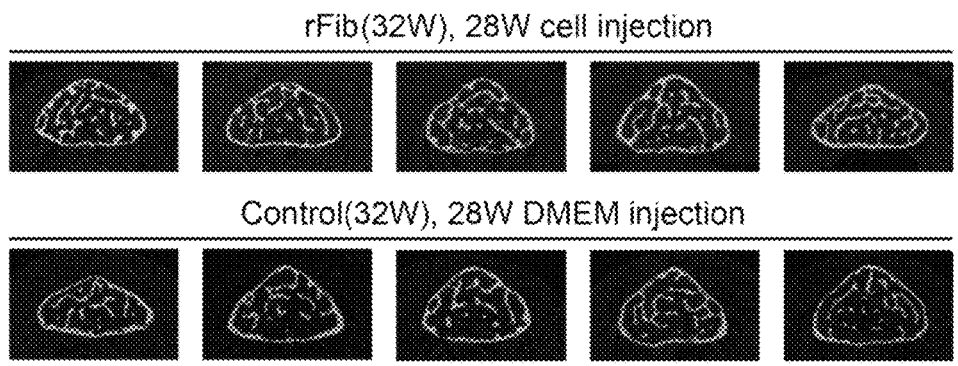
FIG. 59 is micro-CT images of the third lumbar trabecula in mice respectively injected with DMEM and rFib.
Figure 60:
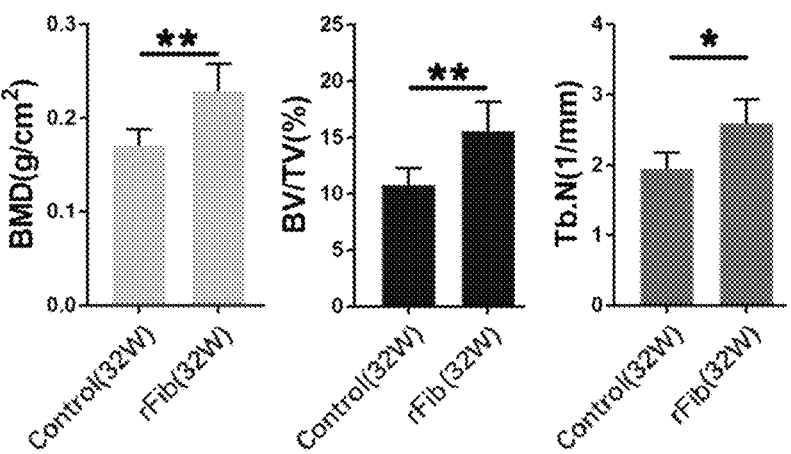
FIG. 60 illustrates BMD, BV/TV ratio and Tb. N of mice in control and rFib groups.

Example 16 Improvement of Bone Density in Aged Osteoporotic Animals by Intravenous Injection of rFib FIGS. 59-60 demonstrated that the rFib can improve the bone density of aged mice with osteoporosis.

Human-derived rFibs were employed to interfere with the senile osteoporosis in 28-week-old NOD/SCID mice. The experimental group was injected with $1*10^6$ rFib cells (in 200 µL of DMEM) through the tail vein, and the control group was merely injected with DMEM. The injection was performed once a week and lasted for 3 weeks. The mice were sacrificed 28 days after the first injection, and the lumbar spine was collected for the detection of lumbar bone density. The micro-CT results revealed that the third lumbar vertebrae of the mice in the experimental group were denser than those of the mice in the control group (FIG. 59).

The micro-CT data indicated that the mice in the experimental group were superior to those in the control group in BMD, BV/TV and Tb. N (FIG. 60).

Example 17 Healing Effect of Culture Medium of rFib on Animal Skin Wounds

Full-thickness defect with a diameter of 8 mm was made on the back of C57 mice. The mice in the control group did not receive treatment, while the mice in the experimental group were smeared with the rFib medium daily.

Figure 61:
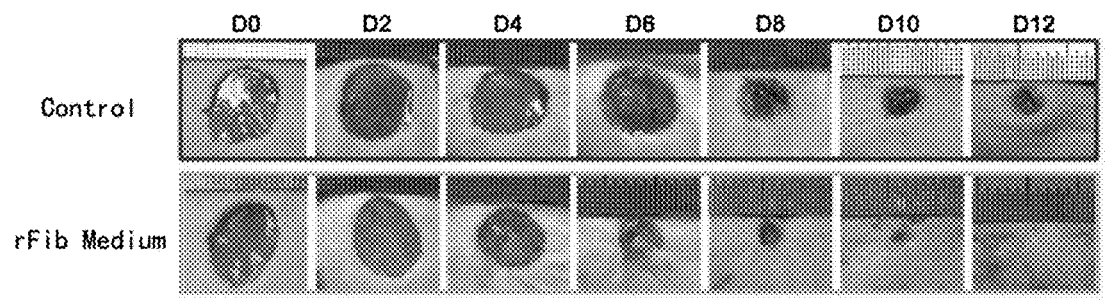
FIG. 61 shows the effect of rFib medium on the injured skin.

As shown in FIG. 61, the rFib medium can significantly promote the healing of injured skin, and the wound on the mice treated with rFib medium was almost completely healed 12 days after modeling.

Example 18 Improvement of rFib for Lower Extremity Ischaemia of Mice

The unilateral femoral artery of NOD/SCID mice was ligated to establish the lower extremity ischemia model, and whether the model was successfully established was determined by laser Doppler. $1\times10^6$ cells were injected into the ligation point of the femoral artery and its distal and proximal ends, and the blood flow was measured by Laser Doppler respectively 7 and 14 days after injection of cells.

Figure 62:
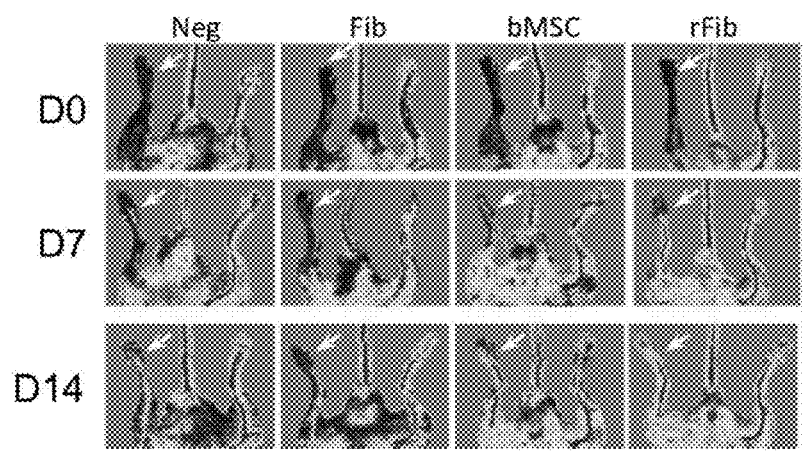
FIG. 62 shows Laser Doppler detection results of blood flow in the lower limbs of mice after different cell transplantation.
Figure 63:
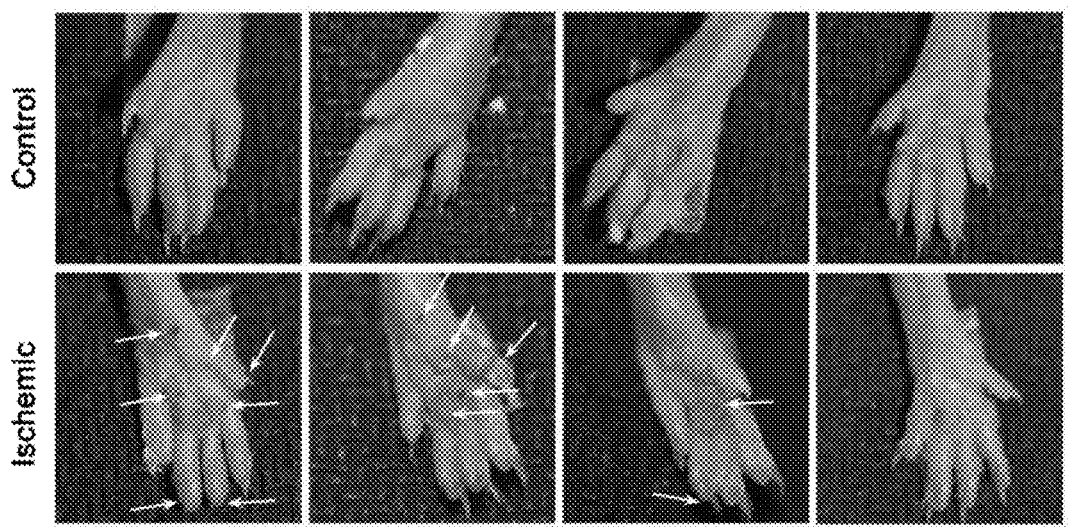
FIG. 63 shows the comparison of the normal lower limb and the ligated lower limb of mice injected with different cells.
Figure 64A:
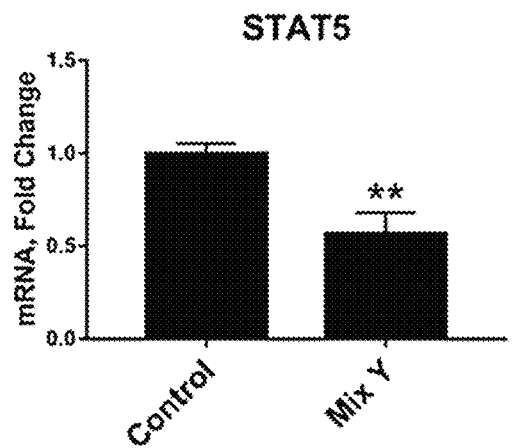
FIGS. 64A-D respectively show expression levels of STAT5, STAT3 and CDKN1A and the relative telomere length in cells after treated with Mix Y.
Figure 64B:
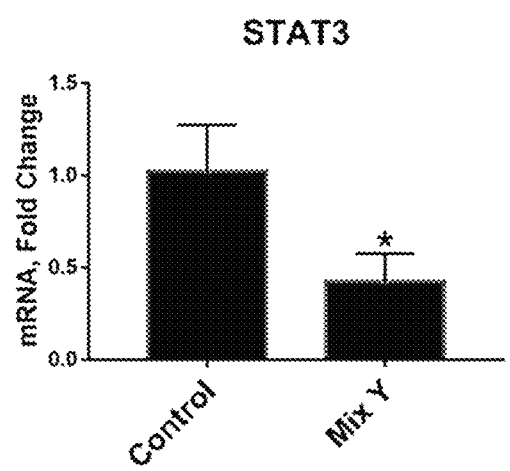
Figure 64C:
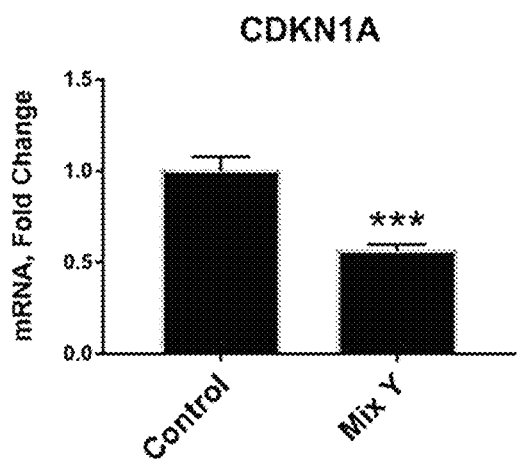
Figure 64D:
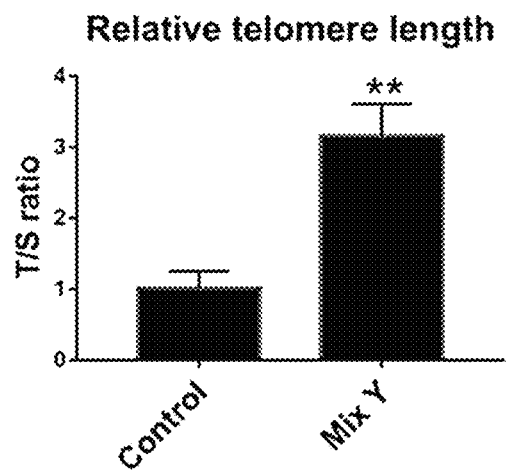
Figure 65A:
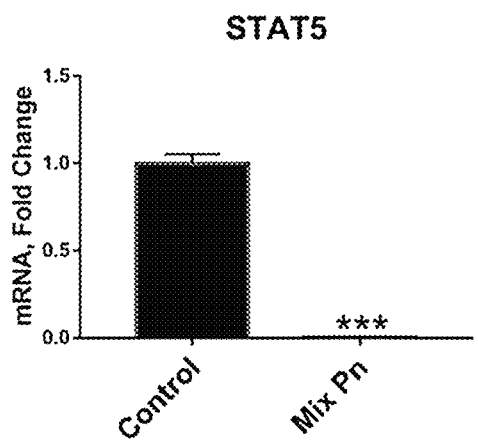
FIGS. 65A-E respectively show expression levels of STAT5, ATF3, CDKN1A, GADD45B and IL6 in cells after treated with Mix Pn.
Figure 65B:
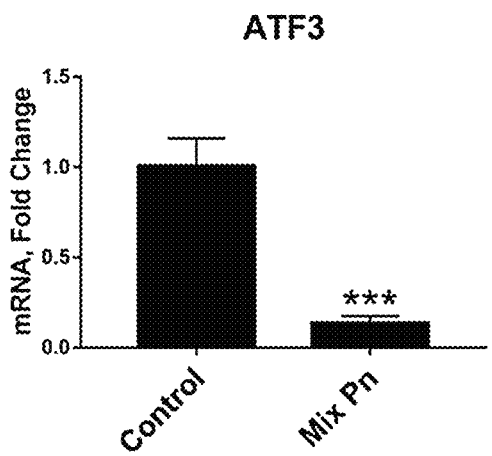
Figure 65C:
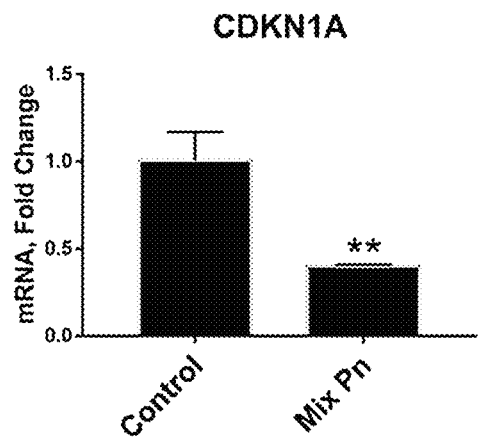
Figure 65D:
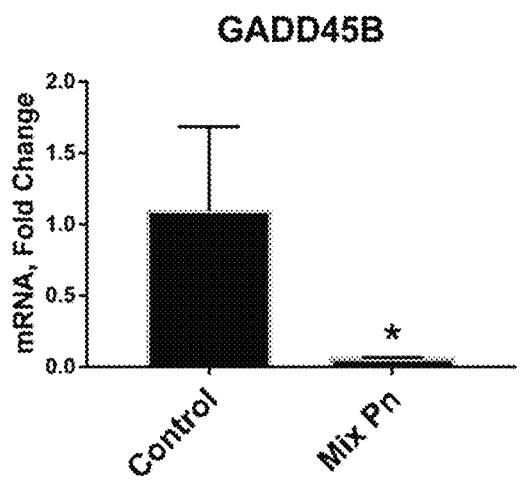
Figure 65E:
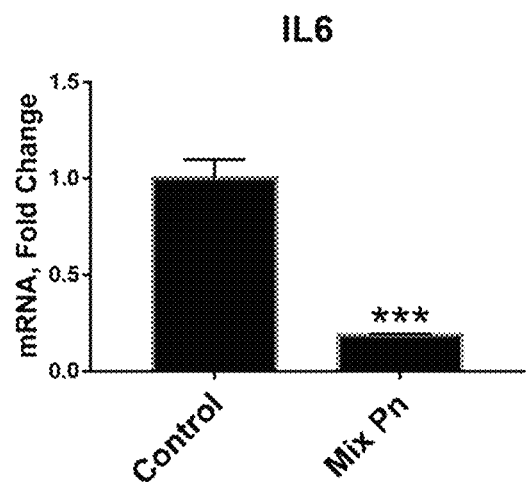

FIGS. 62-63 indicated that the rFib can improve the lower extremity ischemia of mice.

The blood flow in the lower limbs of mice was detected by Laser Doppler, and the results were shown in FIG. 62, where the rFib and bMSC both can significantly alleviate the lower extremity ischemia.

Gross photographs of the lower limbs of the mice 7 days after the ligation were presented in FIG. 63, where control: normal lower limb; ischemic: ligated lower limb. The results showed that the ligated lower limbs of the mice were significantly alleviated after treated with rFib or bMSC.

Example 19 Preparation of rFib Using Various Compound Combinations

1. Skin fibroblasts were seeded onto a 6-well plate and cultured in a Fib medium for 24 hours.

2. The Fib medium was replaced with an rFib induction medium containing the small molecular combination Mix Y, and the cells were cultured in the induction medium for 10 days, where the medium was replaced every two days.

3. Then the induction medium was replaced with a HG-DMEM containing 10% FBS or the rFib medium, and the cells were continuously cultured for 3 days and characterized.

4. During the long-term passage, the rFib was cultured in a MSC basal medium and passaged when the confluency reached 90%.

The Fib medium was a HG-DMEM containing 10% FBS or a commercially-available FibStar medium (cat. no. FMS0030, rFib).

The rFib induction medium Mix Y was a HG-DMEM supplemented with 10% FBS, containing 5 µM of Y-27632, 0.2 mM of Vc, 5 µM of EPZ004777, 10 µM of Forskolin, and 1 µM of Repsox, or prepared by introducing 5 µM of Y-27632, 0.2 mM of Vc, 5 µM of EPZ004777, 10 µM of Forskolin, and 1 µM of Repsox to a commercially-available FibGro medium (cat. no. FGS0040, rFib).

The MSC basal medium was a LG-DMEM containing 10% FBS, a commercially-available complete medium for bMSC (cat. no. HUXMA-90011, Cyagen) or an rFib medium (cat. no. CRM0016-01, rFib).

FIGS. 64A-D demonstrated that the treatment with Mix Y can inhibit the expression of STAT5, STAT3 and CDKN1A genes, and extend the telomere, achieving the cell rejuvenation.

Example 20 Preparation of rFib Using Various Compound Combinations

1. Skin fibroblasts were seeded onto a 6-well plate and cultured in a Fib medium for 24 hours.

2. The Fib medium was replaced with an rFib induction medium containing the small molecular combination Mix Pn, and the cells were cultured in the induction medium for 7 days, where the medium was replaced every two days.

3. Then the induction medium was replaced with a HG-DMEM containing 10% FBS or the rFib medium, and the cells were continuously cultured for 3 days and characterized.

4. During the long-term passage, the rFib was cultured in a MSC basal medium and passaged when the confluency reached 90%.

The Fib medium was a HG-DMEM containing 10% FBS or a commercially-available FibStar medium (cat. no. FMS0030, rFib).

The rFib induction medium Mix Pn was a HG-DMEM supplemented with 10% FBS, containing 0.5 mM of VPA, 3 μM of CHIR99021, 1 μM of Repsox, 10 μM of Forskolin, 5 μM of Go 6983, 5 μM of Y-27632, 0.05 μM of AM580, 5 μM of EPZ004777, 0.2 mM of Vc, 5 UM of TTNPB and 10 μM of 5-Aza-2'-deoxycytidine, or prepared by introducing 0.5 mM of VPA, 3 μM of CHIR99021, 1 μM of Repsox, 10 μM of Forskolin, 5 μM of Go 6983, 5 μM of Y-27632, 0.05 UM of AM580, 5 μM of EPZ004777, 0.2 mM of Vc, 5 μM of TTNPB and 10 μM of 5-Aza-2'-deoxycytidine to a commercially-available FibGro medium (cat. no. FGS0040, rFib).

The MSC basal medium was a LG-DMEM containing 10% FBS, or a commercially-available complete medium for bMSC (cat. no. HUXMA-90011, Cyagen) or an rFib medium (cat. no. CRM0016-01, rFib).

As shown in FIGS. 65A-E, under the treatment of Mix Pn, the expression of STAT5 was down-regulated, and the expression of ATF3, CDKN1A, GADD45B and IL6 was inhibited, indicating that the cells were rejuvenated.

Example 21 Preparation of rFib Using Various Compound Combinations

1. Skin fibroblasts were seeded onto a 6-well plate and cultured in a Fib medium for 24 hours.

2. The Fib medium was replaced with an rFib induction medium containing a cocktail (Mix Y) of small molecules, and the medium was replaced every two days.

3. After 9 days of the culture, the induction medium was replaced with a HG-DMEM containing 10% FBS, and the cells were continuously cultured for 3-7 days.

4. Then the HG-DMEM containing 10% FBS was replaced with another induction medium containing a small molecular combination Mix Pn2, and the induction medium was replaced every two days.

5. After 7 days of the culture in the induction medium, the induction medium was replaced with a HG-DMEM containing 10% FBS, 10 ng/mL of bFGF, 100 ng/ml of PDGF-AB and 10 ng/ml of BMP4, or with a HG-DMEM containing 10% FBS or an rFib medium. The cells were cultured for 3 days and then characterized.

6. During the long-term passage, the rFib was cultured in a MSC basal medium and passaged when the confluency reached 90%.

The Fib medium was a HG-DMEM containing 10% FBS or a commercially-available FibStar medium (cat. no. FMS0030, rFib).

The rFib induction medium containing Mix Y was a HG-DMEM supplemented with 10% FBS, containing 5 μM of Y-27632, 0.2 mM of Vc, 5 μM of EPZ004777, 10 μM of Forskolin and 1 μM of Repsox, or prepared by introducing 5 μM of Y-27632, 0.2 mM of Vc, 5 μM of EPZ004777, 10 μM of Forskolin and 1 μM of Repsox to a commercially-available FibGro medium (cat. no. FGS0040, rFib).

The rFib induction medium containing Mix Pn was a HG-DMEM supplemented with 10% FBS, containing 0.5 mM of VPA, 3 μM of CHIR99021, 1 μM of Repsox, 10 μM of Forskolin, 5 μM of Go 6983, 5 μM of Y-27632, 0.05 μM of AM580, 5 μM of EPZ004777, 0.2 mM of Vc and 5 μM of TTNPB, or prepared by introducing 0.5 mM of VPA, 3 μM of CHIR99021, 1 μM of Repsox, 10 μM of Forskolin, 5 μM of Go 6983, 5 UM of Y-27632, 0.05 μM of AM580, 5 μM of EPZ004777, 0.2 mM of Vc and 5 μM of TTNPB to a commercially-available FibGro medium (cat. no. FGS0040, rFib).

The MSC basal medium was a LG-DMEM containing 10% FBS, or a commercially-available complete medium for bMSC (cat. no. HUXMA-90011, Cyagen) or an rFib medium (cat. no. CRM0016-01, rFib).

Figure 66A:
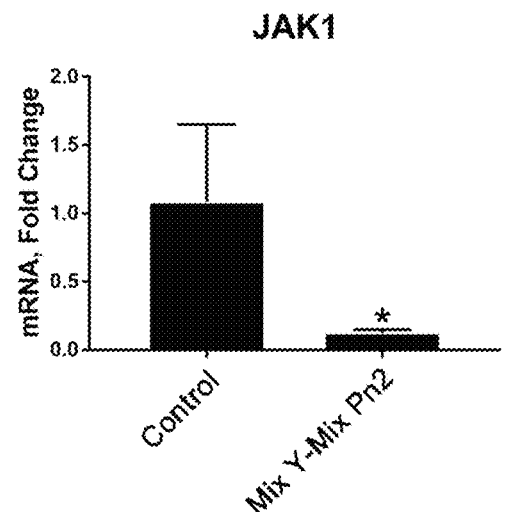
FIGS. 66A-B respectively show expression level of JAK1 and the relative telomere length in fibroblasts after treated with Mix Y-Mix Pn2.
Figure 66B:
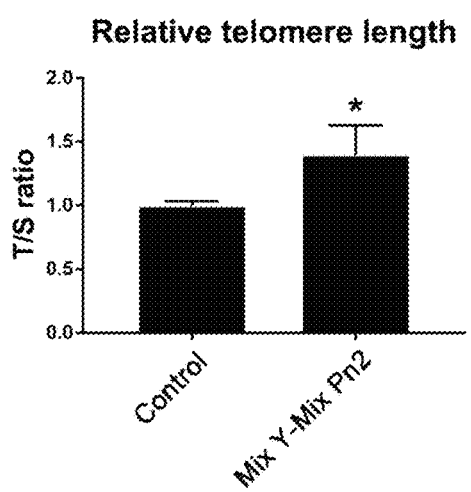

As shown in FIGS. 66A-B, the treatment with Mix Y-Mix Pn2 can inhibit the expression of JAK1 and extend the telomere length in Fib.

Example 22 Transdifferentiation of Skin Fibroblasts into Neurons

1. Skin fibroblasts were seeded onto a 6-well plate and cultured in a Fib medium for 24 hours.

2. The Fib medium was replaced with an induction medium containing a small molecular combination Mix Neu, and the medium was replaced every two days.

3. The cells were cultured with the induction medium for 5-12 days, and then it can be observed that the cell morphology was changed from spindle shape to a shape of nerve cells. The induction medium was replaced with a medium for neurons for continuous passage.

4. The transdifferentiated neurons were identified by immunofluorescence assay and quantitative PCR.

The Fib medium was a HG-DMEM containing 10% FBS or a commercially-available FibStar medium (cat. no. FMS0030, rFib).

The induction medium containing Mix Neu was a HG-DMEM supplemented with 10% FBS, containing 0.5 μM of A8301, 10 ng/ml of bFGF, 5 μM of EPZ004777, 10 μM of RG108, 2 μM of parnate, 10 μM of CHIR99021, 50 μM of Forskolin, 0.5 mM of VPA, 0.05 μM of AM580 and 1 μM of BIX 01294.

The neuron culture medium consisted of 5 mL of DMEM/F12, 5 mL of Neurobasal, 1/100 of N2, 1/50 of B27, 100 μM of CAMP, 20 ng/mL of BDNF, 20 ng/ml of GDNF and 10% KOSR (v/v).

Figure 67:
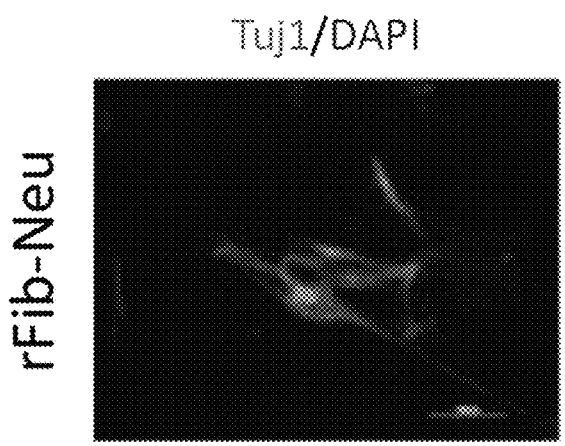
FIG. 67 shows stained Tuj1 in neurons derived from rFib.
Figure 68:
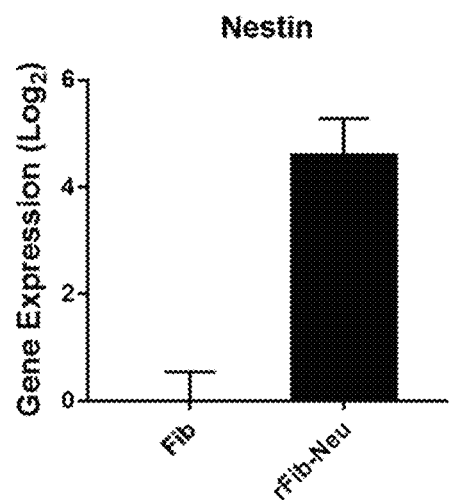
FIG. 68 shows expression level of Nestin in Fib and neurons derived from rFib.

FIGS. 67-68 illustrated the identification of neurons transdifferentiated from fibroblasts, where FIG. 67: staining of Tuj1 in neurons transdifferentiated from fibroblasts; FIG. 68: measurement of expression level of Nestin.

Example 23 Differentiation of Embryonic Stem Cells into Neurons

1. The adherent embryonic stem cells were digested and then suspended with a neural induction medium.

2. After 10-15 days of culture in the neural induction medium, it can be observed that the cell spheres adhered to the wall. The cell spheres under suspension culture were transferred to a 6-well plate pretreated with matrigel to perform adherent culture in the neural induction medium for 5-7 days.

3. After the cells adhered to the wall, the neural induction medium was replaced with a neuron culture medium.

4. The induced cells were identified by immunofluorescence staining of neural markers and quantitative PCR.

The neural induction medium was a DMEM/F12 supplemented with 10% KOSR, containing 10 ng/ml of bFGF, 5

μM of Y-27632, 0.5 mM of VPA, 5 μM of EPZ004777, 10 μM of Forskolin and 1 μM of Repsox.

The neuron culture medium consisted of 5 mL of DMEM/F12, 5 mL of Neurobasal, 1/100 of N2, 1/50 of B27, 100 μM of cAMP, 20 ng/ml of BDNF, 20 ng/ml of GDNF and 10% KOSR (v/v).

Figure 69:
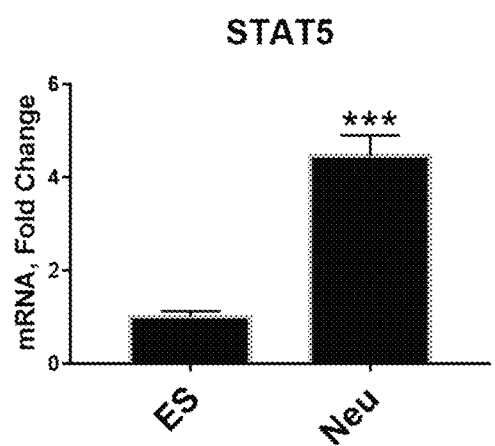
FIG. 69 shows expression level of STAT5 gene in ES and neurons.
Figure 70A:
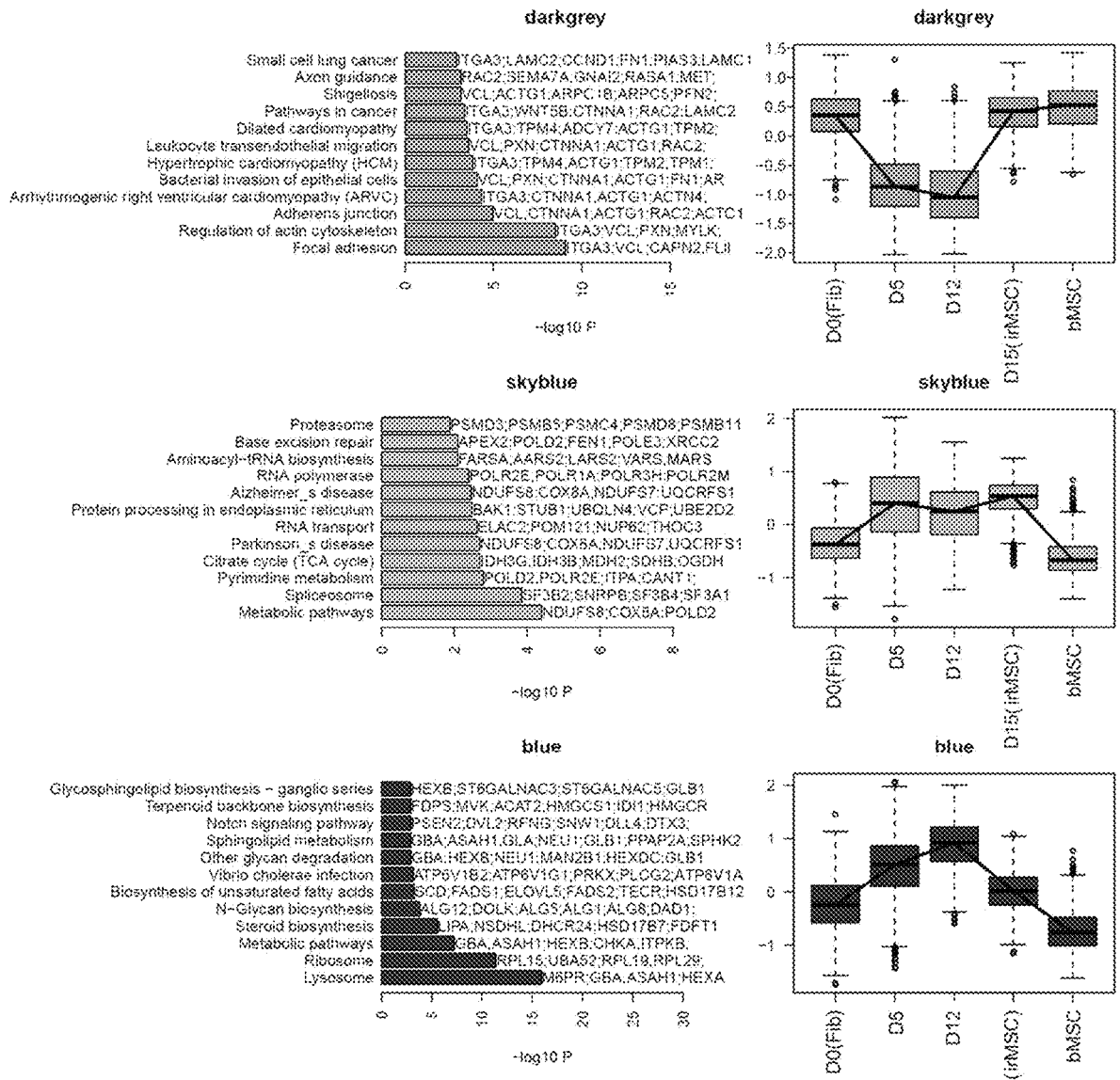
FIGS. 70A-D show KEGG pathways enriched in 12 modules in bar plots and distribution of averaged expression level of genes in each module in box plots by transcriptomic analysis during the Fibroblast-to-rFib conversion.
Figure 70B:
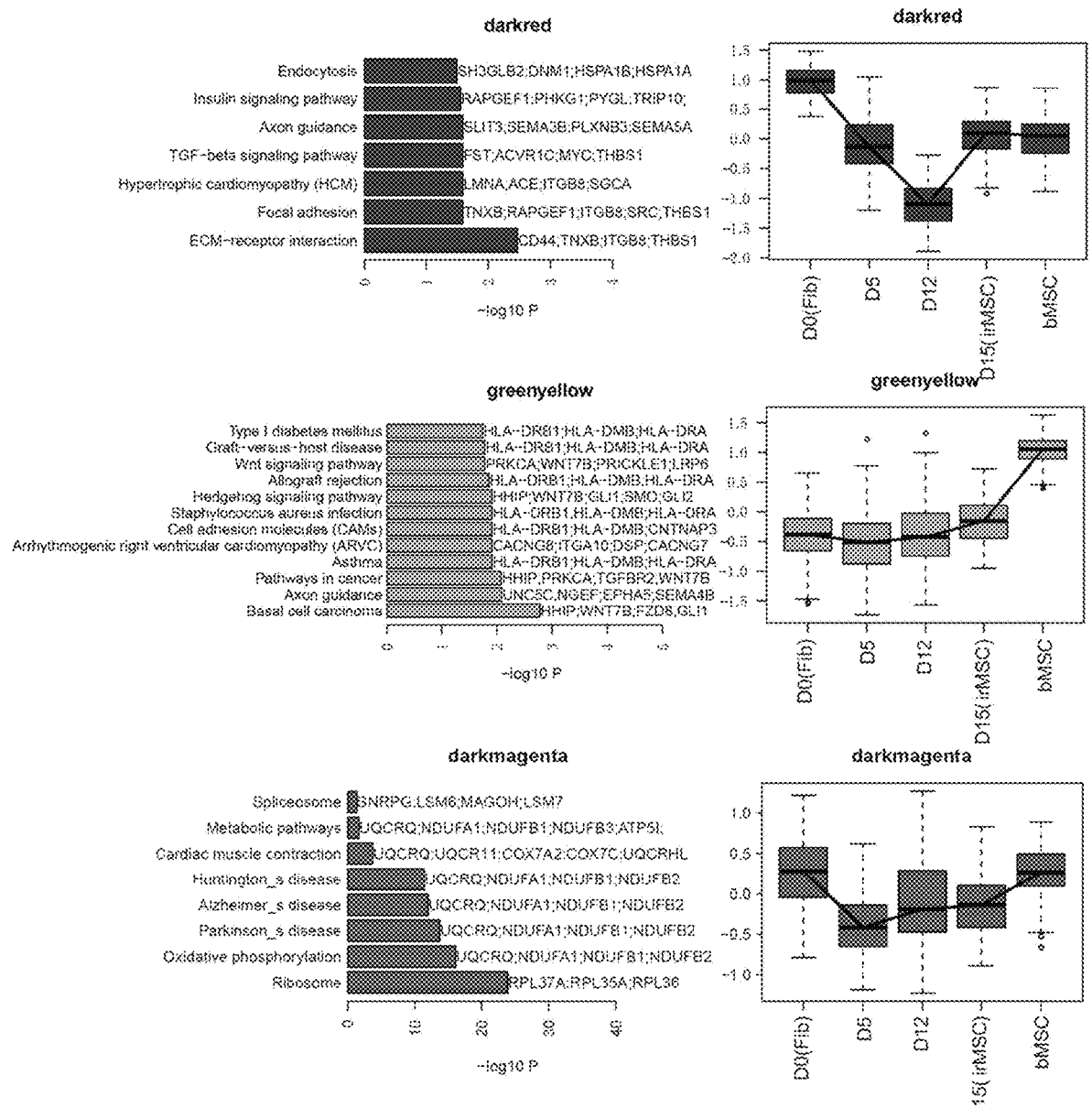
Figure 70C:
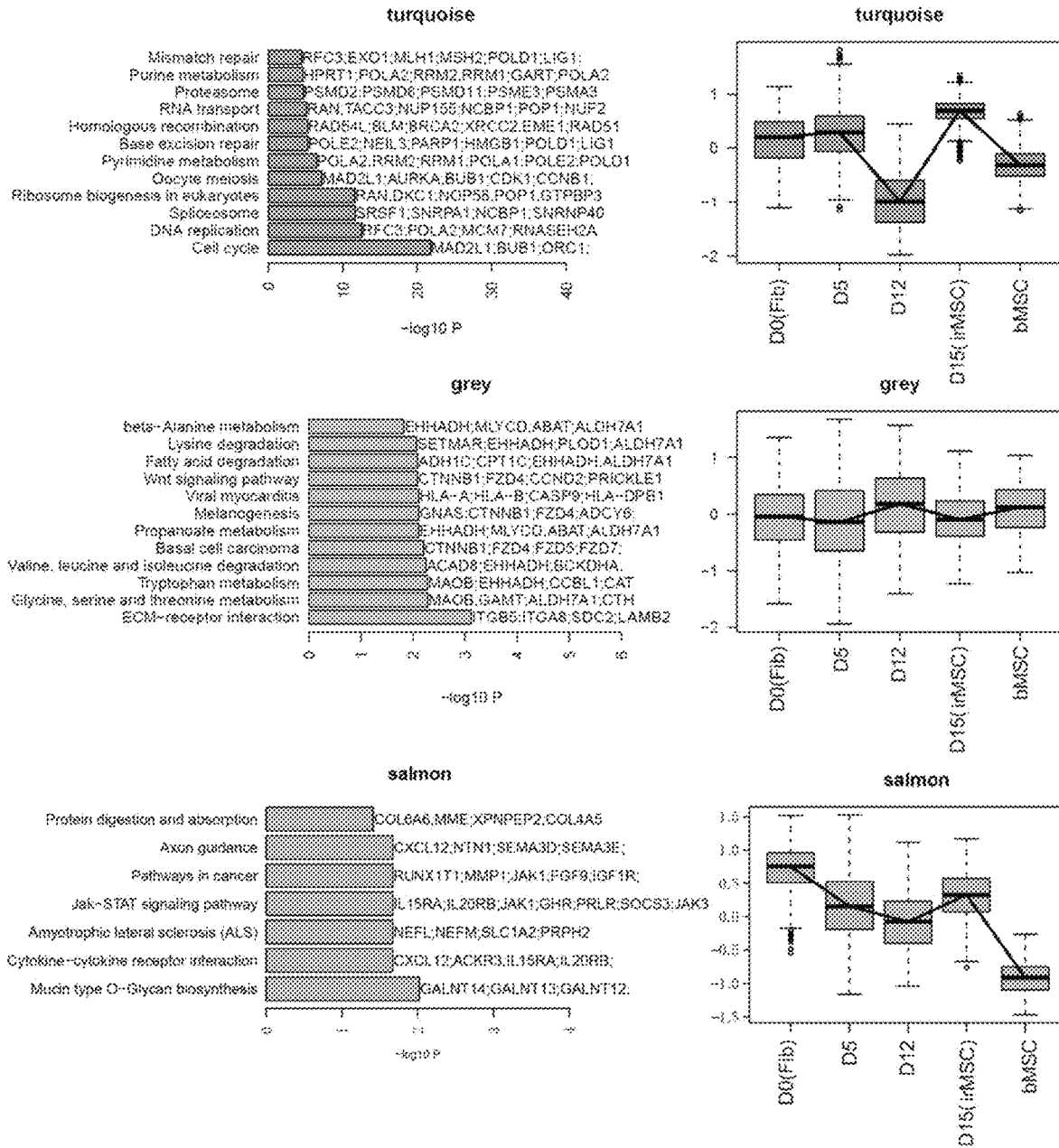
Figure 70D:
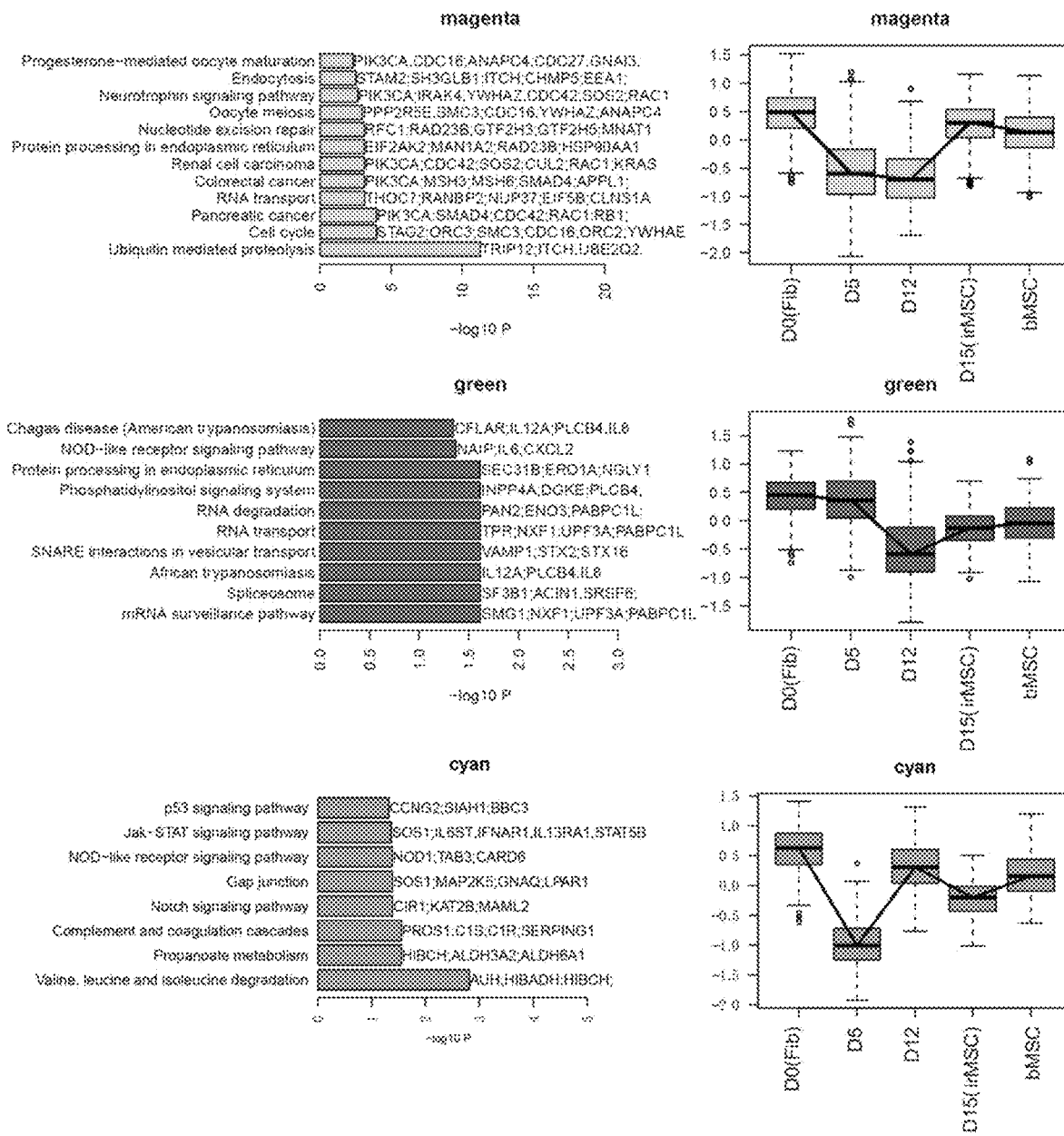

As shown in FIG. 69, under the action of the small molecular combination, the expression of STAT5 gene was up-regulated during the differentiation from ES into neurons.

Example 24 Characterization of Signaling Pathways in rFib Prepared in Example 1

The rFibs from different donors which were prepared according to the method in Example 1 were subjected to transcriptome sequencing, and a total of 12036 genes in each sample were analyzed by WGCNA to obtain 12 clustering modules.

FIGS. 70A-D illustrated KEGG pathways enriched in 12 modules in bar plots and distribution of averaged expression level of genes in each module in box plots by transcriptomic analysis during the Fibroblast-to-rFib Conversion.

What is claimed is:

1. A method of preparing rejuvenated and regenerative fibroblasts, comprising:
    treating fibroblasts sequentially with a first composition and a second composition;
    wherein the first composition comprises high glucose DMEM (HG-DMEM) supplemented with 10% fetal bovine serum (FBS) and a first small molecule mixture consisting of WNT/β-catenin agonist CHIR99021, histone deacetylase (HDAC) inhibitor valproic acid (VPA), cyclic adenosine monophosphate (cAMP) agonist Forskolin, and transforming growth factor (TGF)-β inhibitor Repsox; and
    the second composition comprises HG-DMEM supplemented with 10% FBS and a second small molecule mixture consisting of HDAC inhibitor VPA, TGF-β inhibitor Repsox, WNT/β-catenin agonist CHIR99021, cAMP agonist Forskolin, retinoic acid receptor (RAR) agonists AM580 and TTNPB, histone methyltransferase (HMT) inhibitor EPZ004777, ascorbate, protein kinase C (PKC) inhibitor Go 6983, Rho-associated coiled-coil kinase (ROCK) inhibitor Y-27632, and c-Jun N-terminal kinase (JNK) inhibitor SP600125;
    wherein the fibroblasts are treated in the first composition for 5 days, and the fibroblasts are treated in the second composition for 7 days.

2. The method of claim 1, wherein the fibroblasts are derived from a connective tissue of a mammal.

3. The method of claim 2, wherein the connective tissue is blood, skin, bone marrow, heart, blood vessel, muscle, urine, liver, kidney, digestive tract, lung, bone, cartilage, adipose, placenta or umbilical cord.

4. The method of claim 2, wherein the mammal is human, monkey, mouse, pig, rat, dog, cattle, sheep, goat, horse, tree shrew or rabbit.

5. The method of claim 1, wherein the first small molecule mixture consists of 0.05-10 mM of VPA, 1-15 μM of CHIR99021, 0.5-10 μM of Repsox, and 3-50 μM of Forskolin.

6. The method of claim 1, wherein the second small molecule mixture consists of 0.05-10 mM of VPA, 1-15 μM of CHIR99021, 0.5-10 μM of Repsox, 3-50 μM of Forskolin, 1-50 μM of SP600125, 1-20 μM of Go 6983, 1-25 μM of Y-27632, 0.02-1 μM of AM580, 0.5-15 μM of EPZ004777, 0.2 mM of ascorbate, and 0.2-20 μM of TTNPB.

7. A method of preparing rejuvenated and regenerative fibroblasts, comprising:
    treating fibroblasts sequentially with a first composition and a second composition;
    wherein the first composition comprises HG-DMEM supplemented with 10% FBS and a first small molecule mixture consisting of ROCK inhibitor Y-27632, ascorbate, HMT inhibitor EPZ004777, cAMP agonist Forskolin and TGF-β inhibitor Repsox; and
    wherein the second composition comprises HG-DMEM supplemented with 10% FBS and a second small molecule mixture consisting of HDAC inhibitor VPA, WNT/β-catenin agonist CHIR99021, TGF-β inhibitor Repsox, cAMP agonist Forskolin, PKC inhibitor Go 6983, ROCK inhibitor Y-27632, RAR agonists AM580 and TTNPB, HMT inhibitor EPZ004777, and ascorbate;
    wherein the fibroblasts are treated in the first composition for 9 days, and the fibroblasts are treated in the second composition for 7 days.

8. The method of claim 7, wherein the first small molecule mixture consists of 1-25 μM of Y-27632, 0.2 mM of ascorbate, 0.5-15 μM of EPZ004777, 3-50 UM of Forskolin and 0.5-10 μM of Repsox.

9. The method of claim 7, wherein the second small molecule mixture consists of 0.05-10 mM of VPA, 1-15 μM of CHIR99021, 0.5-10 μM of Repsox, 3-50 μM of Forskolin, 1-20 μM of Go 6983, 1-25 μM of Y-27632, 0.02-1 μM of AM580, 0.5-15 μM of EPZ004777, 0.2 mM of ascorbate and 0.2-20 μM of TTNPB.

10. The method of claim 7, wherein the fibroblasts are derived from a connective tissue of a mammal.

11. The method of claim 10, wherein the connective tissue is blood, skin, bone marrow, heart, blood vessel, muscle, urine, liver, kidney, digestive tract, lung, bone, cartilage, adipose, placenta or umbilical cord.

12. The method of claim 10, wherein the mammal is human, monkey, mouse, pig, rat, dog, cattle, sheep, goat, horse, tree shrew or rabbit.

* * * * *